(12) United States Patent
Espley et al.

(10) Patent No.: US 8,686,125 B2
(45) Date of Patent: Apr. 1, 2014

(54) CHIMERIC PROMOTERS COMPRISING MYB10 REPEAT ELEMENT AND METHODS FOR REGULATING PLANT GENE EXPRESSION

(75) Inventors: Richard Espley, Auckland (NZ); Roger P. Hellens, Auckland (NZ); Andrew C. Allan, Auckland (NZ); David Chagne, Palmerston North (NZ); Cyril Brendolise, Auckland (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 330 days.

(21) Appl. No.: 12/992,543

(22) PCT Filed: May 12, 2009

(86) PCT No.: PCT/NZ2009/000076
§ 371 (c)(1),
(2), (4) Date: Mar. 16, 2011

(87) PCT Pub. No.: WO2009/139649
PCT Pub. Date: Nov. 19, 2009

(65) Prior Publication Data
US 2011/0271396 A1    Nov. 3, 2011

(30) Foreign Application Priority Data
May 12, 2008 (NZ) ........................................ 568190

(51) Int. Cl.
| | |
|---|---|
| *C07H 21/00* | (2006.01) |
| *C07H 21/04* | (2006.01) |
| *C12N 15/00* | (2006.01) |
| *C12N 15/09* | (2006.01) |
| *C12N 15/113* | (2010.01) |
| *C12N 15/63* | (2006.01) |
| *C12N 15/82* | (2006.01) |
| *A01H 1/00* | (2006.01) |
| *A01H 4/00* | (2006.01) |
| *A01H 5/00* | (2006.01) |

(52) U.S. Cl.
USPC ....... 536/24.1; 536/22.1; 536/23.1; 536/23.6; 435/410; 435/243; 435/320.1; 435/419; 800/278; 800/295; 800/298

(58) Field of Classification Search
None
See application file for complete search history.

(56) References Cited

U.S. PATENT DOCUMENTS

| 4,795,855 A | 1/1989 | Fillatti et al. |
| 5,004,863 A | 4/1991 | Umbeck |

(Continued)

FOREIGN PATENT DOCUMENTS

| NZ | 555127 | 5/2007 |
| WO | 2008/140334 | 11/2008 |
| WO | 2009/139649 | 11/2009 |

OTHER PUBLICATIONS

Takos et al. Light-induced Expression of a MYB gene regulates anthocyanin biosynthesis in red apples. Plant Physiology. 2006. 142(3): 1216-1232.*

(Continued)

*Primary Examiner* — Cathy Kingdon Worley
*Assistant Examiner* — Ashley K Buran
(74) *Attorney, Agent, or Firm* — Lathrop & Gage LLP

(57) ABSTRACT

The invention provides a method for producing a chimeric promoter polynucleotide capable of controlling transcription of an operably linked polynucleotide in a plant cell or plant, wherein the method comprises combining: a) at least one sequence motif comprising a sequence with at least 70% identity to SEQ ID NO:1, 11 or 12, and b) another polynucleotide sequence. The invention also provides chimeric promoters polynucleotides comprising the sequences defined in a) and b). The invention also provides constructs, vectors, host cells, plant cells and plants comprising the chimeric promoter polynucleotides of the invention. The invention also provided methods for modifying gene expression and phenotype of plant cells and plants by transforming the plant cells and plants with the chimeric promoter polynucleotides of the invention.

35 Claims, 15 Drawing Sheets

(56) References Cited

U.S. PATENT DOCUMENTS

| | | | |
|---|---|---|---|
| 5,159,135 A | 10/1992 | Umbeck | |
| 5,177,010 A | 1/1993 | Goldman et al. | |
| 5,187,073 A | 2/1993 | Goldman et al. | |
| 5,188,958 A | 2/1993 | Moloney et al. | |
| 5,352,605 A | 10/1994 | Fraley et al. | |
| 5,364,780 A | 11/1994 | Hershey et al. | |
| 5,416,011 A | 5/1995 | Hinchee et al. | |
| 5,463,174 A | 10/1995 | Moloney et al. | |
| 5,510,474 A | 4/1996 | Quail et al. | |
| 5,563,055 A | 10/1996 | Townsend et al. | |
| 5,569,834 A | 10/1996 | Hinchee et al. | |
| 5,591,616 A | 1/1997 | Hiei et al. | |
| 5,750,871 A | 5/1998 | Moloney et al. | |
| 5,792,935 A | 8/1998 | Arntzen et al. | |
| 5,824,877 A | 10/1998 | Hinchee et al. | |
| 5,846,797 A | 12/1998 | Strickland | |
| 5,952,543 A | 9/1999 | Firoozabady et al. | |
| 5,968,830 A | 10/1999 | Dan et al. | |
| 5,981,840 A | 11/1999 | Zhao et al. | |
| 6,020,539 A | 2/2000 | Goldman et al. | |
| 6,037,522 A | 3/2000 | Dong et al. | |
| 6,074,877 A | 6/2000 | D'Halluin et al. | |
| 2002/0160378 A1* | 10/2002 | Harper et al. | 435/6 |
| 2004/0009476 A9 | 1/2004 | Harper et al. | |
| 2004/0025205 A1* | 2/2004 | Spangenberg et al. | 800/287 |
| 2007/0016976 A1 | 1/2007 | Katagiri et al. | |
| 2007/0118921 A1 | 5/2007 | Boukharov et al. | |
| 2007/0209085 A1 | 9/2007 | Wu et al. | |

OTHER PUBLICATIONS

Telias et al. Apple skin patterning is associated with differential expression of MYB10. BMC Plant Biology. 2011. 11(93): 1-15.*
Kim et al. A 20 nucleotide upstream element is essential for the nopaline synthase (nos) promoter activity. Plant Molecular Biology. 1994. 24: 105-117.*
Jin et al. Multifunctional and diversity within the plant MYB-gene family. Plant Molecular Biology. 1999. 41(5): 577-585.*
Takos et al. *Malus* x domestica MYB transcription factor (MYB1) gene, MYB1-1 allele, promoter region and complete cds. GenBank Accession No. DQ886414.1. Published Nov. 18, 2006.*
Gonzalez et al. Regulation of the anthocyanin biosynthetic pathway by the TTG1/bHLH/Myb transcriptional complex in *Arabidopsis* seedlings. The Plant Journal. 2008. 53: 814-827.*
Allan et al. (Jul. 21, 2006) NCBI Nucleotide Accession No. DQ267900.1, "*Malus* x domestica cultivar Royal Gala MYB9 mRNA, complete cds".
Gleave, A. (Nov. 4, 2010) NCBI Nucleotide Accession No. CN934367.1, "000202AVBB002218HT (AVBB) Royal Gala young shoot *Malus* x domestica cDNA clone AVBB002218, mRNA sequence".
Romero et al. (Apr. 18, 2005) NCBI Nucleotide Accession No. CAB09230.1, "R2R3-MYB transcription factor [*Arabidopsis thaliana*]".
Takos et al. (Nov. 18, 2006) NCBI Nucleotide Accession No. DQ886414.1, "*Malus* x domestica MYB transcription factor (MYB1) gene, MYB1-1 allele, promoter region and complete cds".
Takos et al. (Nov. 18, 2006) NCBI Nucleotide Accession No. DQ886415.1, "*Malus* x domestica MYB transcription factor (MYB1) gene, MYB1-2 allele, promoter region and complete cds".
Takos et al. (Nov. 18, 2006) NCBI Nucleotide Accession No. DQ886416.1, "*Malus* x domestica MYB transcription factor (MYB1) gene, MYB1-3 allele, promoter region and complete cds".
NCBI Nucleotide Accession No. NM_105042.4 (Apr. 30, 2008) "*Arabidopsis thaliana* transcription factor EGL1 (EGL3) mRNA, complete cds".
NCBI Nucleotide Accession No. NM_104541.3 (Apr. 30, 2008) "*Arabidopsis thaliana* transcription factor MYB75 (PAP1) mRNA,complete cds".
International Preliminary Report on Patentability, dated Mar. 24, 2010, corresponding to International Application No. PCT/NZ2009/000076 (filed May 12, 2009), parent of the present application, 11 pp.
Search Report, dated Oct. 7, 2009, corresponding to International Application No. PCT/NZ2009/000076 (filed May 12, 2009), parent of the present application, 10 pp.
Alam et al. (1999) "Transgenic insect-resistant maintainer line (IR68899B) for improvement of hybrid rice," Plant Cell Reports 18:572-575.
Albert et al. (1997) "*BANYULS*, a Novel Negative Regulator of Flavonoid Biosynthesis in the *Arabidopsis* Seed Coat," Plant Journal 11(2):289-299.
Altschul et al. (1997) "Gapped BLAST and PSI-BLAST: a new generation of protein database search programs," Nucleic Acids Res 25(17):3389-3402.
Bajaj et al. (2006) "A High Throughput *Agrobacterium tumefaciens*-Mediated Transformation Method for Functional Genomics of Perennial Ryegrass (*Lolium perenne* L.)," Plant Cell Rep. 25:651-659.
Baxevanis, A.D. (2001) "The Molecular Biology Database Collection: an updated compilation of biological database resources," Nucleic Acids Research 29(1):1-10.
Birch, R.G. (1997) "Plant Transformation: Problems and Strategies for Practical Application," Ann Rev Plant Phys Plant Mol Biol 48:297-326.
Bolton et al. (1962) "A General Method for the Isolation of RNA Complementary to DNA," PNAS 48:1390-1397.
Borevitz et al. (Dec. 2000) "Activation Tagging Identifies a Conserved MYB Regulator of Phenylpropanoid Biosynthesis," Plant Cell 12: 2383-2393.
Bulley et al. (2009) "Gene Expression Studies in Kiwifruit and Gene Over-Expression in *Arabidopsis* Indicates That GDP-$_L$-Galactose Guanyltransferase is a Major Control Point of Vitamin C Biosynthesis," J Exp Bot 60(3):765-778.
Chagné et al. (2007) "Mapping a Candidate Gene (MdMYB10) for Red Flesh and Foliage Colour in Apple," BMC Genomics, 8:212, 11 pp, published online Jul. 3, 2007.
Degenhardt et al. (1994) "Two 10-bp Regions are Critical for Phytochrome Regulation of a *Lemna gibba* Lhcb Gene Promoter," Plant Cell 6(8):1123-1134.
Espley et al. (2007) "Red Colouration in Apple Fruit is Due to the Activity of the MYB Transcription Factor, MdMYB10," Plant J. 49:414-427.
Espley et al. (2009) "Multiple Repeats of a Promoter Segment Causes Transcription Factor Autoregulation in Red Apples," Plant Cell 21:168-183.
Feng and Doolittle (1987) "Progressive Sequence Alignment as a Prerequisite to Correct Phylogenetic Trees," J. Mol. Evol. 25:351-360.
Folta et al. (2006) "Characterization of LF9, an octoploid strawberry genotype selected for rapid regeneration and transformation," Planta 224:1058-1067.
Frohman, M.A. (1993) "Rapid Amplification of Complementary DNA Ends for Generation of Full-Length Complementary DNAs: Thermal RACE," Methods Enzymol. 218:340-356.
Gleave, A. P. (1992) "A Versatile Binary Vector System with a T-DNA Organisational Structure Conducive to Efficient Integration of Cloned DNA into the Plant Genome," Plant Mol Biol 20:1203-1207.
Gonzalez Padilla et al. (2003) "Early antibiotic selection and efficient rooting and acclimatization improve the production of transgenic plum plants (*Prunus domestica* L.)," Plant Cell Reports 22(1):38-45.
Graham et al. (1995) "*Agrobacterium*-Mediated Transformation of Soft Fruit *Rubus, Ribes*, and *Fragaria*," Methods Mol Biol. 44:129-33.
Gruber, et al. (1993) "Vectors for Plant Transformation" Methods in Plant Molecular Biology and Biotechnology) et al. eds, CRC Press, pp. 89-119.
Hashimoto et al. (2004) "5'-End SAGE for the Analysis of Transcriptional Start Sites," Nature Biotechnology 22(9):1146-1149.
Hellens et al. (2005) "Transient expression vectors for functional genomics, quantification of promoter activity and RNA silencing in plants," Plant Methods 1:13, 14 pages, http://www.plantmethods.com/content/1/1/13.
Herrera-Estrella et al. (1983) "Expression of chimaeric genes transferred into plant cells using a Ti-plasmid-derived vector," Nature 303:209-213.

(56) References Cited

OTHER PUBLICATIONS

Horsch et al. (1985) "A Simple and General Method for Transferring Genes into Plants," Science 227:1229-1231 with correction of authorship.
Huang, X. (1994) "On Global Sequence Alignment. Computer Applications in the Biosciences," 10(3):227-235.
Husselstein-Muller et al. (Jan. 2001) "Molecular Cloning and Expression in Yeast of 2,3-oxidosqualenetriterpenoid Cyclases from *Arabidopsis thaliana*," Plant Mol Biol. 45(1):75-92.
Kardailsky et al. (1999) "Activation Tagging of the Floral Inducer *FT*," Science 286:1962-1965, downloaded Nov. 17, 2011.
Kominato et al. (1997) "Transcription of Human ABO Histo-blood Group Genes is Dependent upon Binding of Transcription Factor CBF/NF-Y to Minisatellite Sequence," J. Biol. Chem. 272(41):25890-25898.
Krens et al. (1997) "Transgenic caraway, *Carum carvi* L.: a model species for metabolic engineering," Plant Cell Reports 17:39-43.
Kumar et al. (1996) "Potato plants expressing antisense and sense S-adenosylmethionine decarboxylase (SAMDC) transgenes show altered levels of polyamines and ethylene: antisense plants display abnormal phenotypes," The Plant J. 9(2):147-158.
Laing et al. (May 29, 2007) "The missing step of the L-galactose pathway of ascorbate biosynthesis in plants, an L-galactose guanyltransferase, increases leaf ascorbate content," PNAS USA 104(22):9534-9539.
Lew et al., (2000) "Unusual DNA Structure of the Diabetes Susceptibility Locus *IDDM2* and its Effect on Transcription by the Insulin Promoter Factor Pur-1yMAZ," PNAS 97(23):12508-12512.
Li et al. (1996) "Genetic transformation of cassava (*Manihot esculenta* Crantz)," Nature Biotechnology 14:736-740.
Li et al. (2003) "Transgenic rose lines harboring an antimicrobial protein gene, *Ace-AMP1*, demonstrate enhanced resistance to powdery mildew (*Sphaerotheca pannosa*)," Planta 218(2):226-232.
Matsuda et al. (2005) "Development of an *Agrobacterium*-mediated transformation method for pear (*Pyrus communis* L.) with leaf-section and axillary shoot-meristem explants," Plant Cell Reports 24(1):45-51.
Michelmore et al. (1987) "Transformation of lettuce (*Lactuca sativa*) mediated by *Agrobacterium tumefaciens*," Plant Cell Reports 6:439-442.
Needleman et al. (1970) "A General Method Applicable to the Search for Similarities in the Amino Acid Sequence of Two Proteins," J. Mol. Biol. 48:443-453.
Nesi et al. (Sep. 2001) "The *Arabidopsis TT2* Gene Encodes an R2R3 MYB Domain Protein that Acts as a Key Determinant for Proanthocyanidin Accumulation in Developing Seed," Plant Cell 13:2099-2114.
Niu et al. (1998) "Transgenic peppermint (*Mentha* x *piperita* L.) plants obtained by cocultivation with *Agrobacterium tumefaciens*," Plant Cell Reports 17:165-171.
Notredame et al. (2000) "T-Coffee: A Novel Method for Fast and Accurate Multiple Sequence Alignment," J. Mol. Biol. 302:205-217.
Oosumi et al. (2006) "High-efficiency transformation of the diploid strawberry (*Fragaria vesca*) for functional genomics," Planta 223(6):1219-1230, published online Dec. 1, 2005.
Ortiz et al. (1996) "Hygromycin resistance as an efficient selectable marker for wheat stable transformation," Plant Cell Reports 15:877-881.
Pena et al. (1995) "High efficiency *Agrobacterium*-mediated transformation and regeneration of citrus," Plant Science 104:183-191.
Ramesh et al. (2006) "Improved methods in *Agrobacterium*-mediated transformation of almond using positive (mannose/*pmi*) or negative (kanamycin resistance) selection-based protocols," Plant Cell Reports 25(8):821-828, published online Mar. 14, 2006.
Rice et al. (Jun. 2000) EMBOSS: The European Molecular Biology Open Software Suite, Trends in Genetics 16(6):276-277.
Rushton et al. (2008) "Tobacco Transcription Factors: Novel Insights into Transcriptional Regulation in the Solanaceae," Plant Physiol 147:280-295.
Schrott, M. (1995) "Selectable Marker and Reporter Genes," In: Gene Transfer to Plants (Potrykus, T., Spangenberg. Eds) Springer Verlag. Berline, pp. 325-336.
Song et al. (2006) "Transformation of Montmorency sour cherry (*Prunus cerasus* L.) and Gisela 6 (*P. cerasus* x *P. canescens*) cherry rootstock mediated by *Agrobacterium tumefaciens*," Plant Cell Reports 25(2):117-123, published online Dec. 21, 2005.
Takos et al. (2006) "Light-Induced Expression of a *MYB* Gene Regulates Anthocyanin Biosynthesis in Red Apples," Plant Physiology 142:1216-1232.
Tatusova et al. (1999) "BLAST 2 Sequences, a New Tool for Comparing Protein and Nucleotide Sequences", FEMS Microbiol Lett. 174:247-250.
Thompson et al. (1994) "CLUSTAL W: improving the sensitivity of progressive multiple sequence alignment through sequence weighting, position-specific gap penalties and weight matrix choice," Nucleic Acids Research 22:4673-4680.
Ubi et al. (2006) "Expression Analysis of Anthocyanin Biosynthetic Genes in Apple Skin: Effect of UV-B and Temperature," Plant Sci. 170:571-578.
Verstrepen et al. (2005) "Intragenic Tandem Repeats Generate Functional Variability," Nat. Genet. 37(9):986-990.
Wheeler et al. (2001) "Database resources of the National Center for Biotechnology Information," Nucleic Acids Research 29(1):11-16.
Xie et al. (Jan. 17, 2003) "Role of Anthocyanidin Reductase, Encoded by *BANYULS* in Plant Flavonoid Biosynthesis," Science 299:396-399, downloaded Nov. 18, 2005.
Yao et al. (1995) "Regeneration of transgenic plants from the commercial apple cultivar Royal Gala," Plant Cell Reports 14:407-412.

\* cited by examiner

|                              | 1                                                        | 50         |
|------------------------------|----------------------------------------------------------|------------|
| GP3-3_pear_promoter          | GGTGTTGAGG GGGAGTGTTG AAGATCAACA CCAGCCCAAT TGGTGTTTGT   |            |
| MdMYB10_Promoter_(short)     | .......... .......... .......... .......... ..........   |            |

|                              | 51                                                       | 100        |
|------------------------------|----------------------------------------------------------|------------|
| GP3-3_pear_promoter          | GTTGAAGTGT AATCTTGCCT TGGCCCAAGA TGGATCGAAC CCATGGACAA   |            |
| MdMYB10_Promoter_(short)     | .......... .......... .......... .......... ..........   |            |

|                              | 101                                                      | 150        |
|------------------------------|----------------------------------------------------------|------------|
| GP3-3_pear_promoter          | AGAAATATCC ATACACATGC TAGAAAATTC TAGCAAACTT CAACTTCCTC   |            |
| MdMYB10_Promoter_(short)     | .......... .......... .......... ...ATGAGCT CACCCTG...   |            |

|                              | 151                                                      | 200        |
|------------------------------|----------------------------------------------------------|------------|
| GP3-3_pear_promoter          | GAACAGTTTA GAA..GAATG GTGAGGAGAA GGCATCCACA ...CCATCTG   |            |
| MdMYB10_Promoter_(short)     | .AACACGTGG GAACCGGCCC GTTTGTAACC GACTGAGATA GGTCCGGTTC   |            |

|                              | 201                                                      | 250        |
|------------------------------|----------------------------------------------------------|------------|
| GP3-3_pear_promoter          | TATCAATTAA GAAGACTAAG TGAGAGTGAG AAGTAGGAGT AGTCTTGTGA   |            |
| MdMYB10_Promoter_(short)     | TATTTCTTAA AAACCC.AAC ACCCGCTATG TTCTATTTAT AAACGGGTCC   |            |

|                              | 251                                                      | 300        |
|------------------------------|----------------------------------------------------------|------------|
| GP3-3_pear_promoter          | GGAGTGTGAG TGGTCTAAAG TTTGTCTCTA GAAAGAGTGA GTGTCATAGC   |            |
| MdMYB10_Promoter_(short)     | GGTCTG...G TCCCTCCAAC TTTGAGCCCG GCTCGACTT. GTGCCCACTC   |            |

|                              | 301                                                      | 350        |
|------------------------------|----------------------------------------------------------|------------|
| GP3-3_pear_promoter          | TTCAAATAGT GTCTTTGAGA GTTTGTGTGC TATAATATTT TGTGAGTTAA   |            |
| MdMYB10_Promoter_(short)     | CTAAACTAAA CCATATAAAA ACCAAGAT.. ..TTCCCTTT TCTTCTTTCA   |            |

|                              | 351                                                      | 400        |
|------------------------------|----------------------------------------------------------|------------|
| GP3-3_pear_promoter          | TACAAGTAAT TGTTTACTTG TGTTGTCTCT CCAACACTTG TGTTAAAGTT   |            |
| MdMYB10_Promoter_(short)     | CACATATCAC .GTTACTTTC CAACAACAAT TCAACAATCA CAACAAA...   |            |

|                              | 401                                                      | 450        |
|------------------------------|----------------------------------------------------------|------------|
| GP3-3_pear_promoter          | GTGTACTCTA AGTTTTCCCC AACATATATC ACTTCACTAA TAAAGACAAC   |            |
| MdMYB10_Promoter_(short)     | ...TAATCAA CCA..TCAAG ATCATATATC ACGTCACTAA TAAAGACAAC   |            |

|                              | 451                                                      | 500        |
|------------------------------|----------------------------------------------------------|------------|
| GP3-3_pear_promoter          | CTTCGTAAGG GTTGCCGTAG TTCTCTACTT GAAATCCAAT TATCTAGCAT   |            |
| MdMYB10_Promoter_(short)     | CTTCACAAGG GTTGTCGTAG TTCTCTACTG GAAATCCAAT TGTCTAGCAT   |            |

|                              | 501                                                      | 550        |
|------------------------------|----------------------------------------------------------|------------|
| GP3-3_pear_promoter          | TGTAACCCTA AGTTACAGAC ACAAACATAA ACTTGAGCAA CTTCTATGCA   |            |
| MdMYB10_Promoter_(short)     | TGTAACCCTA AGTTACAGAC ACAAACATAA ACTTGAGCAA CTTCTATGCA   |            |

|                              | 551                                                      | 600        |
|------------------------------|----------------------------------------------------------|------------|
| GP3-3_pear_promoter          | TAAGAATCTA GGGTTTCAGA CTAACTCAAT GGAACCTAAC AAGAAATAAT   |            |
| MdMYB10_Promoter_(short)     | TAAGAATCTG GGGTTTTGGA CTAACTCAAC AGAACCTAAC AAGAAATAAT   |            |

|                              | 601                                                      | 650        |
|------------------------------|----------------------------------------------------------|------------|
| GP3-3_pear_promoter          | ATCC.GGACC GCT.AACGAT GCATCCAATC GAAGACAAGG TTTCGGAC.A   |            |
| MdMYB10_Promoter_(short)     | ATTCTGGACC GCTTAACG.. GAATCCAA.C GAAGACAAGG TTTCGGACCA   |            |

|                              | 651                                                      | 700        |
|------------------------------|----------------------------------------------------------|------------|
| GP3-3_pear_promoter          | CTCAACGGAA CAAATAAGGG AAAAGGATAT AAACCACTCA ACGAAGTTCA   |            |
| MdMYB10_Promoter_(short)     | CTCAACGGAA CAAATAAGGG AAAGGGATAT AAACCATTCA ACGAAATCCA   |            |

Figure 12-1

```
                        701                                                  750
    GP3-3_pear_promoter TCTCTAGAAT ACGTATAGTC .CCCAATACG GATTAACCAA GTGAGAACAT
 MdMYB10_Promoter_(short) TCTTTAGAAT ACGCATAGTC TCCCAATACG GATTAACCAA GTGAGAACAT 751                                                  800
    GP3-3_pear_promoter ACACCATCTA ATAGCATGGT CCTGCAAGAT AGATAACTAG GTAGGACCAC
 MdMYB10_Promoter_(short) ACGCCATCTG ATAGCGTGGT CCCGCAAGAC AGATAACCAA GTAGGACCAC 801                                                  850
    GP3-3_pear_promoter CGATGGTATA ATGTGACCAA GTAAGTAGTG ACCCTAAATG TAGATTAACC
 MdMYB10_Promoter_(short) CGATGGTATA ATGTGACCAA GTAAGCAGTG ACCCTAAATG TAGATTAACC 851                                                  900
    GP3-3_pear_promoter AAGTGGAGTT AAATTTAGAA TGCATATGCA CCCTACCCCC CCAAGACAGA
 MdMYB10_Promoter_(short) ACATGGAGTT AAATTA...A .......... .......... ..........

901                                                  950
    GP3-3_pear_promoter CTAACCAGGC AGAACCATAT GCATTCCCCC AATAGTGTGG TTCCTTAATG
 MdMYB10_Promoter_(short) .......... .......... .......... .......... ..........

951                                                 1000
    GP3-3_pear_promoter CAGATTGACA AGGCGGAACC ACCTATGAAA ATAATGTAAC TAGGTAGGGC
 MdMYB10_Promoter_(short) ........CA AGGCTGAACC ACCTATGAAA ATAATGTAA. ..........

1001                                                 1050
    GP3-3_pear_promoter CCGACGAATA TCTATTGCCT GAAATCTTAG GAGAGAATTC TTGCTCTAGG
 MdMYB10_Promoter_(short) .......... ......GCCT GAAATCTTAG GAGAGAATTC TTGCTCTAGG 1051                                                 1100
    GP3-3_pear_promoter GGACAAATGA TTTTCGTATG CCTAAGTATT TTTTATTTAG TGACAGTAAA
 MdMYB10_Promoter_(short) GGACAAATGA TTTTCGTATG CCTAAGTGTT TTTT...TAG TGACAGTAAA 1101                                                 1150
    GP3-3_pear_promoter CTAAGATTTG AGTACAGAGA CATTAACTGA GATTGACTCT TGTGAAAGCT
 MdMYB10_Promoter_(short) CTAAGATTTG AGTACAGAGA CATTAACTGA GATTGACTCT TGTGAAAGCT 1151                                                 1200
    GP3-3_pear_promoter TAGTGAGTTG AAGCACTTAG GCCAATTATA TTGAGCAATG TGTTAGGTGT
 MdMYB10_Promoter_(short) TAGTGAGTTG AAGCACGTAG GCCAATTATA TTGAGCAATG TGTTAGGTGT 1201                                                 1250
    GP3-3_pear_promoter AGCGTCTAAA CTTCCGTAGG AGTTTTTTAC AACAAGATAG TGGGGGTGCC
 MdMYB10_Promoter_(short) AGCGTCTAAA CTTCCGTAGG AGTTTTGTAC AGCAATATAG TGGGGGTGCC 1251                                                 1300
    GP3-3_pear_promoter GCAAAATGCA GACAGTAGCA ATAAATTACG GGCTAGGATT ATCTCCCCTC
 MdMYB10_Promoter_(short) GCAAAATGCA GACAGTAGCA ATAAATTACG GGCTAGGATT TTCTCCTCTT 1301                                                 1350
    GP3-3_pear_promoter GTTTTTTGT TCCATTCCAT CCCTTCCTCT CACATTCTCT ATTTTGTCTT
 MdMYB10_Promoter_(short) TTTTTTTCGT TCCATTCCAT CCATTCCTCT CACATTTTTT ATTTTGTCTT 1351                                                 1400
    GP3-3_pear_promoter TCTTTTTCTA AAAAAAATTA ATATAAGATG TTGATATAGC TTAACCGGGA
 MdMYB10_Promoter_(short) TCTCTTTCTA TAAAAAATTA ATATAAGATG TTAATGTAAC TTGACCGTGA 1401                                                 1450
    GP3-3_pear_promoter CCGTTCAAAT AAGAGGGCAA GCAACAAGAC GAAAAAAAAA ACACAGGAAG
 MdMYB10_Promoter_(short) CTATTCAAAT AGGAGGGGAA TGAAGAAGAG GGAAAAAAA. ......GG...

1451                                                 1500
    GP3-3_pear_promoter GAAGAAGAGG AAAAAAAAAA AAAAGAGAG GGAAGAGATT TTACTTTATA
```

Figure 12-2

```
                         1501                                                   1550
   GP3-3_pear_promoter   AATTACAAGC AGACACTTTT TGTTTTTTTT TTTTTTTGAC AAGGAGAAGC
MdMYB10_Promoter_(short) AATTACAAGC AAACACTTT. .....TTTTT TTTTTTTGAC AAGCAGAAGC 1551                                                   1600
   GP3-3_pear_promoter   AAACAAACAC TTGAAAAAGC AGCGAAAGCA GGCTAAAGGT ATCTTATGGT
MdMYB10_Promoter_(short) AAACAAACAC TTGAAAAAGC AGCGAAAGCA TGATAAAGGT ATCTTATGGT 1601                                                   1650
   GP3-3_pear_promoter   GGTCAAAGAT GTGTGTTGTA ACTAGTTACA CGATTCTGCC TTCACATTCA
MdMYB10_Promoter_(short) GGTCAAAGAT GTGTGTTGTA ACTAGTTACA CGATTCTGCA TTCACATTCA 1651                                                   1700
   GP3-3_pear_promoter   TAGAATGTGC TTTTGAATAT TATATTACAG CTAGAGAATT TGATGTCTTA
MdMYB10_Promoter_(short) TAGAATGTGC TTTTGAATAT TATATTACAG CTAGAGAATT TTATGCCCTG 1701                                                   1750
   GP3-3_pear_promoter   GCA....... .........A TGTTGTCGTG CAGAAATGTC AGCTTTTCTA
MdMYB10_Promoter_(short) GGATTGATTT CCCTTGTCAA TGTTGTCGTG CAGAAATGTT AGCTTTTCTA 1751                                                   1800
   GP3-3_pear_promoter   TATATAGCGT GTGTGT.... ......ATTT CACAAGTTAG ACCGGTAGCT
MdMYB10_Promoter_(short) TATATCGAGT GTGTGTGTCT CTGTGTATTT CACAAGTTAG ACTGGTAGCT 1801                                                   1850
   GP3-3_pear_promoter   AATAACAACT GTTGAAATGT TTCAAACGTG TCACTGTTTG CTTCTGTGGA
MdMYB10_Promoter_(short) AATAACAACT GTTGGAATGT TTTAAACTTG TCAGTGTTTG CTTCTGTGGA 1851                                                   1900
   GP3-3_pear_promoter   TATCAGACAT GCACGTCACT GGCCTTGGAA GATTAATTAG TCCGATGGTA
MdMYB10_Promoter_(short) TATCAGACAT GCACGTCACT GGCCTTGTAA GATTAATTAG GCCGATGGTA 1901                                                   1950
   GP3-3_pear_promoter   TCCATAGCGT TAACGTCATG GCAAACACAC TCTAAATATA TATATATATA
MdMYB10_Promoter_(short) TCCATAGCGT TAATGTCATG GCAAACACAC TCTAATTATA TAT...A....

1951                                                   2000
   GP3-3_pear_promoter   TAATGGTAGC TAGGTGTCTT TCTGGAGT.. ATGAAGTGGG TAGCAGGCAA
MdMYB10_Promoter_(short) ..ATGGTAGC TAGGTGTCTT TCTGGAGTGT ATGAAGTGGG TAGCAGGCAA 2001                               2038
   GP3-3_pear_promoter   AAGATAAGCT AAGTTTAGCT GCTAGCAGAT ACGAGATG
MdMYB10_Promoter_(short) AAGAATAGCT AAGCTTAGCT GCTAGCAGAT AAGAGATG
```

Figure 12-3

CHIMERIC PROMOTERS COMPRISING MYB10 REPEAT ELEMENT AND METHODS FOR REGULATING PLANT GENE EXPRESSION

TECHNICAL FIELD

The present invention relates to polynucleotides for regulating gene expression in plants, and uses thereof.

BACKGROUND ART

An important for goal for agriculture is to produce plants with beneficial agronomic traits. Recent advances in genetic manipulation provide the tools to transform plants with polynucleotide sequences of interest and to express such sequences within the transformed plants. This has led to the development of plants capable of expressing pharmaceuticals and other chemicals, plants with increased pest resistance, increased stress tolerance and many other beneficial traits.

It is often desirable to control expression of a polynucleotide of interest, in a particular tissue, at a particular developmental stage, or under particular conditions, in which the polynucleotide is not normally expressed. The polynucleotide of interest may encode a protein or alternatively may be intended to effect silencing of a corresponding target gene.

Plant promoter sequences are useful in genetic manipulation for directing expression of polynucleotides in transgenic plants. To achieve this, a genetic construct is often introduced into a plant cell or plant. Typically such constructs include a plant promoter operably linked to the polynucleotide sequence of interest. Such a promoter need not normally be associated with the gene of interest. Once transformed, the promoter controls expression of the operably linked polynucleotide of interest thus leading to the desired transgene expression and resulting desired phenotypic characteristics in the plant.

Promoters used in genetic manipulation are typically derived from the 5' un-transcribed region of genes and contain regulatory elements that are necessary to control expression of the operably linked polynucleotide. Promoters useful for plant biotechnology can be classified depending on when and where they direct expression. For example promoters may be tissue specific or constitutive (capable of transcribing sequences in multiple tissues). Other classes of promoters include inducible promoters that can be triggered by external stimuli such as environmental and chemical stimuli.

Often a relatively high level of expression of the transformed sequence of interest is desirable. This is often achieved through use of viral promoter sequences such as the Cauliflower Mosaic Virus 35S promoter. In some circumstances it may be more preferable to use a plant derived promoter rather than a promoter derived from a microorganism. It may also be preferable in some circumstances to use a promoter derived from, or produced from sequences derived from, the species to be transformed.

It would be beneficial to have a variety of promoters available in order to ensure that transgenes are transcribed at an appropriate level in the right tissues, and at an appropriate stage of growth or development.

The apple (*Malus* species) is a major fruit species grown in New Zealand and other temperate climates throughout the world. Valuable traits that may be improved by genetic manipulation of apple include: fruit flavour, fruit colour, content of health promoting components (such as anthocyanins and flavanoids) in fruit, stress tolerance/resistance, pest tolerance/resistance and disease tolerance/resistance.

Genetic manipulation of such traits in apple, and these and other traits in other species, is limited by the availability of promoters capable of appropriately controlling the expression of genes of interest.

It is therefore an object of the present invention to provide a promoter useful for controlling gene expression in apple and other plants and/or at least to provide a useful choice.

SUMMARY OF THE INVENTION

In the first aspect the invention provides a method for producing a chimeric promoter polynucleotide capable of controlling transcription of an operably linked polynucleotide in a plant cell or plant, wherein the method comprises combining:
a) at least one sequence motif comprising a sequence with at least 70% identity to SEQ ID NO:1, 11 or 12, and
b) another polynucleotide sequence.

In a preferred embodiment the method comprises combining:
a) at least two sequence motifs, each comprising a sequence with at least 70% identity to any one of SEQ ID NO:1, 11 or 12, and
b) another polynucleotide sequence.

The chimeric promoter polynucleotide more preferably produced by combining:
a) at least three, more preferably at least four, more preferably at least five, more preferably at least six, and most preferably at least seven sequence motifs, each comprising a sequence with at least 70% identity to any one of SEQ ID NO: 1, 11 or 12, and
b) another polynucleotide sequence.

Preferably at least one of the sequence motifs in a) comprises a sequence with at least 70% identity to the sequence of SEQ ID NO: 1.

Preferably at least one motif in a) comprises the sequence of SEQ ID NO: 41.

Preferably at least one motif in a) comprises the sequence of SEQ ID NO: 42.

In one embodiment at least one sequence motif in a) comprises the sequence of SEQ ID NO: 1.

In another embodiment at least one sequence motif in a) comprises the sequence of SEQ ID NO: 11.

In another embodiment at least one sequence motif in a) comprises the sequence of SEQ ID NO: 12.

The chimeric promoter may comprise several of the motifs in a) as defined above. The motifs within the promoter may all be the same, or may be a combination of different motifs as defined above.

In another embodiment at least one of the sequence motifs is interrupted by at least one of the other sequence motifs.

In a further embodiment the sequence motif in a) is part of a promoter polynucleotide sequence that naturally occurs in a plant.

In a further embodiment the polynucleotide in b) is a promoter polynucleotide sequence.

In a further embodiment the polynucleotide in b) is a promoter polynucleotide sequence that naturally occurs in a plant.

In a preferred embodiment both the sequence motif in a) and the polynucleotide, or promoter polynucleotide in b) naturally occur in plants Preferably the sequence motif in a) and the polynucleotide in b) naturally occur in the same species, or interfertile species.

Preferably the sequence motif in a) and the polynucleotide in b) naturally occur in the same promoter.

In this embodiment a further copy, or copies, of a motif with at least 70% identity to SEQ ID NO:1, 11 or 12, that is present in a naturally occurring promoter polynucleotide, may be added to the naturally occurring promoter polynucleotide to produce the chimeric promoter polynucleotide.

In an alternative embodiment one or more motifs with at least 70% identity to SEQ ID NO:1, 11 or 12, that are naturally occurring in plant promoters, may be added to a different naturally occurring promoter.

The motif or motifs with at least 70% identity to SEQ ID NO:1, 11 or 12, may be naturally occurring in different species, or different promoters, and may be combined with a promoter from one of the same species, or from a different species.

In one embodiment the naturally occurring promoter polynucleotide in b) comprises a sequence with at least 70% identity to SEQ ID NO:13.

In a further embodiment the naturally occurring promoter polynucleotide comprises the sequence of SEQ ID NO:13.

In one embodiment the chimeric promoter is produced by combining:
a) the sequence of SEQ ID NO:14, and
b) the sequence of SEQ ID NO:8.

In one embodiment the chimeric promoter is produced by combining:
a) the sequence of SEQ ID NO:14, and
b) the sequence of SEQ ID NO:13.

In one embodiment the chimeric promoter is produced by combining:
a) the sequence of SEQ ID NO:14, and
b) the sequence of SEQ ID NO:36.

In one embodiment the chimeric promoter is produced by combining:
a) the sequence of SEQ ID NO:14, and
b) the sequence of SEQ ID NO:38.

In a further embodiment the chimeric promoter polynucleotide comprises a sequence with at least 70% identity to SEQ ID NO:15.

In a further embodiment the chimeric promoter polynucleotide comprises the sequence of SEQ ID NO:15.

In a further embodiment the chimeric promoter polynucleotide comprises a sequence with at least 70% identity to SEQ ID NO:37.

In a further embodiment the chimeric promoter polynucleotide comprises the sequence of SEQ ID NO:37.

In a further embodiment the chimeric promoter polynucleotide comprises a sequence with at least 70% identity to SEQ ID NO:39.

In a further embodiment the chimeric promoter polynucleotide comprises the sequence of SEQ ID NO:39.

In a further embodiment the chimeric promoter polynucleotide comprises a sequence with at least 70% identity to SEQ ID NO:40.

In a further embodiment the chimeric promoter polynucleotide comprises the sequence of SEQ ID NO:40.

In a further aspect the invention provides a chimeric promoter produced by the method of the invention.

In a further aspect the invention provides a chimeric promoter polynucleotide capable of controlling transcription of an operably linked polynucleotide in a plant cell or plant, wherein the promoter polynucleotide comprises:

a) at least one sequence motif comprising a sequence with at least 70% identity to SEQ ID NO:1, 11 or 12
b) another polynucleotide sequence.

In a preferred embodiment the chimeric promoter polynucleotide comprises at least two sequence motifs comprising a sequence with at least 70% identity to SEQ ID NO:1, 11 or 12.

The chimeric promoter polynucleotide more preferably comprises at least three, more preferably at least four, more preferably at least five, more preferably at least six, and most preferably at least seven sequence motifs comprising a sequence with at least 70% identity to SEQ ID NO: 1, 11 or 12.

Preferably at least one of the sequence motifs comprises a sequence with at least 70% identity to the sequence of SEQ ID NO: 1.

Preferably at least one motif in a) comprises the sequence of SEQ ID NO: 41.

Preferably at least one motif in a) comprises the sequence of SEQ ID NO: 42.

In one embodiment at least one sequence motif comprises the sequence of SEQ ID NO: 1.

In another embodiment at least one sequence motif comprises the sequence of SEQ ID NO: 11.

In another embodiment at least one sequence motif comprises the sequence of SEQ ID NO: 12.

The chimeric promoter may comprise several of the motifs in a) as defined above. The motifs within the promoter may all be the same, or may be a combination of different motifs as defined above.

In another embodiment at least one of the sequence motifs is interrupted by at least one of the other sequence motifs.

In a further embodiment the sequence motif in a) is part of a promoter polynucleotide sequence that naturally occurs in a plant.

In a further embodiment the polynucleotide in b) is a promoter polynucleotide sequence.

In a further embodiment the polynucleotide in b) is a promoter polynucleotide sequence that naturally occurs in a plant.

In a preferred embodiment both the sequence motif in a) and the polynucleotide in b) naturally occur in plants Preferably the sequence motif in a) and the polynucleotide in b) naturally occur in the same species, or interfertile species.

Preferably the sequence motif in a) and the polynucleotide in b) naturally occur in the same promoter.

In this embodiment the chimeric promoter may comprise the naturally occurring promoter with an additional inserted copy, or copies, of a motif with at least 70% identity to SEQ ID NO: 1, 12 or 13 that is present in the naturally occurring promoter polynucleotide.

In an alternative embodiment the chimeric promoter may comprise a naturally occurring promoter, with an additional inserted copy or copies of a motif with at least 70% identity to SEQ ID NO: 1, 12 or 13 that is not present in the naturally occurring promoter polynucleotide.

The motif or motifs comprising a sequence with at least 70% identity to SEQ ID NO:1, 11 or 12, may be naturally occurring in different species, or different promoters, and may have been combined with a promoter from one of the same species, or from a different species.

In one embodiment the naturally occurring promoter polynucleotide comprises a sequence with at least 70% identity to SEQ ID NO:13.

In a further embodiment the naturally occurring promoter polynucleotide comprises the sequence of SEQ ID NO:13.

In one embodiment the chimeric promoter comprises:
a) the sequence of SEQ ID NO:14, combined with
b) the sequence of SEQ ID NO:8.

In one embodiment the chimeric promoter comprises:
a) the sequence of SEQ ID NO:14, combined with
b) the sequence of SEQ ID NO:13.

In one embodiment the chimeric promoter comprises:
a) the sequence of SEQ ID NO:14, combined with
b) the sequence of SEQ ID NO:36.

In one embodiment the chimeric promoter comprises:
a) the sequence of SEQ ID NO:14, combined with
b) the sequence of SEQ ID NO:38.

In a further embodiment the chimeric promoter polynucleotide comprises a sequence with at least 70% identity to SEQ ID NO:15.

In a further embodiment the chimeric promoter polynucleotide comprises the sequence of SEQ ID NO:15.

In a further embodiment the chimeric promoter polynucleotide comprises a sequence with at least 70% identity to SEQ ID NO:37.

In a further embodiment the chimeric promoter polynucleotide comprises the sequence of SEQ ID NO:37.

In a further embodiment the chimeric promoter polynucleotide comprises a sequence with at least 70% identity to SEQ ID NO:39.

In a further embodiment the chimeric promoter polynucleotide comprises the sequence of SEQ ID NO:39.

In a further embodiment the chimeric promoter polynucleotide comprises a sequence with at least 70% identity to SEQ ID NO:40.

In a further embodiment the chimeric promoter polynucleotide comprises the sequence of SEQ ID NO:40.

In a further embodiment the chimeric promoter polynucleotide is modulated by a MYB transcription factor.

In a further embodiment the chimeric promoter polynucleotide is positively modulated, or activated, or up-regulated by the MYB transcription factor.

Preferably the MYB transcription factor comprises an R2R3 DNA binding domain.

Preferably the MYB transcription factor comprises a sequence with at least 70% identity to the sequence of SEQ ID NO: 6.

Preferably the MYB transcription factor comprises the sequence of SEQ ID NO: 6.

Preferably the MYB transcription factor comprises a sequence with at least 70% identity to the sequence of SEQ ID NO: 17.

Preferably the MYB transcription factor comprises the sequence of SEQ ID NO: 17.

Preferably the MYB transcription factor comprises a sequence with at least 70% identity to the sequence of SEQ ID NO: 32.

Preferably the MYB transcription factor comprises the sequence of SEQ ID NO: 32.

Preferably the MYB transcription factor comprises a sequence with at least 70% identity to the sequence of SEQ ID NO: 34.

Preferably the MYB transcription factor comprises the sequence of SEQ ID NO: 34.

Preferably the chimeric promoter polynucleotide is up-regulated by the gene product of the gene with which at least one of the sequence motifs of the chimeric promoter polynucleotide is endogenously associated.

Preferably at least one of the sequence motifs of the chimeric promoter polynucleotide in its natural environment is endogenously associated with the MYB transcription factor.

Preferably the chimeric promoter is positively regulated by the MYB transcription factor.

Preferably the chimeric promoter polynucleotide is capable of controlling transcription of an operably linked polynucleotide sequence constitutively in substantially all tissues of a plant.

More preferably the promoter polynucleotide is capable of controlling transcription of an operably linked polynucleotide sequence in any plant, plant cell, or plant tissue in which the MYB transcription factor is expressed.

The MYB transcription factor may be naturally expressed in the plant or may be expressed in the plant through genetic manipulation of the plant.

In a further aspect the invention provides a genetic construct comprising a chimeric promoter polynucleotide of the invention.

In one embodiment the chimeric promoter polynucleotide is operably linked to a polynucleotide sequence to be expressed.

In a further aspect the invention provides a vector comprising a genetic construct of the invention.

In a further aspect the invention provides a host cell transformed with the chimeric promoter polynucleotide of the invention.

In a further aspect the invention provides a plant cell or plant transformed with the chimeric promoter polynucleotide of the invention.

In a further aspect the invention provides a plant cell or plant transformed with a genetic construct of the invention.

In one embodiment the plant cell or plant is also transformed with a polynucleotide or genetic construct for expressing a MYB transcription factor that modulates expression of the chimeric promoter polynucleotide of the invention.

In a further embodiment the plant cell or plant naturally expresses the MYB transcription factor.

In a further embodiment the MYB transcription factor comprises an amino acid sequence with at least 70% identity to the sequence of any one of SEQ ID NO: 6, 17, 32 and 34.

Preferably the MYB transcription factor comprises the sequence of any one of SEQ ID NO: 6, 17, 32 and 34.

In a further embodiment the MYB transcription factor comprises an amino acid sequence with at least 70% identity to the sequence of SEQ ID NO: 6.

Preferably the MYB transcription factor comprises the sequence of SEQ ID NO: 6.

In a further embodiment the MYB transcription factor comprises an amino acid sequence with at least 70% identity to the sequence of SEQ ID NO: 17.

Preferably the MYB transcription factor comprises the sequence of SEQ ID NO: 17.

In a further embodiment the MYB transcription factor comprises an amino acid sequence with at least 70% identity to the sequence of SEQ ID NO: 32.

Preferably the MYB transcription factor comprises the sequence of SEQ ID NO: 32.

In a further embodiment the MYB transcription factor comprises an amino acid sequence with at least 70% identity to the sequence of SEQ ID NO: 34.

Preferably the MYB transcription factor comprises the sequence of SEQ ID NO: 34.

In a further aspect the invention provides a method for producing a plant cell or plant with modified expression of at least one polynucleotide, the method comprising transformation of the plant cell or plant with a chimeric promoter polynucleotide of the invention In one embodiment the plant cell or plant is transformed with a genetic construct of the invention.

In a further embodiment the plant cell or plant is also transformed with a polynucleotide or genetic construct capable of expressing a MYB transcription factor that modulates expression of the chimeric promoter polynucleotide of the invention.

In a further embodiment the plant cell or plant naturally expresses the MYB transcription factor.

In a further embodiment the MYB transcription factor comprises an amino acid sequence with at least 70% identity to the sequence of any one of SEQ ID NO: 6, 17, 32 and 34.

Preferably the MYB transcription factor comprises the sequence of any one of SEQ ID NO: 6, 17, 32 and 34.

In a further embodiment the MYB transcription factor comprises a sequence with at least 70% identity to the sequence of SEQ ID NO: 6.

Preferably the MYB transcription factor comprises the sequence of SEQ ID NO: 6.

In a further embodiment the MYB transcription factor comprises a sequence with at least 70% identity to the sequence of SEQ ID NO: 17.

Preferably the MYB transcription factor comprises the sequence of SEQ ID NO: 17.

In a further embodiment the MYB transcription factor comprises a sequence with at least 70% identity to the sequence of SEQ ID NO: 32.

Preferably the MYB transcription factor comprises the sequence of SEQ ID NO: 32.

In a further embodiment the MYB transcription factor comprises a sequence with at least 70% identity to the sequence of SEQ ID NO: 34.

Preferably the MYB transcription factor comprises the sequence of SEQ ID NO: 34.

It will be appreciated by those skilled in the art that, the chimeric promoter polynucleotide of the invention may be transformed into the plant to control expression of a polynucleotide that is operably linked to the promoter prior to transformation.

Alternatively the promoter polynucleotide may be transformed into the genome of the plant without an operably linked polynucleotide, but the promoter may control expression of an endogenous polynucleotide, typically adjacent to the insert site, and typically, to the 3' end of the inserted promoter polynucleotide.

In a further aspect of the invention provides a method for producing a plant cell or plant with a modified phenotype, the method comprising the stable incorporation into the genome of the plant, of a chimeric promoter polynucleotide of the invention In one embodiment the plant cell or plant is transformed within a genetic construct of the invention.

In a further embodiment the plant cell or plant is also transformed with a genetic construct for expressing a MYB transcription factor that modulates expression of the chimeric promoter polynucleotide of the invention.

In a further embodiment the plant cell or plant naturally expresses the MYB transcription factor.

In a further embodiment the MYB transcription factor comprises an amino acid sequence with at least 70% identity to the sequence of any one of SEQ ID NO: 6, 17, 32 and 34.

Preferably the MYB transcription factor comprises the sequence of any one of SEQ ID NO: 6, 17, 32 and 34.

In a further embodiment the MYB transcription factor comprises a sequence with at least 70% identity to the sequence of SEQ ID NO: 6.

Preferably the MYB transcription factor comprises the sequence of SEQ ID NO: 6.

In a further embodiment the MYB transcription factor comprises a sequence with at least 70% identity to the sequence of SEQ ID NO: 17.

Preferably the MYB transcription factor comprises the sequence of SEQ ID NO: 17.

In a further embodiment the MYB transcription factor comprises a sequence with at least 70% identity to the sequence of SEQ ID NO: 32.

Preferably the MYB transcription factor comprises the sequence of SEQ ID NO: 32.

In a further embodiment the MYB transcription factor comprises a sequence with at least 70% identity to the sequence of SEQ ID NO: 34.

Preferably the MYB transcription factor comprises the sequence of SEQ ID NO: 34.

In a further aspect the invention provides a plant cell or plant produced by a method of the invention.

In a further aspect the invention provides a seed, propagule, progeny, part, fruit or harvested material of a plant, of the invention.

Preferably the seed, propagule, progeny, part, fruit or harvested material of the plant comprises a chimeric promoter polynucleotide of the invention.

The naturally occurring sequences that may be used to produce the chimeric promoter polynucleotide of the invention may be derived from any species.

In one embodiment the naturally occurring sequence, is derived from a plant species.

In a further embodiment the naturally occurring sequence, is derived from a gymnosperm plant species.

In a further embodiment the naturally occurring sequence, is derived from an angiosperm plant species.

In a further embodiment the naturally occurring sequence, is derived from a from dicotyledonous plant species.

In a further embodiment the naturally occurring sequence, is derived from a monocotyledonous plant species.

The polypeptide encoded by the polynucleotide to be expressed in a construct of the invention, may be derived from any species and/or may be produced synthetically or recombinantly.

In one embodiment the polypeptide is derived from a plant species.

In a further embodiment the polypeptide is derived from a gymnosperm plant species.

In a further embodiment the polypeptide is derived from an angiosperm plant species.

In a further embodiment the polypeptide is derived from a from dicotyledonous plant species.

In a further embodiment the polypeptide is derived from a monocotyledonous plant species.

The MYB transcription factor that regulates the chimeric promoter polynucleotide of the invention may be derived from any species and/or may be produced synthetically or recombinantly.

In one embodiment the MYB transcription factor, is derived from a plant species.

In a further embodiment the MYB transcription factor, is derived from a gymnosperm plant species.

In a further embodiment the MYB transcription factor, is derived from an angiosperm plant species.

In a further embodiment the MYB transcription factor, is derived from a from dicotyledonous plant species.

In a further embodiment the MYB transcription factor, is derived from a monocotyledonous plant species.

The plant cells and plants, of the invention, or produced by the methods of the invention, may be derived from any species.

In one embodiment the plant cell or plant, is derived from a gymnosperm plant species.

In a further embodiment the plant cell or plant, is derived from an angiosperm plant species.

In a further embodiment the plant cell or plant, is derived from a from dicotyledonous plant species.

In a further embodiment the plant cell or plant, is derived from a monocotyledonous plant species.

Preferred plant species (from which the naturally occurring sequence and variants, polypeptides and variants, MYB transcription factor and variants, and plant cells and plants may be derived) include fruit plant species selected from a group comprising but not limited to the following genera: *Malus, Pyrus Prunis, Rubus, Rosa, Fragaria, Actinidia, Cydonia, Citrus*, and *Vaccinium*.

Particularly preferred fruit plant species are: *Malus domestica, Pyrus communis, Actidinia deliciosa, A. chinensis, A. eriantha, A. arguta* and hybrids of the four *Actinidia* species, *Fragaria ananassa* and *Prunis persica*.

Preferred plants also include vegetable plant species selected from a group comprising but not limited to the following genera: *Brassica, Lycopersicon* and *Solanum*.

Particularly preferred vegetable plant species are: *Lycopersicon esculentum* and *Solanum tuberosum*.

Preferred plants also include crop plant species selected from a group comprising but not limited to the following genera: *Glycine, Zea, Hordeum* and *Oryza*.

Particularly preferred crop plant species include *Glycine max, Zea mays* and *Oryza sativa*.

Preferred plants also include those of the Rosaceae family.

Preferred Rosaceae genera include *Exochorda, Maddenia, Oemleria, Osmaronia, Prinsepia, Prunus, Maloideae, Amelanchier, Aria, Aronia, Chaenomeles, Chamaemespilus, Cormus, Cotoneaster, CrataegusOsmaronia, Prinsepia, Prunus, Maloideae, Amelanchier, Aria, Aronia, Chaenomeles, Chamaemespilus, Cormus, Cotoneaster, Crataegu, Cydonia, Dichotomanthes, Docynia, Docyniopsis, Eriobotrya, Eriolobus, Heteromeles, Kageneckia, Lindleya, Malacomeles, Malus, Mespilus, Osteomeles, Peraphyllum, Photinia, Pseudocydonia, Pyracantha, Pyrus, Rhaphiolepis, Sorbus, Stranvaesia, Torminalis, Vauquelinia, Rosoideae, Acaena, Acomastylis, Agrimonia, Alchemilla, Aphanes, Aremonia, Bencomia, Chamaebatia, Cliffortia, Coluria, Cowania, Dalibarda, Dendriopoterium, Dryas, Duchesnea, Erythrocoma, Fallugia, Filipendula, Fragaria, Geum, Hagenia, Horkelia, Ivesia, Kerria, Leucosidea, Marcetella, Margyricarpus, Novosieversia, Oncostylus, Polylepis, Potentilla, Rosa, Rubus, Sanguisorba, Sarcopoterium, Sibbaldia, Sieversia, Taihangia, Tetraglochin, Waldsteinia, Rosaceae incertae sedis, Adenostoma, Aruncus, Cercocarpus, Chamaebatiaria, Chamaerhodos, Gillenia, Holodiscus, Lyonothamnus, Neillia, Neviusia, Physocarpus, Purshia, Rhodotypos, Sorbaria, Spiraea* and *Stephanandra*.

Preferred Rosaceae species include *Exochorda giraldii, Exochorda racemosa, Exochorda, Exochorda giraldii, Exochorda racemosa, Exochorda serratifolia, Maddenia hypoleuca, Oemleria cerasiformis, Osmaronia cerasiformis, Prinsepia sinensis, Prinsepia uniflora, Prunus alleghaniensis, Prunus americana, Prunus andersonii, Prunus angustifolia, Prunus apetala, Prunus argentea, Prunus armeniaca, Prunus avium, Prunus bifrons, Prunus brigantina, Prunus bucharica, Prunus buergeriana, Prunus campanulata, Prunus caroliniana, Prunus cerasifera, Prunus cerasus, Prunus choreiana, Prunus cocomilia, Prunus cyclamina, Prunus davidiana, Prunus debilis, Prunus domestica, Prunus dulcis, Prunus emarginata, Prunus fasciculata, Prunus ferganensis, Prunus fordiana, Prunus fremontii, Prunus fruticosa, Prunus geniculata, Prunus glandulosa, Prunus gracilis, Prunus grayana, Prunus hortulana, Prunus ilicifolia, Prunus incisa, Prunus jacquemontii, Prunus japonica, Prunus kuramica, Prunus laurocerasus, Prunus leveilleana, Prunus lusitanica, Prunus maackii, Prunus mahaleb, Prunus mandshurica, Prunus maritima, Prunus maximowiczii, Prunus mexicana, Prunus microcarpa, Prunus mira, Prunus mume, Prunus munsoniana, Prunus nigra, Prunus nipponica, Prunus padus, Prunus pensylvanica, Prunus persica, Prunus petunnikowii, Prunus prostrata, Prunus pseudocerasus, Prunus pumila, Prunus rivularis, Prunus salicina, Prunus sargentii, Prunus sellowii, Prunus serotina, Prunus serrulata, Prunus sibirica, Prunus simonii, Prunus spinosa, Prunus spinulosa, Prunus subcordata, Prunus subhirtella, Prunus takesimensis, Prunus tenella, Prunus texana, Prunus tomentosa, Prunus tschonoskii, Prunus umbellata, Prunus verecunda, Prunus virginiana, Prunus webbii, Prunus×yedoensis, Prunus zippeliana, Prunus* sp. BSP-2004-1, *Prunus* sp. BSP-2004-2, *Prunus* sp. EB-2002, *Amelanchier alnifolia, Amelanchier arborea, Amelanchier asiatica, Amelanchier bartramiana, Amelanchier canadensis, Amelanchier cusickii, Amelanchier fernaldii, Amelanchier florida, Amelanchier humilis, Amelanchier intermedia, Amelanchier laevis, Amelanchier lucida, Amelanchier nantucketensis, Amelanchier pumila, Amelanchier quinti-martii, Amelanchier sanguinea, Amelanchier stolonifera, Amelanchier utahensis, Amelanchier wiegandii, Amelanchier×neglecta, Amelanchier bartramiana× Amelanchier* sp. 'dentata', *Amelanchier* sp. 'dentata', *Amelanchier* sp. 'erecta', *Amelanchier* sp. 'erecta'×*Amelanchier laevis, Amelanchier* sp. 'serotina', *Aria alnifolia, Aronia prunifolia, Chaenomeles cathayensis, Chaenomeles speciosa, Chamaemespilus alpina, Cormus domestica, Cotoneaster apiculatus, Cotoneaster lacteus, Cotoneaster pannosus, Crataegus azarolus, Crataegus columbiana, Crataegus crus-galli, Crataegus curvisepala, Crataegus laevigata, Crataegus mollis, Crataegus monogyna, Crataegus nigra, Crataegus rivularis, Crataegus sinaica, Cydonia oblonga, Dichotomanthes tristaniicarpa, Docynia delavayi, Docyniopsis tschonoskii, Eriobotrya japonica, Eriobotrya prinoides, Eriolobus trilobatus, Heteromeles arbutifolia, Kageneckia angustifolia, Kageneckia oblonga, Lindleya mespiloides, Malacomeles denticulata, Malus angustifolia, Malus asiatica, Malus baccata, Malus coronaria, Malus doumeri, Malus florentina, Malus floribunda, Malus fusca, Malus halliana, Malus honanensis, Malus hupehensis, Malus ioensis, Malus kansuensis, Malus mandshurica, Malus micromalus, Malus niedzwetzkyana, Malus ombrophilia, Malus orientalis, Malus prattii, Malus prunifolia, Malus pumila, Malus sargentii, Malus sieboldii, Malus sieversii, Malus sylvestris, Malus toringoides, Malus transitoria, Malus trilobata, Malus tschonoskii, Malus×domestica, Malus×domestica×Malus sieversii, Malus×domestica×Pyrus communis, Malus xiaojinensis, Malus yunnanensis, Malus* sp., *Mespilus germanica, Osteomeles anthyllidifolia, Osteomeles schwerinae, Peraphyllum ramosissimum, Photinia fraseri, Photinia pyrifolia, Photinia serrulata, Photinia villosa, Pseudocydonia sinensis, Pyracantha coccinea, Pyracantha fortuneana, Pyrus calleryana, Pyrus caucasica, Pyrus communis, Pyrus elaeagrifolia, Pyrus hybrid cultivar, Pyrus pyrifolia, Pyrus salicifolia, Pyrus ussuriensis, Pyrus× bretschneideri, Rhaphiolepis indica, Sorbus americana, Sorbus aria, Sorbus aucuparia, Sorbus californica, Sorbus com-*

*mixta, Sorbus hupehensis, Sorbus scopulina, Sorbus sibirica, Sorbus torminalis, Stranvaesia davidiana, Torminalis clusii, Vauquelinia californica, Vauquelinia corymbosa, Acaena anserinifolia, Acaena argentea, Acaena caesiiglauca, Acaena cylindristachya, Acaena digitata, Acaena echinata, Acaena elongata, Acaena eupatoria, Acaena fissistipula, Acaena inermis, Acaena laevigata, Acaena latebrosa, Acaena lucida, Acaena macrocephala, Acaena magellanica, Acaena masafuerana, Acaena montana, Acaena multifida, Acaena novaezelandiae, Acaena ovalifolia, Acaena pinnatifida, Acaena splendens, Acaena subincisa, Acaena×anserovina, Acomastylis elata, Acomastylis rossii, Acomastylis sikkimensis, Agrimonia eupatoria, Agrimonia nipponica, Agrimonia parviflora, Agrimonia pilosa, Alchemilla alpina, Alchemilla erythropoda, Alchemilla japonica, Alchemilla mollis, Alchemilla vulgaris, Aphanes arvensis, Aremonia agrimonioides, Bencomia brachystachya, Bencomia caudata, Bencomia exstipulata, Bencomia sphaerocarpa, Chamaebatia foliolosa, Cliffortia burmeana, Cliffortia cuneata, Cliffortia dentata, Cliffortia graminea, Cliffortia heterophylla, Cliffortia nitidula, Cliffortia odorata, Cliffortia ruscifolia, Cliffortia sericea, Coluria elegans, Coluria geoides, Cowania stansburiana, Dalibarda repens, Dendriopoterium menendezii, Dendriopoterium pulidoi, Dryas drummondii, Dryas octopetala, Duchesnea chrysantha, Duchesnea indica, Erythrocoma triflora, Fallugia paradoxa, Filipendula multijuga Filipendula purpurea, Filipendula ulmaria, Filipendula vulgaris, Fragaria chiloensis, Fragaria daltoniana, Fragaria gracilis, Fragaria grandiflora, Fragaria iinumae, Fragaria moschata, Fragaria nilgerrensis, Fragaria nipponica, Fragaria nubicola, Fragaria orientalis, Fragaria pentaphylla, Fragaria vesca, Fragaria virginiana, Fragaria viridis, Fragaria×ananassa, Fragaria sp. CFRA 538, Fragaria sp., Geum andicola, Geum borisi, Geum bulgaricum, Geum calthifolium, Geum chiloense, Geum geniculatum, Geum heterocarpum, Geum macrophyllum, Geum montanum, Geum reptans, Geum rivale, Geum schofieldii, Geum speciosum, Geum urbanum, Geum vernum, Geum sp. 'Chase 2507 K', Hagenia abyssinica, Horkelia cuneata, Horkelia fusca, Ivesia gordoni, Kerria japonica, Leucosidea sericea, Marcetella maderensis, Marcetella moquiniana, Margyricarpus pinnatus, Margyricarpus setosus, Novosieversia glacialis, Oncostylus cockaynei, Oncostylus leiospermus, Polylepis australis, Polylepis besseri, Polylepis crista-galli, Polylepis hieronymi, Polylepis incana, Polylepis lanuginosa, Polylepis multijuga, Polylepis neglecta, Polylepis pauta, Polylepis pepei, Polylepis quadrijuga, Polylepis racemosa, Polylepis reticulata, Polylepis rugulosa, Polylepis sericea, Polylepis subsericans, Polylepis tarapacana, Polylepis tomentella, Polylepis weberbaueri, Potentilla anserina, Potentilla arguta, Potentilla bifurca, Potentilla chinensis, Potentilla dickinsii, Potentilla erecta, Potentilla fragarioides, Potentilla fruticosa, Potentilla indica, Potentilla micrantha, Potentilla multifida, Potentilla nivea, Potentilla norvegica, Potentilla palustris, Potentilla peduncularis, Potentilla reptans, Potentilla salesoviana, Potentilla stenophylla, Potentilla tridentata, Rosa abietina, Rosa abyssinica, Rosa acicularis, Rosa agrestis, Rosa alba, Rosa alba×Rosa corymbifera, Rosa altaica, Rosa arkansana, Rosa arvensis, Rosa banksiae, Rosa beggeriana, Rosa blanda, Rosa bracteata, Rosa brunonii, Rosa caesia, Rosa californica, Rosa canina, Rosa carolina, Rosa chinensis, Rosa cinnamomea, Rosa columnifera, Rosa corymbifera, Rosa cymosa, Rosa davurica, Rosa dumalis, Rosa ecae, Rosa eglanteria, Rosa elliptica, Rosa fedtschenkoana, Rosa foetida, Rosa foliolosa, Rosa gallica, Rosa gallica×Rosa dumetorum, Rosa gigantea, Rosa glauca, Rosa helenae, Rosa henryi, Rosa hugonis, Rosa hybrid cultivar, Rosa inodora, Rosa jundzillii, Rosa laevigata, Rosa laxa, Rosa luciae, Rosa majalis, Rosa marretii, Rosa maximowicziana, Rosa micrantha, Rosa mollis, Rosa montana, Rosa moschata, Rosa moyesii, Rosa multibracteata, Rosa multiflora, Rosa nitida, Rosa odorata, Rosa palustris, Rosa pendulina, Rosa persica, Rosa phoenicia, Rosa platyacantha, Rosa primula, Rosa pseudoscabriuscula, Rosa roxburghii, Rosa rubiginosa, Rosa rugosa, Rosa sambucina, Rosa sempervirens, Rosa sericea, Rosa sertata, Rosa setigera, Rosa sherardii, Rosa sicula, Rosa spinosissima, Rosa stellata, Rosa stylosa, Rosa subcanina, Rosa subcollina, Rosa suffulta, Rosa tomentella, Rosa tomentosa, Rosa tunquinensis, Rosa villosa, Rosa virginiana, Rosa wichurana, Rosa willmottiae, Rosa woodsii; Rosa×damascena, Rosa×fortuniana, Rosa×macrantha, Rosa xanthina, Rosa sp., Rubus alceifolius, Rubus alleghaniensis, Rubus alpinus, Rubus amphidasys, Rubus arcticus, Rubus argutus, Rubus assamensis, Rubus australis, Rubus bifrons, Rubus caesius, Rubus caesius×Rubus idaeus, Rubus canadensis, Rubus canescens, Rubus caucasicus, Rubus chamaemorus, Rubus corchorifolius, Rubus crataegifolius, Rubus cuneifolius, Rubus deliciosus, Rubus divaricatus, Rubus ellipticus, Rubus flagellaris, Rubus fruticosus, Rubus geoides, Rubus glabratus, Rubus glaucus, Rubus gunnianus, Rubus hawaiensis, Rubus hawaiensis×Rubus rosifolius, Rubus hispidus, Rubus hochstetterorum, Rubus humulifolius, Rubus idaeus, Rubus lambertianus, Rubus lasiococcus, Rubus leucodermis, Rubus lineatus, Rubus macraei, Rubus maximiformis, Rubus minusculus, Rubus moorei, Rubus multibracteatus, Rubus neomexicanus, Rubus nepalensis, Rubus nessensis, Rubus nivalis, Rubus niveus, Rubus nubigenus, Rubus occidentalis, Rubus odoratus, Rubus palmatus, Rubus parviflorus, Rubus parvifolius, Rubus parvus, Rubus pectinellus, Rubus pedatus, Rubus pedemontanus, Rubus pensilvanicus, Rubus phoenicolasius, Rubus picticaulis, Rubus pubescens, Rubus rigidus, Rubus robustus, Rubus roseus, Rubus rosifolius, Rubus sanctus, Rubus sapidus, Rubus saxatilis, Rubus setosus, Rubus spectabilis, Rubus sulcatus, Rubus tephrodes, Rubus trianthus, Rubus tricolor, Rubus trifidus, Rubus trilobus, Rubus trivialis, Rubus ulmifolius, Rubus ursinus, Rubus urticifolius, Rubus vigorosus, Rubus sp. JPM-2004, Sanguisorba albiflora, Sanguisorba alpina, Sanguisorba ancistroides, Sanguisorba annua, Sanguisorba canadensis, Sanguisorba filiformis, Sanguisorba hakusanensis, Sanguisorba japonensis, Sanguisorba minor, Sanguisorba obtusa, Sanguisorba officinalis, Sanguisorba parviflora, Sanguisorba stipulata, Sanguisorba tenuifolia, Sarcopoterium spinosum, Sibbaldia procumbens, Sieversia pentapetala, Sieversia pusilla, Taihangia rupestris, Tetraglochin cristatum, Waldsteinia fragarioides, Waldsteinia geoides, Adenostoma fasciculatum, Adenostoma sparsifolium, Aruncus dioicus, Cercocarpus betuloides, Cercocarpus ledifolius, Chamaebatiaria millefolium, Chamaerhodos erecta, Gillenia stipulata, Gillenia trifoliata, Holodiscus discolor, Holodiscus microphyllus, Lyonothamnus floribundus, Neillia affinis, Neillia gracilis, Neillia sinensis, Neillia sparsiflora, Neillia thibetica, Neillia thyrsiflora, Neillia uekii, Neviusia alabamensis, Physocarpus alternans, Physocarpus amurensis, Physocarpus capitatus, Physocarpus malvaceus, Physocarpus monogynus, Physocarpus opulifolius, Purshia tridentata, Rhodotypos scandens, Sorbaria arborea, Sorbaria sorbifolia, Spiraea betulifolia, Spiraea cantoniensis, Spiraea densiflora, Spiraea japonica, Spiraea nipponica, Spiraea×vanhouttei, Spiraea sp., Stephanandra chinensis, Stephanandra incisa* and *Stephanandra tanakae.*

Particularly preferred Rosaceae genera include: *Malus, Pyrus, Cydonia, Prunus, Eriobotrya,* and *Mespilus.*

Particularly preferred Rosaceae species include: *Malus domestica, Malus sylvestris, Pyrus communis, Pyrus pyrifolia, Pyrus bretschneideri, Cydonia oblonga, Prunus salicina, Prunus cerasifera, Prunus persica, Eriobotrya japonica, Prunus dulcis, Prunus avium, Mespilus germanica* and *Prunus domestica*.

A particularly preferred Rosaceae genus is *Malus*.

A particularly preferred *Malus* species is *Malus domestica*.

Particularly preferred *Malus* species/cultivars include *Malus sieversii* 93.051 G01-048, *Malus aldenhamii, Malus pumila Niedzwetzkyana, Malus×domestica* cv. 'Prairiefire', *Malus×domestica* cv. 'Geneva', *Malus sieversii* 92.103 30-312.

A particularly preferred *Malus* cultivar is *Malus×domestica* niedwetzkyana.

Another preferred Rosaceae genus is *Pyrus*.

Particularly preferred *Pyrus* species include *Pyrus calleryana, Pyrus caucasica, Pyrus communis, Pyrus elaeagrifolia, Pyrus hybrid cultivar, Pyrus pyrifolia, Pyrus salicifolia, Pyrus ussuriensis, Pyrus×bretschneideri*.

A particularly preferred *Pyrus* species is *Pyrus communis*.

Another preferred genus is *Fragaria*.

Preferred *Fragaria* species include *Fragaria daltoniana, Fragaria gracilis, Fragaria grandiflora, Fragaria iinumae, Fragaria moschata, Fragaria nilgerrensis, Fragaria nipponica, Fragaria nubicola, Fragaria orientalis, Fragaria pentaphylla, Fragaria vesca, Fragaria virginiana, Fragaria viridis, Fragaria×ananassa, Fragaria* sp. CFRA 538.

Particularly preferred *Fragaria* species are *Fragaria×ananassa, Fragaria chiloensis* and *Fragaria vesca*.

DETAILED DESCRIPTION

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

Definitions

The term "comprising" as used in this specification and claims means "consisting at least in part of"; that is to say when interpreting statements in this specification and claims which include "comprising", the features prefaced by this term in each statement all need to be present but other features can also be present. Related terms such as "comprise" and "comprised" are to be interpreted in similar manner.

However, in preferred embodiments comprising can be replaced with consisting.

The term "chimeric" as used herein, with respect to the chimeric promoter polynucleotide of the invention, means comprised of sequences that are "recombined". Preferably the sequences that are "recombined" are not found together in nature.

Typically the chimeric promoter is comprised of sequence elements that are present in naturally occurring promoters. For example, one or more of the sequence elements present in a naturally occurring promoter may be duplicated or multiplied, in the context of a naturally occurring promoter, to produce a chimeric promoter of the invention. The naturally occurring promoter may be the same promoter as the sequence elements, or may be from a different promoter.

Preferably the chimeric promoter polynucleotide sequence of the invention is not found in naturally occurring plants in its entirety. However the chimeric promoter may be constructed from naturally occurring sequences that are recombined.

The term "recombine" as used herein means refers to any method of joining polynucleotides. The term includes end to end joining, and insertion of one sequence into another. The term is intended to encompass includes physical joining techniques such as sticky-end ligation and blunt-end ligation. The chimeric promoter polynucleotide sequence, or elements thereof, may also be artificially, or recombinantly synthesised to contain the recombined sequences.

Typically the chimeric promoter is synthesised by methods well known to those skilled in the art. However the chimeric promoter will contain the sequences as herein defined or specified, that are not normally found together in nature.

When a chimeric promoter of the invention comprises a particular element or motif, this means that the element or motif may be found within the chimeric promoter sequence or at either end of the chimeric promoter sequence.

A "naturally occurring" sequence, promoter or promoter element, is one that is found in at least one species in nature.

The term "derived from" with respect to plants or a particular type of plant, means the same as a sequence naturally occurring in those plants or that plant.

The term "sequence motif" as used herein means a stretch of nucleotides. Preferably the stretch of nucleotides is contiguous.

The term "MYB transcription factor" is a term well understood by those skilled in the art to refer to a class of transcription factors characterised by a structurally conserved DNA binding domain consisting of single or multiple imperfect repeats.

The term "A MYB transcription with an R2R3DNA binding domain" is a term well understood by those skilled in the art to refer to MYB transcription factors of the two-repeat class.

The term "modified" with respect to a plant with "modified expression" or a "modified phenotype" means modified relative to the same plant, or plant of the same type, in the non-transformed state.

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

A "fragment" of a polynucleotide sequence provided herein is a subsequence of contiguous nucleotides that is preferably at least 15 nucleotides in length. The fragments of the invention preferably comprises at least 20 nucleotides, more preferably at least 30 nucleotides, more preferably at least 40 nucleotides, more preferably at least 50 nucleotides and most preferably at least 60 contiguous nucleotides of a polynucleotide of the invention. A fragment of a polynucleotide sequence can be used in antisense, gene silencing, triple helix or ribozyme technology, or as a primer, a probe, included in a microarray, or used in polynucleotide-based selection methods.

The term "fragment" in relation to promoter polynucleotide sequences is intended to include sequences comprising cis-elements and regions of the chimeric promoter polynucleotide sequence capable of regulating expression of a polynucleotide sequence to which the fragment is operably linked.

Preferably fragments of promoter polynucleotide sequences of the invention comprise at least 46, more preferably at least 69, more preferably at least 92, more preferably at least 115, more preferably at least 138, more preferably at least 150, more preferably at least 200, more preferably at least 300, more preferably at least 400, more preferably at least 500, more preferably at least 600, more preferably at least 700, more preferably at least 800, more preferably at least 900, more preferably at least 1000, more preferably at least 1100, more preferably at least 1200, more preferably at least 1300, more preferably at least 1400, more preferably at least 1500, more preferably at least 1600 and most preferably at least 1700 contiguous nucleotides of the specified polynucleotide. Fragments of the chimeric promoter polynucleotide sequences can be used to control expression of an operably linked polynucleotide in a transgenic plant cells or plants.

The term "primer" refers to a short polynucleotide, usually having a free 3'OH group, that is hybridized to a template and used for priming polymerization of a polynucleotide complementary to the template. Such a primer is preferably at least 5, more preferably at least 6, more preferably at least 7, more preferably at least 9, more preferably at least 10, more preferably at least 11, more preferably at least 12, more preferably at least 13, more preferably at least 14, more preferably at least 15, more preferably at least 16, more preferably at least 17, more preferably at least 18, more preferably at least 19, more preferably at least 20 nucleotides in length.

The term "probe" refers to a short polynucleotide that is used to detect a polynucleotide sequence, that is complementary to the probe, in a hybridization-based assay. The probe may consist of a "fragment" of a polynucleotide as defined herein. Preferably such a probe is at least 5, more preferably at least 10, more preferably at least 20, more preferably at least 30, more preferably at least 40, more preferably at least 50, more preferably at least 100, more preferably at least 200, more preferably at least 300, more preferably at least 400 and most preferably at least 500 nucleotides in length.

Polypeptides and Fragments

The term "polypeptide", as used herein, encompasses amino acid chains of any length but preferably at least 5 amino acids, including full-length proteins, in which amino acid residues are linked by covalent peptide bonds. The polypeptides may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "fragment" of a polypeptide is a subsequence of the polypeptide that performs a function that is required for the biological activity and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing the above enzymatic activity.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques.

The term "derived from" with respect to a polynucleotide or polypeptide sequence being derived from a particular genera or species, means that the sequence has the same sequence as a polynucleotide or polypeptide sequence found naturally in that genera or species. The sequence, derived from a particular genera or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polynucleotides and polypeptides possess biological activities that are the same or similar to those of the inventive polynucleotides or polypeptides. The term "variant" with reference to polynucleotides and polypeptides encompasses all forms of polynucleotides and polypeptides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a specified polynucleotide sequence. Identity is found over a comparison window of at least 20 nucleotide positions, more preferably at least 50 nucleotide positions, more preferably at least 100 nucleotide positions, more preferably at least 200 nucleotide positions, more preferably at least 300 nucleotide positions, more preferably at least 400 nucleotide positions, more preferably at least 500 nucleotide positions, more preferably at least 600 nucleotide positions, more preferably at least 700 nucleotide positions, more preferably at least 800 nucleotide positions, more preferably at least 900 nucleotide positions, more preferably at least 1000 nucleotide positions, more preferably at least 1100 nucleotide positions, more preferably at least 1200 nucleotide positions, more preferably at least 1300 nucleotide positions, more preferably at least 1400 nucleotide positions, more preferably at least 1500 nucleotide positions, more preferably at least 1600 nucleotide positions, more preferably at least 1700 nucleotide positions and most preferably over the entire length of the specified polynucleotide sequence. For the 23 bp motifs in the chimeric promoters of the invention, or used in the methods of the invention, identity is preferably found over the whole 23 nucleotide positions.

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available on the internet from NCBI. The default parameters of bl2seq are utilized except that filtering of low complexity parts should be turned off.

The identity of polynucleotide sequences may be examined using the following unix command line parameters:
bl2seq -i nucleotideseq1 -j nucleotideseq2 -F F -p blastn The parameter -F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from hgmp.mrc.ac.uk/Software/EMBOSS on the worldwide web. The European Bioinformatics Institute server also provides the facility to perform EMBOSS-needle global alignments between two sequences on line at http:/www.ebi.ac.uk/emboss/align/.

Alternatively the GAP program, which computes an optimal global alignment of two sequences without penalizing terminal gaps, may be used to calculate sequence identity. GAP is described in the following paper: Huang, X. (1994) On Global Sequence Alignment. Computer Applications in the Biosciences 10, 227-235.

Sequence identity may also be calculated by aligning sequences to be compared using Vector NTI version 9.0, which uses a Clustal W algorithm (Thompson et al., 1994, Nucleic Acids Research 24, 4876-4882), then calculating the percentage sequence identity between the aligned sequences using Vector NTI version 9.0 (Sep. 2, 2003 ©1994-2003 InforMax, licenced to Invitrogen).

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polynucleotides may be determined using the publicly available bl2seq program from the BLAST suite of programs (version 2.2.5 [November 2002]) from NCBI via the internet.

The similarity of polynucleotide sequences may be examined using the following unix command line parameters:
bl2seq -i nucleotideseq1 -j nucleotideseq2 -F F -p tblastx The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1\times10^{-10}$ more preferably less than $1\times10^{-20}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$ and most preferably less than $1\times10^{-100}$ when compared with any one of the specifically identified sequences.

Alternatively, variant polynucleotides of the present invention hybridize to a specified polynucleotide sequence, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing). Tm for polynucleotide molecules greater than about 100 bases can be calculated by the formula Tm=81.5+0.41% (G+C-log (Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides such as those in constructs of the invention encoding proteins to be expressed, also encompasses polynucleotides that differ from the specified sequences but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation".

Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also contemplated. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [November 2002]) from NCBI on the internet and via the tblastx algorithm as previously described.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available via the internet from NCBI. The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at http://www.ebi.ac.uk/emboss/align/) and GAP (Huang, X. (1994) On Global Sequence Alignment. Computer Applications in the Biosciences 10, 227-235.) as discussed above are also suitable global sequence alignment programs for calculating polypeptide sequence identity.

Sequence identity may also be calculated by aligning sequences to be compared using Vector NTI version 9.0, which uses a Clustal W algorithm (Thompson et al., 1994, Nucleic Acids Research 24, 4876-4882), then calculating the percentage sequence identity between the aligned polypeptide sequences using Vector NTI version 9.0 (Sep. 2, 2003 ©1994-2003 InforMax, licenced to Invitrogen).

Polypeptide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI via the internet. The similarity of polypeptide sequences may be examined using the following unix command line parameters:

bl2seq -i peptideseq1 -j peptideseq2 -F F -p blastp

Variant polypeptide sequences preferably exhibit an E value of less than $1 \times 10^{-6}$ more preferably less than $1 \times 10^{-9}$, more preferably less than $1 \times 10^{-12}$, more preferably less than $1 \times 10^{-15}$, more preferably less than $1 \times 10^{-18}$, more preferably less than $1 \times 10^{-21}$, more preferably less than $1 \times 10^{-30}$, more preferably less than $1 \times 10^{-40}$, more preferably less than $1 \times 10^{-50}$, more preferably less than $1 \times 10^{-60}$, more preferably less than $1 \times 10^{-70}$, more preferably less than $1 \times 10^{-80}$, more preferably less than $1 \times 10^{-90}$ and most preferably $1 \times 10^{-100}$ when compared with any one of the specifically identified sequences.

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

Constructs, Vectors and Components thereof

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain a promoter polynucleotide such as a chimeric promoter polynucleotide of the invention including the necessary elements that permit transcribing the insert polynucleotide molecule, and, optionally, translating the transcript into a polypeptide. The insert polynucleotide molecule may be derived from the host cell, or may be derived from a different cell or organism and/or may be a synthetic or recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as *E. coli*.

The term "expression construct" refers to a genetic construct that includes the necessary elements that permit transcribing the insert polynucleotide molecule, and, optionally, translating the transcript into a polypeptide.

An expression construct typically comprises in a 5' to 3' direction:
a) a promoter, such as a chimeric promoter polynucleotide sequence of the invention, functional in the host cell into which the construct will be transformed,
b) the polynucleotide to be expressed, and
c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences.

The term "operably-linked" means that the sequence to be expressed is placed under the control of regulatory elements that include promoters, tissue-specific regulatory elements, temporal regulatory elements, enhancers, repressors and terminators.

The term "noncoding region" includes to untranslated sequences that are upstream of the translational start site and downstream of the translational stop site. These sequences are also referred to respectively as the 5' UTR and the 3' UTR. These sequences may include elements required for transcription initiation and termination and for regulation of translation efficiency. The term "noncoding" also includes intronic sequences within genomic clones.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to a polynucleotide sequence capable of regulating or driving the expression of a polynucleotide sequence to which the promoter is operably linked in a cell, or cell free transcription system. Promoters may comprise cis-initiator elements which specify the transcription initiation site and conserved boxes such as the TATA box, and motifs that are bound by transcription factors.

Examples of naturally occurring promoters which may be used, in whole or in part, in production of the chimeric promoters of the invention include: the promoter of the tobacco MYB10 gene (R2R3-MYB-153; Rushton et al 2008, Plant Physiol. 2008 10.1104/pp. 107.114041); the promoter of the *Arabidopsis* gene AtMYB75 (Borevitz et al, 2000, Plant Cell 12, 2383-2394); the promoter of the Vitamin C tranferase gene (Laing et al, 2007, PNAS, May 2007; 104: 9534-9539); the promoter of the Banyuls gene (Xie et al., 2003, Science. 2003 Jan. 17; 299(5605):396-9; Albert et al, 1997); the promoter of the MdTT2 gene (Genbank No. DQ267900); the promoter of the *Arabidopsis* AtTT2 gene (Nesi et al, 2001, Plant Cell 13, 2099-2114); the promoter of the *Arabidopsis* AtFT gene (Kardailsky et al 1999, SCIENCE Volume 286 Page 1962); and the promoters of fruit oxidosqualene-triterpenoid cyclases genes (Husselstein-Muller et al., 2001, Plant Mol. Biol. January; 45(1):75-92.). Other plant promoters are known to those skilled in the art and are described in the scientific literature.

The applicants have isolated promoter polynucleotide sequences from apple and pear and identified a sequence motif, and variants thereof, in such promoters which strongly influence the activity of such promoters. The applicants have shown that when the sequence motif is added to a promoter, the activity of that promoter is altered, and the promoter becomes more positively regulated by certain MYB transcription factors resulting in a significant increase in expression driven by the promoter.

The invention provides a method for producing chimeric promoters comprising the sequence motif, or motifs, and variants thereof. The invention also provides such chimeric promoters and variants thereof. The invention provides genetic constructs and vectors comprising the chimeric promoter polynucleotide sequences, and transgenic plant cells and transgenic plants comprising the chimeric promoter polynucleotide sequence, genetic constructs, or vectors of the invention.

The invention provides the opportunity to produce novel promoters with desirable activity. The invention also provides the opportunity to alter the activity of existing promoters by adding or inserting the sequence motifs, or variant thereof, to such existing promoters. Such novel or modified chimeric promoters may be regulated by certain MYB transcription factors. In this way expression of sequences operably linked to the chimeric promoters may be expressed in a desirable way and may be individually or co-ordinately regulated by the MYB transcription factors. The MYB transcription factors may be naturally expressed or may be expressed following genetic transformation.

The invention also provides methods for producing plants with modified gene expression and modified phenotype. The invention further provides plants produced by the methods of the invention.

Methods for Isolating or Producing Polynucleotides

The polynucleotide molecules of the invention can be isolated by using a variety of techniques known to those of ordinary skill in the art. By way of example, such polynucleotides can be isolated through use of the polymerase chain reaction (PCR) described in Mullis et al., Eds. 1994 The Polymerase Chain Reaction, Birkhauser, incorporated herein by reference. The polynucleotides of the invention can be amplified using primers, as defined herein, derived from the polynucleotide sequences of the invention.

Further methods for isolating polynucleotides of the invention, or useful in the methods of the invention, include use of all or portions, of the polynucleotides set forth herein as hybridization probes. The technique of hybridizing labeled polynucleotide probes to polynucleotides immobilized on solid supports such as nitrocellulose filters or nylon membranes, can be used to screen the genomic. Exemplary hybridization and wash conditions are: hybridization for 20 hours at 65° C. in 5.0×SSC, 0.5% sodium dodecyl sulfate, 1×Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1×SSC, 1% (w/v) sodium dodecyl sulfate, at 60° C.

The polynucleotide fragments of the invention may be produced by techniques well-known in the art such as restriction endonuclease digestion, oligonucleotide synthesis and PCR amplification.

A partial polynucleotide sequence may be used, in methods well-known in the art to identify the corresponding full length polynucleotide sequence and/or the whole gene/and/or the promoter. Such methods include PCR-based methods, 5'RACE (Frohman M A, 1993, Methods Enzymol. 218: 340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, *Nucleic Acids Res* 16, 8186, incorporated herein by reference). The method uses several restriction enzymes to generate a suitable fragment in the known region of a polynucleotide. The fragment is then circularized by intramolecular ligation and used as a PCR template. Divergent primers are designed from the known region. Promoter and flanking sequences may also be isolated by PCR genome walking using a GenomeWalker™ kit (Clontech, Mountain View, Calif.), following the manufacturers instructions. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilise a sequence identical (or at least highly similar) to that in the plant, for which reduced expression is desired. For these reasons among others, it is desirable to be able to identify and isolate orthologues of a particular gene in several different plant species. Variants (including orthologues) may be identified by the methods described.

The promoter sequences disclosed may be further characterized to identify other fragments, such as cis-elements and regions, capable of regulating to expression of operably linked sequences, using techniques well-known to those skilled in the art. Such techniques include 5' and/or 3' deletion analysis, linker scanning analysis and various DNA footprinting techniques (Degenhardt et al., 1994 Plant Cell:6(8) 1123-34; *Directed Mutagenesis: A Practical Approach IRL Press* (1991)). Fragments include truncated versions of longer promoter sequences which may terminate (at the 3' end) at or close to the transcriptional start site. Methods for identifying the transcription start site of a promoter are well-known to those skilled in the art (discussed in Hashimoto et al., 2004, Nature Biotechnology 22, 1146-1149).

The techniques described above may be used to identify a fragment that defines essential region of the promoter that is able to confer the desired expression profile. The essential region may function by itself or may be fused to a core promoter to drive expression of an operably linked polynucleotide.

The core promoter can be any one of known core promoters such as the Cauliflower Mosaic Virus 35S or 19S promoter (U.S. Pat. No. 5,352,605), ubiquitin promoter (U.S. Pat. No. 5,510,474) the IN2 core promoter (U.S. Pat. No. 5,364,780) or a Figwort Mosaic Virus promoter (Gruber, et al. "Vectors for Plant Transformation" *Methods in Plant Molecular Biology and Biotechnology*) et al. eds, CRC Press pp. 89-119 (1993)).

Promoter fragments can be tested for their utility in driving expression in any particular cell or tissue type, or at any particular developmental stage, or in response to any particular stimulus by techniques well-known to those skilled in the art. Techniques include operably-linking the promoter fragment to a reporter or other polynucleotide and measuring reporter activity or polynucleotide expressions in plants. Some of such techniques are described in the Examples section of this specification.

Methods for Identifying Variants
Physical Methods

Variant polynucleotides may be identified using PCR-based methods (Mullis et al., Eds. 1994 The Polymerase Chain Reaction, Birkhauser).

Alternatively library screening methods, well known to those skilled in the art, may be employed (Sambrook et al., Molecular Cloning: A Laboratory Manual, 2nd Ed. Cold Spring Harbor Press, 1987). When identifying variants of the probe sequence, hybridization and/or wash stringency will typically be reduced relatively to when exact sequence matches are sought.

Computer-Based Methods

Polynucleotide and polypeptide variants may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from NCBI via the internet or from the National Center for Biotechnology Information (NCBI), National Library of Medicine, Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over, only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680, internet address igbmc.u.strasbg.fr/BioInfo/ClustalW/Top or T-COFFEE (Cedric Notredame, Desmond G. Higgins, Jaap Hering a, T-Coffee: A novel method for fast and accurate multiple sequence alignment, J. Mol. Biol. (2000) 302: 205-217)) or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database available via the internet at expasy.org/prosite contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Methods for Producing Constructs and Vectors

The genetic constructs of the present invention comprise one or more polynucleotide sequences of the invention and/or polynucleotides encoding polypeptides disclosed, and may be useful for transforming, for example, bacterial, fungal, insect, mammalian or particularly plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Constructs and Vectors

The invention provides a host cell which comprises a genetic construct or vector of the invention. Host cells may be derived from, for example, bacterial, fungal, insect, mammalian or plant organisms.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Methods for Producing Plant Cells and Plants Comprising Constructs and Vectors

The invention further provides plant cells which comprise a genetic construct of the invention, and plant cells modified to alter expression of a polynucleotide or polypeptide. Plants comprising such cells also form an aspect of the invention.

Methods for transforming plant cells, plants and portions thereof with polynucleotides are described in Draper et al., 1988, Plant Genetic Transformation and Gene Expression. A Laboratory Manual, Blackwell Sci. Pub. Oxford, p. 365; Potrykus and Spangenburg, 1995, Gene Transfer to Plants. Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

The following are representative publications disclosing genetic transformation protocols that can be used to genetically transform the following plant species: Rice (Alam et al., 1999, Plant Cell Rep. 18, 572); apple (Yao et al., 1995, Plant Cell Reports 14, 407-412); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9, 821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); perennial ryegrass (Bajaj et al., 2006, Plant Cell Rep. 25, 651); grasses (U.S. Pat. Nos. 5,187,073, 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792, 935); soybean (U.S. Pat. Nos. 5,416,011; 5,569,834; 5,824, 877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); *brassica* (U.S. Pat. Nos. 5,188,958; 5,463,174 and 5,750,871); and cereals (U.S. Pat. No. 6,074,877); pear (Matsuda et al., 2005, Plant Cell Rep. 24(1):45-51); *Prunus* (Ramesh et al., 2006, Plant Cell Rep. 25(8):821-8; Song and Sink 2005, Plant Cell Rep. 2006; 25(2):117-23; Gonzalez Padilla et al., 2003, Plant Cell Rep. 22(1):38-45); strawberry (Oosumi et al., 2006, Planta.; 223(6):1219-30; Folta et al., 2006, Planta. 2006 Apr. 14; PMID: 16614818), rose (Li et al., 2003, Planta. 218(2): 226-32), and *Rubus* (Graham et al., 1995, Methods Mol. Biol. 1995; 44:129-33). Transformation of other species is also contemplated by the invention. Suitable methods and protocols for transformation of other species are available in the scientific literature.

Methods for Genetic Manipulation of Plants

A number of strategies for genetically manipulating plants are available (e.g. Birch, 1997, Ann Rev Plant Phys Plant Mol Biol, 48, 297). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. Strategies may also be designed to increase expression of a polynucleotide/polypeptide in response to external stimuli, such as environmental stimuli. Environmental stimuli may include environmental stresses such as mechanical (such as herbivore activity), dehydration, salinity and temperature stresses. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed or to reduce expression of a polynucleotide/polypeptide in response to an external stimuli. Such strategies are known as gene silencing strategies.

Genetic constructs for expression of genes in transgenic plants typically include promoters, such as promoter polynucleotides of the invention, for driving the expression of one or more cloned polynucleotide, terminators and selectable marker sequences to detect presence of the genetic construct in the transformed plant.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zin gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenbert. Eds) Springer Verlag. Berline, pp. 325-336.

Gene silencing strategies may be focused on the gene itself or regulatory elements which effect expression of the encoded polypeptide. "Regulatory elements" is used here in the widest possible sense and includes other genes which interact with the gene of interest.

Genetic constructs designed to decrease or silence the expression of a polynucleotide/polypeptide may include an antisense copy of a polynucleotide. In such constructs the polynucleotide is placed in an antisense orientation with respect to the promoter and terminator.

An "antisense" polynucleotide is obtained by inverting a polynucleotide or a segment of the polynucleotide so that the transcript produced will be complementary to the mRNA transcript of the gene, e.g.,

```
5'GATCTA 3'         3'CTAGAT 5' (antisense strand)
(coding strand)

3'CUAGAU 5' mRNA    5'GAUCUCG 3' antisense RNA
```

Genetic constructs designed for gene silencing may also include an inverted repeat. An 'inverted repeat' is a sequence that is repeated where the second half of the repeat is in the complementary strand, e.g.,

```
5'-GATCTA . . . TAGATC-3'

3'-CTAGAT . . . ATCTAG-5'
```

The transcript formed may undergo complementary base pairing to form a hairpin structure. Usually a spacer of at least 3-5 bp between the repeated region is required to allow hairpin formation.

Another silencing approach involves the use of a small antisense RNA targeted to the transcript equivalent to an miRNA (Llave et al., 2002, Science 297, 2053). Use of such small antisense RNA corresponding to polynucleotide of the invention is expressly contemplated.

The term genetic construct as used herein also includes small antisense RNAs and other such polynucleotides useful for effecting gene silencing.

Transformation with an expression construct, as herein defined, may also result in gene silencing through a process known as sense suppression (e.g. Napoli et al., 1990, Plant Cell 2, 279; de Carvalho Niebel et al., 1995, Plant Cell, 7, 347). In some cases sense suppression may involve overexpression of the whole or a partial coding sequence but may also involve expression of non-coding region of the gene, such as an intron or a 5' or 3' untranslated region (UTR). Chimeric partial sense constructs can be used to coordinately silence multiple genes (Abbott et al., 2002, Plant Physiol. 128(3): 844-53; Jones et al., 1998, Planta 204: 499-505). The use of such sense suppression strategies to silence the expression of a sequence operably-linked to promoter of the invention is also contemplated.

The polynucleotide inserts in genetic constructs designed for gene silencing may correspond to coding sequence and/or non-coding sequence, such as promoter and/or intron and/or 5' or 3' UTR sequence, or the corresponding gene.

Other gene silencing strategies include dominant negative approaches and the use of ribozyme constructs (McIntyre, 1996, Transgenic Res, 5, 257)

Pre-transcriptional silencing may be brought about through mutation of the gene itself or its regulatory elements. Such mutations may include point mutations, frameshifts, insertions, deletions and substitutions.

Plants

The term "plant" is intended to include a whole plant or any part of a plant, propagules and progeny of a plant.

The term 'propagule' means any part of a plant that may be used in reproduction or propagation, either sexual or asexual, including seeds and cuttings.

A "transgenic" or transformed" plant refers to a plant which contains new genetic material as a result of genetic manipulation or transformation. The new genetic material may be derived from a plant of the same species as the resulting transgenic of transformed plant or from a different species. A transformed plant includes a plant which is either stably or transiently transformed with new genetic material.

The plants of the invention may be grown and either self-ed or crossed with a different plant strain and the resulting hybrids, with the desired phenotypic characteristics, may be identified. Two or more generations may be grown. Plants resulting from such standard breeding approaches also form part of the present invention.

BRIEF DESCRIPTION OF THE DRAWINGS

FIG. 1 shows the promoter polynucleotide sequence of SEQ ID NO: 5, showing the position of the repeat motifs (1, 2, 3A, 3B, 4, 5 and 6), the microsatellite (microsat) and several restriction enzyme sites.

FIGS. 12-1, 12-2 and 12-3 shows an alignment between the sequences of the MYB10 promoters from white-fleshed apple and pear (SEQ ID NO:43 and SEQ ID NO:13, respectively) and highlights with, underlining, the conserved 23 bp repeat motif.

FIG. 13 shows that other MYB10 sequences can transactivate the R6:MdMYB10 promoter in a Dual Luciferase Transient Assay in Tobacco. Leaves of N. benthamiana were infiltrated with pMdMYB10R1-LUC or pMdMYB10R6-LUC promoter fusions on their own or coinfiltrated with 35S:MYB and bHLH as indicated. Luminescence of LUC and REN was measured 3 days later and expressed as a ratio of LUC to REN. Error bars are the SE for 4 replicate reactions.

FIG. 14 shows a schematic representation of the strategy for cloning the apple R6 domain into the PcMYB10, AtPAP1 and VitC2 promoters. The R6 domain was amplified from the 'Red Field' R6:MdMYB10 allele, digested with DraI and inserted in the PcMYB10, AtPAP1 and VitC2 promoters driving the Luciferase reporter gene at the indicated restriction sites. Each blue shaded box represents a 23 bp-single repeat, and each smaller light box represents the relative position of the microsatellite region.

FIG. 15 shows that MdMYB10 combined with bHLH3 transactivates other MYB10 chimeric promoter fusions containing copies of the 23 bp repeat count. A. Leaves of *N. benthamiana* were coinfiltrated with the MYB promoter fusions from apple, pear and *Arabidopsis*, either containing the apple R6 domain or not, and the MdMYB10/bHLH3 transcription factors. B. Leaves were infiltrated with the pear MYB10 promoter or the AtPAP1 promoter, either containing or not the R6 domain, and their corresponding MYB/bHLH co-factors. Luminescence of LUC and REN was measured 3 days later and expressed as a ratio of LUC to REN. Error bars are the SE for 4 replicate reactions.

FIG. 16 shows that MdMYB10 together with bHLH3 transactivates the VitC2 promoters containing the apple R6 domain in a Dual Luciferase Transient Assay. Leaves of *N. benthamiana* were coinfiltrated with the VitC2 promoter fusions from kiwifruit, either containing the apple R6 domain or not, and the MdMYB10 transcription factor alone or combined to bHLH3. In each case the presence of the R6 domain is associated to a high level of transactivation of the promoter fusion. Luminescence of LUC and REN was measured 3 days later and expressed as a ratio of LUC to REN. Error bars are the SE for 4 replicate reactions.

FIG. 17 is a schematic representation of the R6 motif amplified by CB02 and RE161 primers. Also shown in boxes is the position of each 23 bp repeat motif R1-R6, and the position of the DraI restriction site. The sequence is also given in SEQ ID NO:44.

EXAMPLES

The invention will now be illustrated with reference to the following non-limiting examples.

Example 1

Isolation of the Full Length MdMYB10 Promoter Polynucleotides from White-Fleshed and Red-Fleshed Apple Cultivars, and Identification of Additional Elements within the Promoter from the Red-Fleshed Cultivar Isolation of Genomic DNA Genomic DNA was isolated from the leaves of a white-fleshed apple cultivar (*Malus domestica* Royal Gala) and from the leaves of a red-fleshed apple cultivar (*Malus×pumila* niedwetzkyana) using a Qiagen DNeasy Plant Mini Kit, according to the manufacturers instructions (Qiagen, Valencia, Calif.).

Promoter Isolation

A 1.7-1.8 Kb region of the upstream regulatory region of the MdMYB10 gene was isolated from the DNA of both the white-fleshed and the red-fleshed cultivar by PCR genome walking using a GenomeWalker™ kit (Clontech, Mountain View, Calif.), following the manufacturers instructions.

The isolated promoters were sequenced by standard techniques. The sequence of the promoter from the red-fleshed cultivar is shown in SEQ ID NO: 5. The sequence of the promoter from the white-fleshed cultivar is shown in SEQ ID NO: 8.

The sequence of the MdMYB10 polypeptide is shown in SEQ ID NO: 6. The polynucleotide sequence (cDNA) encoding the MdMYB10 polypeptide is shown in SEQ ID NO: 7.

By comparing the sequences of the promoters from white-fleshed and red-fleshed apple cultivars the applicants identified a 23-base pair sequence motif found in both promoters. In the promoter from the white-fleshed cultivar, the motif is present as a single copy (with a 1 bp difference versus the motif in the promoter from the red-fleshed cultivar). In the promoter from the red-fleshed cultivar the motif is present at a corresponding position, but in addition, the motif is duplicated in five tandem repeats to form a minisatellite repeat unit.

The sequence of the repeat motif is shown in SEQ ID NO: 1.

The sequence of the minisatellite unit comprising five copies of the repeat motif is shown in SEQ ID NO: 2.

Figure 1:
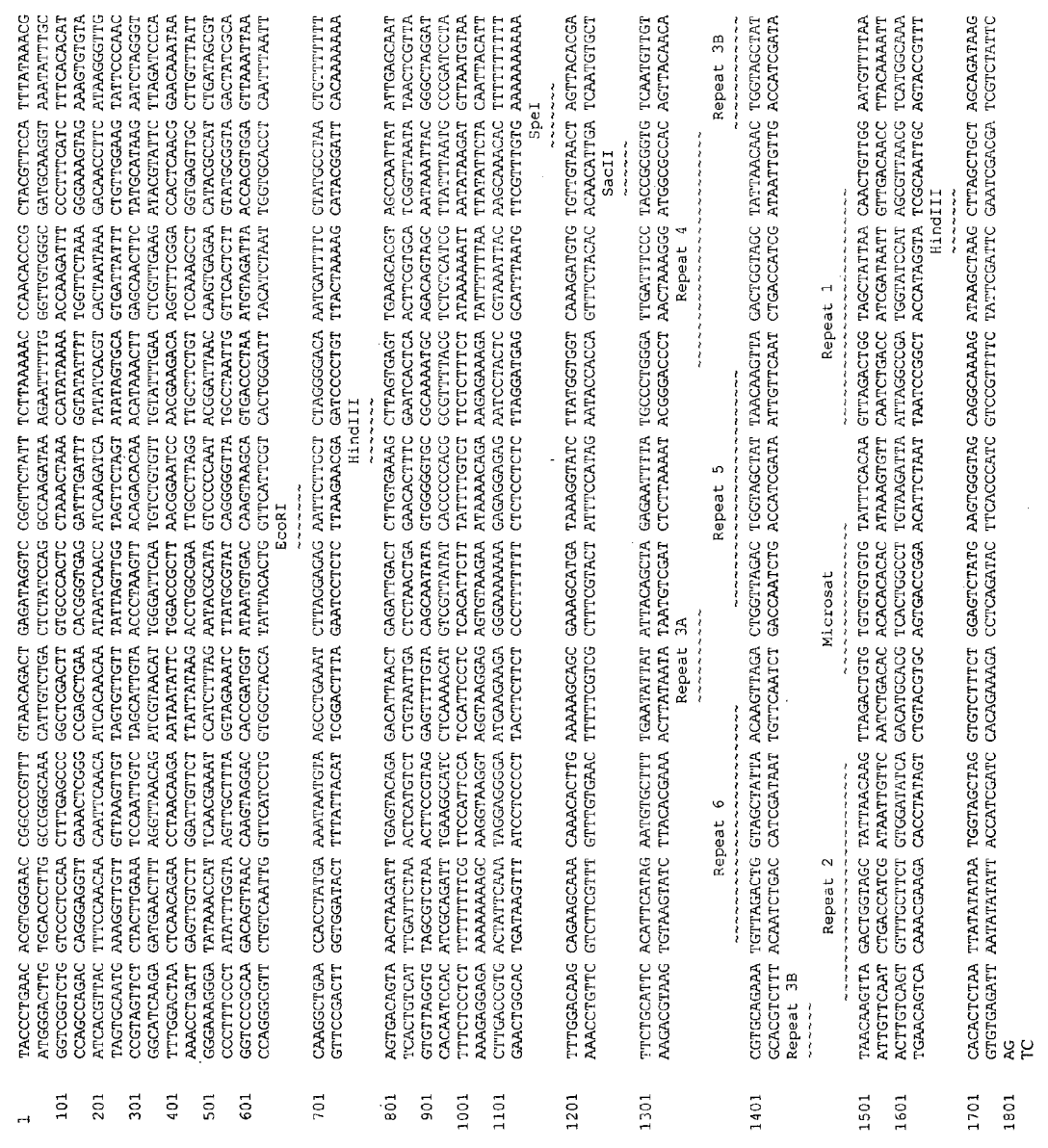

FIG. 1 shows the sequence of the promoter from the red-fleshed variety as shows the position of the repeated motifs. The minisatellite unit precedes a di-nucleotide microsatellite found in both promoters.

The sequence of the microsatellite is shown in SEQ ID NO: 3.

Figure 2:
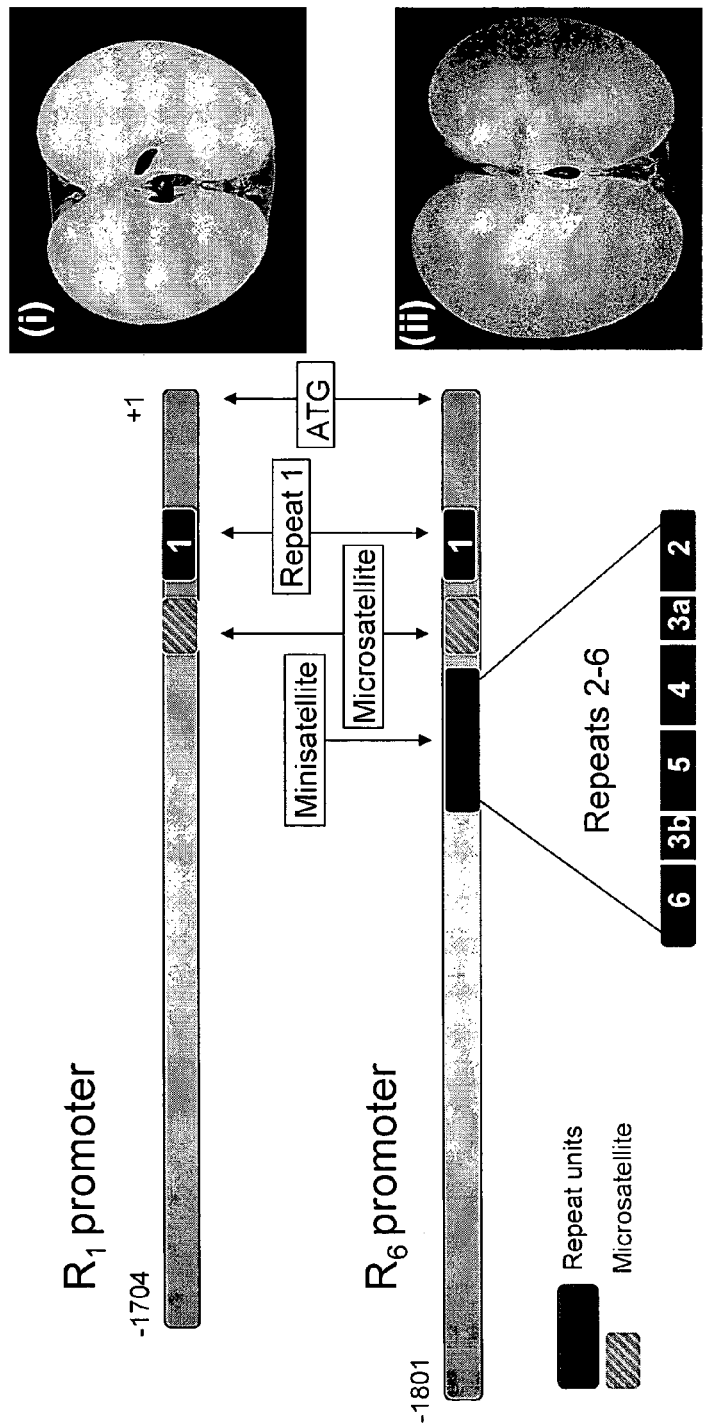
FIG. 2 shows a schematic representation of the MdMYB10 $R_1$ promoter from the white-fleshed cultivar with a single repeat motif (1) and the microsatelite (MS). The figure also shows schematic representation of the structure and location of the additional repeat unit composed of repeat units 2, 3a, 3b, 4, 5 and 6 found in the promoter of the red-fleshed cultivar $R_6$, relative to the promoter from the white-fleshed cultivar. Example phenotypes for the MdMYB10 $R_1$ and $R_6$ promoter versions are shown to the left, Malus×domestica Royal Gala (i) and Malus×domestica niedzwetzkyana (ii).

FIG. 2 shows a schematic representation of promoter from the white-fleshed cultivar and shows the relative position and structure of the additional minisatellite repeat unit found in the promoter of the red-fleshed cultivar. Minisatellites, similar to these, have been shown to have an effect on transcriptional regulation in humans (Kominato et al., (1997). *J. Biol. Chem.* 272, 25890, Lew et al., (2000). *Proc. Natl. Acad. Sci. U.S.A.* 97, 12508 and to produce phenotypic alteration in *Saccharomyces cerevisiae* (Verstrepen et al., (2005) *Nat. Genet.* 37, 986).

Example 2

Demonstration of Regulation of Expression of Operably Linked Polynucleotide Sequences by the Promoter Polynucleotides of the Invention Dual Luciferase Assay of Transiently Transformed Tobacco Leaves The promoter sequences for MdMYB10 from the red-fleshed and white-fleshed cultivars (SEQ ID NOs: 4 and 5 respectively) were separately inserted into the cloning site of pGreen 0800-LUC (Hellens et al., 2005, R. P. Hellens, A. C. Allan, E. N. Friel E N, K. Bolitho, K. Grafton, M. D. Templeton, S. Karunairetnam, W. A. Laing, *Plant Methods* 1:13). In the same construct, a luciferase gene from *Renilla* (REN), under the control of a 35S promoter, provided an estimate of the extent of transient expression. Activity is expressed as a ratio of LUC to REN activity. The promoter-LUC fusion was used in transient transformation by mixing 100 µl of *Agrobacterium* strain GV3101 (MP90) transformed with the reporter cassette with or without another *Agrobacterium* culture (900 µl) transformed with a cassette containing MdMYB10 fused to the 35S promoter. *Nicotiana tabacum* 'Samsun' plants were grown until at least 6 leaves were available for infiltration with *Agrobacterium*. A 10 µl loop of confluent bacterium were resuspended in 10 ml of infiltration media (10 mM $MgCl_2$, 0.5 µM acetosyringone), to an $OD_{600}$ of 0.2, and incubated at room temperature without shaking for 2 h before infiltration. Approximately 150 µl of this *Agrobacterium* mixture was infiltrated at six points into a young leaf of *N. tabacum* and transient expression was analysed 3 days after inoculation. Six technical replicates of 3 mm Ø leaf discs were excised from each plant using a leaf hole-punch and buffered in Phosphate Buffer Saline (PBS). Plate-based assays were conducted using a Berthold Orion Microplate Luminometer (Berthold Detection Systems, Oak Ridge, Tenn., USA) according to the manufacturer's specifications for the dual luciferase assay, using the Dual Glow assay reagents (Promega, Madison, Wis.) for firefly luciferase and *Renilla* luciferase. Luminescence was calculated using Simplicity version 4.02 software (Berthold Detection Systems).

Figure 4:
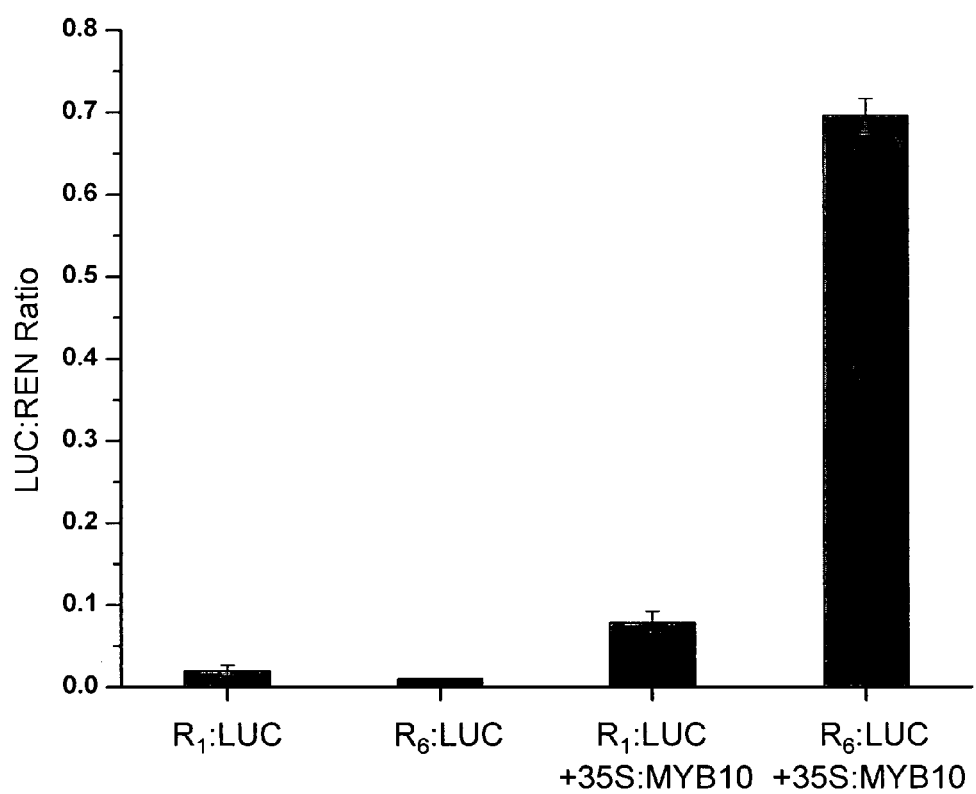
FIG. 4 shows trans-activation of the promoters from white-fleshed ($R_1$) and red-fleshed ($R_6$) cultivars by the MdMYB10 gene in transient tobacco transformation assays. Both promoters were infiltrated with and without MdMYB10. Error bars shown are ±S.E. of the means of 6 replicate experiments.
Figure 5:
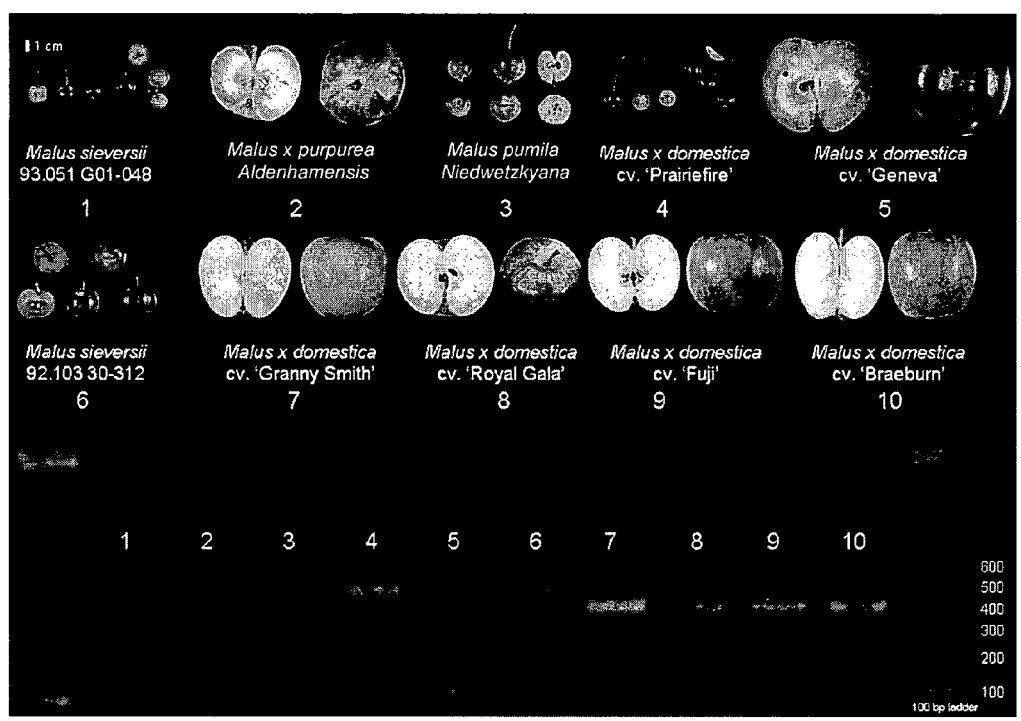
FIG. 5 shows that amplification of a PCR product comprising the minsatellite motif serves as a marker that distinguishes white-fleshed and red-fleshed apple cultivars. A total of 87 cultivars were screened using the PCR primer pair described in Example 3. PCR products were separated on 0.9% agarose gels and stained with ethidium bromide. The figure shows the PCR amplification obtained over a subset of 10 apple varieties. Two alleles were found: a 496 bp fragment corresponding to the promoter of SEQ ID NO: 5, which was only present in red flesh varieties (lanes 1-6) and was absent in white-fleshed varieties (lanes 7-10), and a 392 bp allele present in both types of fruit. Red-fleshed varieties: 1: open-pollinated (OP) Malus 'Mildew Immune Seedling' 93.051 G01-048; 2: M.×purpurea 'Aldenhamensis'; 3: M. pumila var. niedzwetzkyana; 4: M. 'Prairifire'; 5: OP M. pumila var. niedzwetzkyana 'Geneva'; 6: OP M.×domestica 'Pomme Grise' 92.103 30-312; 7: M.×domestica 'Granny Smith'; 8: M.×domestica 'Royal Gala'; 9: M.×domestica 'Fuji'; 10: M.×domestica 'Braeburn'.

The results, as shown in FIG. 4, show that the promoter ($R_6$) from the red-fleshed cultivar containing the minisatellite repeat unit drives expression of the operably linked sequence encoding luciferase at 7 times the level of expression driven by the promoter ($R_1$) from the white-fleshed cultivar (from which the minisatellite repeat unit is absent) when the MdMYB10 protein is also expressed. This result demonstrates the significance of the extra sequence present in $R_6$ promoter (including additional copies of the repeat motif) from the red-fleshed variety.

The results also show that co-expression of the MdMYB10 transcription factor results in a 10-fold increase in expression of the luciferase sequence that is operably linked to the promoter ($R_6$) from the red-fleshed cultivar. The effect of MdMYB10 from the white-fleshed cultivar is much smaller. This result shows that the promoter polynucleotide of the invention is positively regulated by the MYB transcription factor MdMYB10.

Example 3

The Presence of the Minisatellite Unit in the Promoter of the Invention is Consistently Associated with Red-Flesh in Naturally Occurring Red-Fleshed Apple Varieties Minisatellite Region PCR Amplification and Sequencing The fruit flesh (cortex) of most apple cultivars is white or off-white in colour. The skin is usually green or red, the skin reddening in response to developmental, hormonal and light signals (Ubi et al., 2006, *Plant Sci.* 170, 571). There are, however, a number of high anthocyanin, red-fleshed apples, including *Malus×pumila niedzwetzkyana*, originating from the wild-apple forests of Khazakhstan.

In apple, anthocyanin accumulation is specifically regulated by MdMYB10, with MdMYB10 transcript levels greatly elevated in red-fleshed varieties (Espley et al., 2007, *Plant J.* 49, 414).

Genomic DNA samples from several red-fleshed and white-fleshed apple cultivars listed in the Table 1 below were supplied by Charles J Simon and Philip Forsline, Agricultural Research Services USDA.

Apple genomic DNA from 19 cultivars was amplified using a pair of PCR primers located in the MdMYB10 promoter (forward: 5'-GGAGGGGAATGAAGAAGAGG-3'—SEQ ID NO: 9; reverse: 5'-TCCACAGAAGCAAACACTGAC-3'—SEQ ID NO: 10). PCR reactions were carried out in 16.5 µl volume containing 1×PCR buffer mix (Invitrogen, Carlsbad, Calif.), 1.3 mM $MgCl_2$, 100 µM of each dNTP, 0.72% formamide, 10 µM of each primer, 0.5 U of Platinum® Taq DNA polymerase (Invitrogen) and 2 ng of genomic DNA. PCR amplifications were performed in a Hybaid PCR Express Thermal Cycler (Thermo Electron Corporation, Waltham, Mass.) with conditions as follows: 94° C. for 2 min 45 sec followed by 40 cycles at 94° C. for 55 sec, 55° C. for 55 and 72° C. for 1 min 39 sec, and a final elongation at 72° C. for 10 min. The PCR products obtained were cloned using the TOPO TA Cloning® kit (Invitrogen). Four clones were sequenced for each PCR product. The sequences were aligned using Vector NTI (Invitrogen).

Association of the Minisatellite with the Red-Fleshed Phenotype

Figure 3:
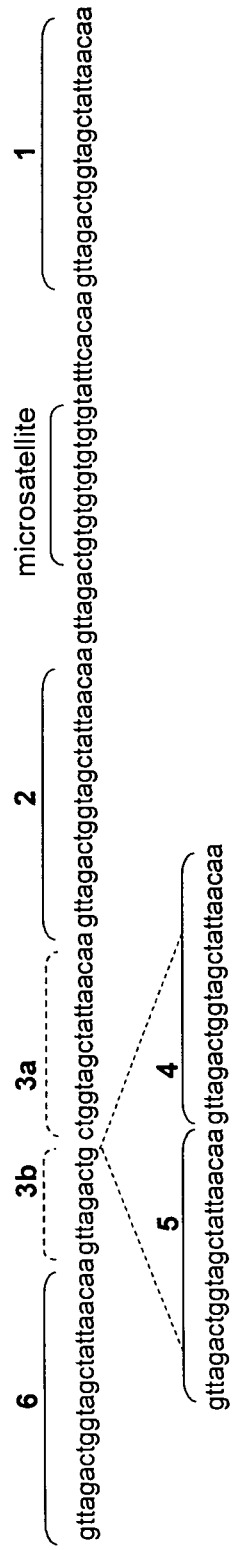
FIG. 3 shows the portion of the sequence (SEQ ID NO:4) of the promoter from the red-fleshed apple cultivar including repeat motifs 1, 2, 3a, 3b, 4, 5 and 6 and the microsatellite region

Previously we have shown that MdMYB10 is linked to the red flesh and red foliage phenotype in apple (Chagné et al, 2007, *BMC Genomics*, 8, 212). Further, PCR amplification of the promoter region from red and white-fleshed varieties consistently showed that the $R_6$ minisatellite was amplified in all the red phenotypes (FIG. 3). We determined the association of the repeat motif with the red-fleshed phenotype by sequencing the region encompassing the minisatellite motif over 19 diverse apple varieties (11 red and 8 white flesh; Table 1). A number of sequence variations were found in the upstream region, but only the minisatellite polymorphism is perfectly associated with the elevated accumulation of anthocyanins that causes red flesh and red foliage. The same region was PCR-amplified from a further set of 68 white-fleshed apple cultivars and wild accessions taken from two collections of *Malus* species, and in each case the product corresponding to the minisatellite motif was absent (data not shown). All the white-fleshed versions tested contained only the $R_1$ version whilst the red-fleshed versions contained both $R_1$ and $R_6$ or $R_6$ only.

TABLE 1

| Accession | Flesh colour | G/T SNP Pos 81 | Minisatellite motif | A/T SNP Pos 448 |
|---|---|---|---|---|
| *Malus × domestica* 'Babine'* | Red | G:G | $R_1$:$R_6$ | A:T |
| *Malus × domestica* 'Okanagan'* | Red | G:G | $R_1$:$R_6$ | A:T |
| *Malus × domestica* 'Simcoe'* | Red | G:G | $R_6$:$R_6$ | T:T |
| *Malus × domestica* 'Slocan'* | Red | G:T | $R_1$:$R_6$ | A:T |
| *Malus marjorensis* 'Formosa'* | Red | G:T | $R_1$:$R_6$ | A:T |
| *Malus sieversii* 629319* | Red | G:G | $R_6$:$R_6$ | T:T |
| *Malus sieversii* FORM 35 (33-01)* | Red | G:T | $R_1$:$R_6$ | A:T |
| *Malus sieversii* 01P22* | Red | G:G | $R_6$:$R_6$ | T:T |
| *Malus sieversii* 3563.q* | Red | G:G | $R_6$:$R_6$ | T:T |
| *Malus Aldenhamii* | Red | T:T | $R_1$:$R_6$ | A:T |
| *Malus × domestica* 91.136 B6-77 | Red | G:T | $R_1$:$R_6$ | A:T |
| *Malus × domestica* 'Close' | White | G:T | $R_1$:$R_1$ | A:T |
| *Malus × domestica* 'Mr Fitch' | White | T:T | $R_1$:$R_1$ | A:A |
| *Malus × domestica* 'Guldborg' | White | G:T | $R_1$:$R_1$ | A:T |
| *Malus × domestica* 'Alkmene' | White | T:T | $R_1$:$R_1$ | A:A |
| *Malus × domestica* 'Red Melba' | White | T:T | $R_1$:$R_1$ | A:A |
| *Malus × domestica* 'Rae Ime' | White | G:G | $R_1$:$R_1$ | T:T |
| *Malus × domestica* 'Lady Williams' | White | T:T | $R_1$:$R_1$ | A:A |

TABLE 1-continued

| Accession | Flesh colour | G/T SNP Pos 81 | Minisatellite motif | A/T SNP Pos 448 |
|---|---|---|---|---|
| *Malus* x *domestica* 'Granny Smith' | White | G:T | $R_1:R_1$ | A:A |
| Association test ($r^2$) | | 0.185 | 1 | 0.491 |

"$R_1$" refers to the absence of the minisatellite unit as found in the promoter from the white-fleshed Royal Gala cultivar.
"$R_6$" refers to the presence of the minisatellite unit as found in the promoter from the red-fleshed *Malus* x *pumila niedwetzkyana* cultivar.

Given that the single repeat unit is present in the promoter from the white-fleshed, the presence of additional repeat units in the promoter from the red-fleshed cultivar are likely to account for the known increased expression level of MdMY10 and resulting anthocyanin accumulation red-fleshed apple cultivars.

Example 4

Figure 6:
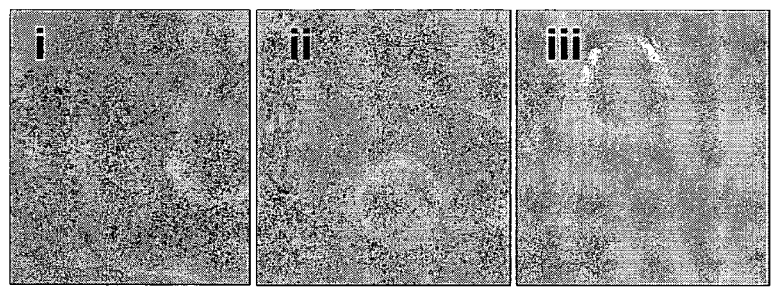
FIG. 6 shows the native apple promoter containing the minisatellite induces ectopic anthocyanin accumulation. (a) Shading shows that red colouration has developed around the infiltration site in the leaves of Nicotiana tabacum 8 days after transient transformation with $R_6$:MdMYB10 (i) and 35S: MdMYB10 (ii) but not with $R_1$. All three were co-infiltrated with 35S:MdbHLH3. (b) Regenerating Royal Gala apple callus transformed with $R_6$:MdMYB10. $R_1$=native promoter from Malus domestica 'Royal Gala'. $R_6$=native promoter from Malus×pumila var. niedzwetzkyana.
Figure 6:

Expression of the MdMYB10 Transcription Factor Driven by the Promoter of the Invention Results in Anthocyanin Production in Transiently Transformed Tobacco Previous studies have shown that when MdMYB10 was fused to 35S and co-infiltrated into *N. tabacum* with a 35S driven co-factor bHLH, a high level of anthocyanin pigmentation could be detected at the infiltration site (Espley et al, 2007, The Plant Journal 49, 414-427). The applicants therefore infiltrated *Nicotiana tabacum* with *Agrobacterium* suspensions of MdMYB10 driven by the $R_1$ and $R_6$ promoter sequences. $R_1$ is the native promoter from *Malus domestica* 'Royal Gala'. $R_6$ is the native promoter from *Malus×pumila* var. *niedzwetzkyana*. When $R_6$:MdMYB10 was co-infiltrated with 35S:MdbHLH3 a similar level of colouration was achieved as with 35S:MdMYB10 (FIG. 6A). The applicants were unable to detect anthocyanin accumulation with the $R_1$:MdMYB10 infiltration, with or without 35S:MdbHLH3.

To investigate the properties of the $R_6$ promoter in apple, the applicants transformed Royal Gala with MdMYB10 cDNA driven by either the $R_6$ or $R_1$ promoters. Whilst the R1 promoter is found in Royal Gala $R_6$ is not. It has previously been shown that when Royal Gala is transformed with 35S: MdMYB10, red callus is produced which regenerates to produce red plants (Espley et al, 2007, The Plant Journal 49, 414-427). The applicants observed a similar callus phenotype when Royal Gala is transformed with $R_6$:MdMYB10, with bright red areas on regenerating callus (FIG. 6B). However, whilst 35S:MdMYB10 was capable of driving anthocyanin accumulation in the transformed callus in the absence of light, we noted that the $R_6$:MdMYB10 transformants required light for the induction of pigmentation. No sustained pigmentation was seen on regenerating apple callus transformed with $R_1$:MdMYB10. Similarly, callus transformed with an empty vector cassette showed no pigmentation.

Example 5

Figure 7:
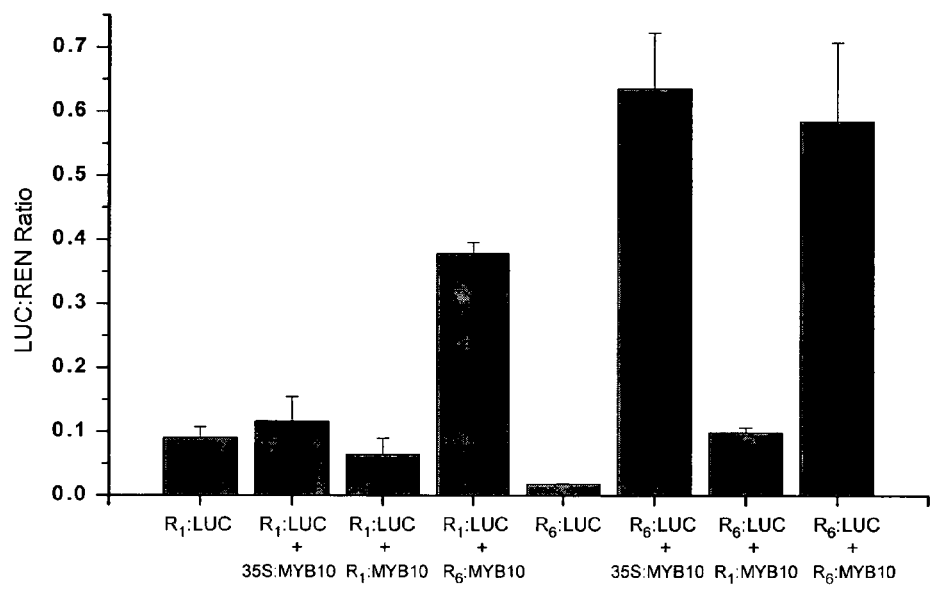
FIG. 7 shows the interaction of the native apple promoters and MdMYB10 in the dual luciferase transient tobacco assays. To compare the transactivation activity of the apple promoters to 35S, these were co-infiltrated with the $R_1$ and $R_6$ promoter-luciferase fusions. The results provide a measure for the potential activity of the apple promoters and they show a significant increase in the case of the $R_6$-driven MdMYB10. $R_1$=native promoter from Malus domestica 'Royal Gala'. $R_6$=native promoter from Malus×pumila var. niedzwetzkyana.

Expression of the MdMYB10 Transcription Factor Driven by the Promoter of the Invention Can Transactivate Reporter Gene Expression at a Level Similar or Higher than CaMV35S Promoter Driven Expression of the MdMYB10 Transcription Factor To further investigate the effect of the promoter on MdMYB10 transcript and predicted protein levels, the applicants repeated the assay from Example 2, replacing the 35S promoter with either the $R_1$ or $R_6$ promoters. Results indicated that the high transcript abundance of MdMYB10 driven by the $R_6$ promoter enables transactivation of the reporter, particularly when the reporter is fused to $R_6$ (FIG. 7). The results show a similar level of activity to the 35S promoter. With the $R_1$ luciferase fusion, $R_6$:MdMYB10 appears to exert stronger transactivation than 35S:MdMYB10. The $R_1$:MdMYB10 fusion did not influence transactivation to the same extent.

Example 6

The Number of Copies of the 23 bp Repeat Unit Influences Transcription

Figure 8:
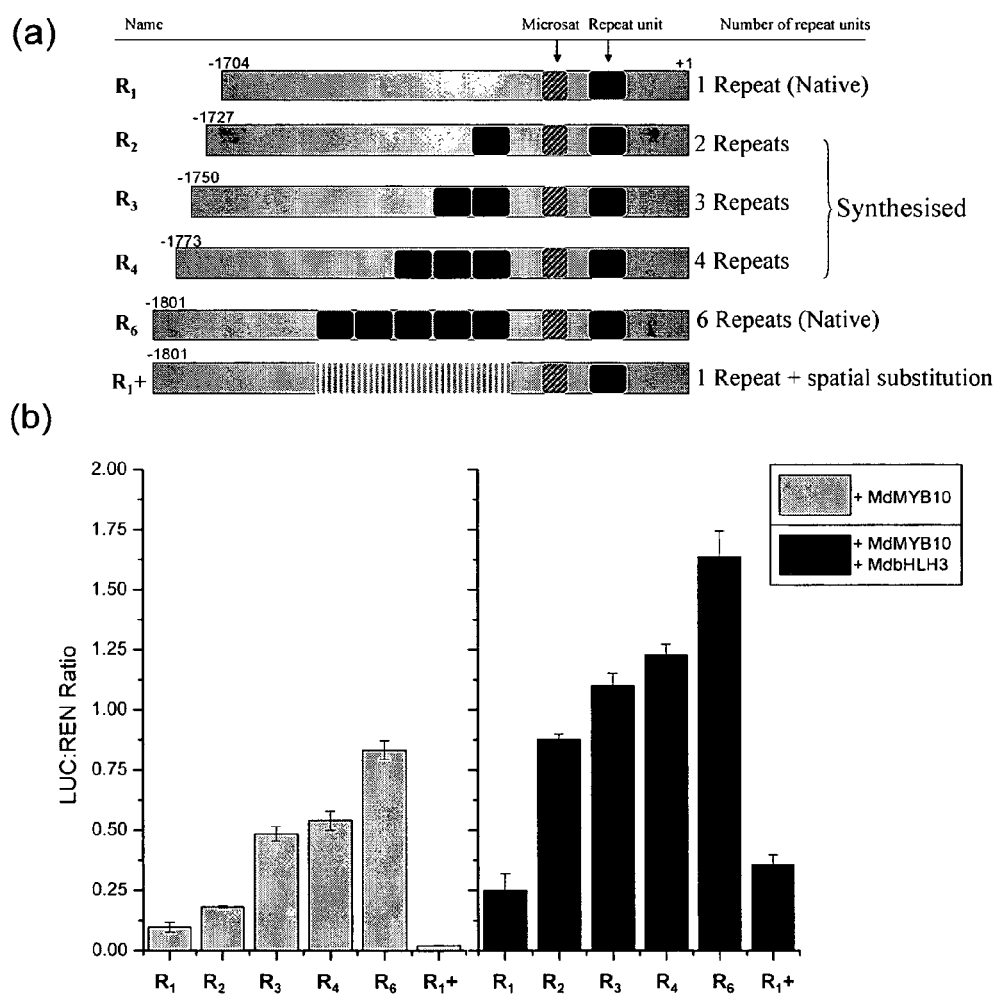
FIG. 8 shows the number of repeat units affects the transactivation rate. (a) Cartoon (not drawn to scale) of the different promoters with repeat units ranging from zero ($R_0$) to six ($R_6$). The two native promoters from apple are marked, $R_1$ as from Malus×domestica 'Royal gala' and R6 from Malus× pumila var. niedzwetzkyana. The position of the repeat units (in black) relative to the microsatellite (grey diagonal box) is shown. $R_1$+ is differentiated with grey vertical shading to represent the substituted sequence replacing the spatial effect of the minisatellite. (b) Results of $R_0$ to $R_6$ promoters co-infiltrated with 35S:MdMYB10 alone (light grey bars) and with 35S:MdMYB10 and 35SMdbHLH3 (dark grey bars). Error bars shown are means±S.E. of 6 replicate reactions.

A series of constructs were built, using standard molecular biology techniques, to test the effect on transcription of the number of 23 bp repeat units present in the upstream region. These constructs were based on the native promoter sequences but with repeat units ranging from one ($R_1$) to six ($R_6$) and were fused to the luciferase reporter as above (FIG. 8a). To test the spatial effect that the presence of the minisatellite sequence might exert on other non-identified motifs, a further construct ($R_1$+) was built where the minisatellite sequence from $R_6$ was replaced with non-specific DNA of the same length from a cloning vector (Promega, Madison, Wis., USA). The results indicate a correlation between the number of repeat units and the activation of the promoter (FIG. 8b). When co-infiltrated with 35S:MdMYB10 there is basal activity from both $R_1$ and $R_1$+ and an increasing activation from $R_2$ to $R_6$. There are numerous examples of the relationship between the anthocyanin-regulating MYB and bHLH co-factors and it has previously been shown the dependency of MdMYB10 on a co-factor bHLH in transient assays (Espley et al, 2007, The Plant Journal 49, 414-427). In this assay, activation for both the $R_1$ and $R_6$ promoters is enhanced with the addition of 35S:MdbHLH3 for all the constructs tested.

Example 7

Figure 9A:
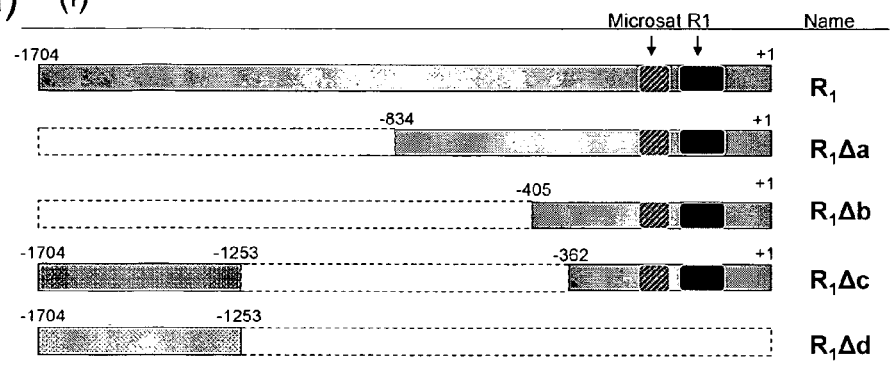
FIG. 9 shows identification of areas of the promoter critical to transactivation by deletion study. (a) Cartoon (not drawn to scale) of the different promoter deletions of $R_1$, (i) and $R_6$, (ii), denoted as Δa-Δd. Deleted areas are shown in white with dotted lines and the relative positions of the repeat unit $R_1$ to the microsatellite and minisatellite are displayed. (b) Corresponding data from promoter deletion studies with luciferase fusions of $R_1$, (i) and (ii), and $R_6$, (iii) and (iv), co-infiltrated with MdMYB10, (i) and (iii) respectively (pale grey bars) and with MdMYB10 and MdbHLH3, (ii) and (iv) respectively (dark grey bars). Error bars shown are means±S.E. of 6 replicate reactions.
Figure 9A:
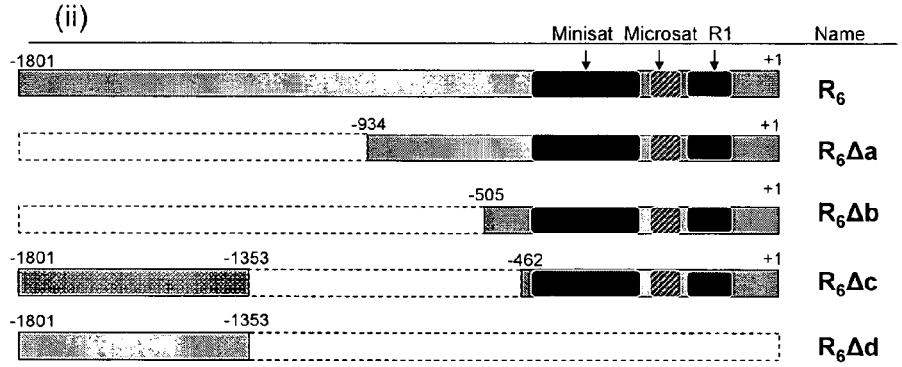

Deletion Analysis of the Promoter of the Invention Emphasises the Importance of the Minisatellite Region, Containing Multiple Copies of the 23 bp Repeat Unit, in Enhancing Transcription To define the upstream region directly responsible for transcriptional enhancement, both versions of the native promoter ($R_1$ and $R_6$) were subjected to various sequence deletion treatments (FIG. 9a). The five versions for each native promoter were fused to luciferase and co-infiltrated into tobacco with 35S:MdMYB10, +/−35S:MdbHLH3.

Figure 9B:
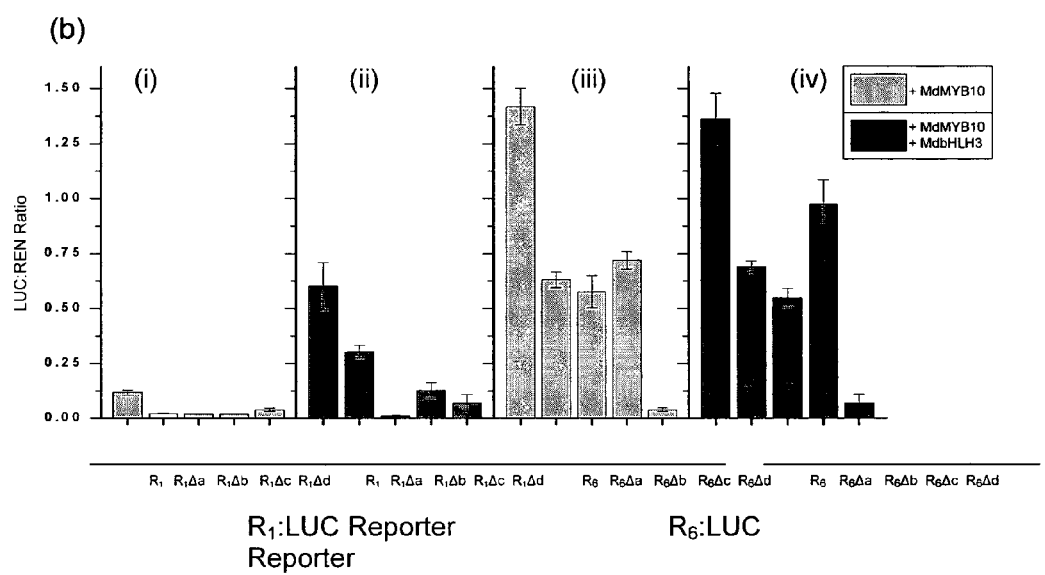

When the deletion versions of $R_1$:LUC were infiltrated with just 35S:MdMYB10, luciferase activity was barely detectable and significantly lower than the native non-deleted version (FIG. 9b). Only when 35S:MdbHLH3 was co-infiltrated with 35S:MdMYB10 did luminescence rise above background. Although there is a putative bHLH binding domain at the 5' end of the isolated promoter region, when this was deleted (R$_1$Δa) there was still a significant increase in LUC:REN ratio with co-infiltration of the bHLH, suggesting that there may be an alternative site for bHLH binding. The R$_6$:LUC deletions were less affected than R$_1$ with activity halved for R$_6$Δa and R$_6$Δb and a lesser reduction with R$_6$Δc. With the restoration of the putative bHLH binding domain on both R$_1$Δc and R$_6$Δc, there is an increase in activity when 35S:MdbHLH3 is co-infiltrated.

In this assay, the R$_6$:LUC promoters appeared to show a lesser dependence on the bHLH for increased activity although this may be due to saturation or depletion of one or other of the co-infiltrated transcription factors. For both R$_1$Δd and R$_6$Δd there was barely detectable activity, with or without the bHLH, confirming the requirement of the 3' region for transactivation. The data suggests that the R$_6$ promoter can still activate luciferase transcription in truncated form (500 bp) whereas the corresponding version of R$_1$ (R$_1$Δb) cannot.

Experimental Procedures

Isolation of MdMYB10 Upstream Promoter Region

For isolation of the upstream promoter region, genomic DNA was extracted from *Malus×domestica* 'Sciros' (Pacific Rose™, derived from a cross between 'Gala' and 'Splendour'). Nested primers were designed to the coding region of MdMYB10; primary 5'-CACTTTCCCTCTCCATGAATCT-CAAC-3 (SEQ ID NO: 18), and secondary 5'-CAG-GTTTTCGTTATATCCCTCCATCTC-3 (SEQ ID NO: 19). A 1.7 Kb region of upstream DNA, immediately adjacent to the transcription start site was isolated from the genomic DNA by PCR genome walking using a GenomeWalker™ kit (Clontech, Mountain View, Calif., USA), following the manufacturers instructions. Genomic DNA was subsequently isolated from *Malus×domestica* 'Granny Smith', *Malus×domestica* 'Royal Gala' and *Malus×pumila* var. *niedzwetzkyana* using forward and reverse primers 5'-ACCCTGAACACGTGG-GAACCG-3 (SEQ ID NO: 20) and 5'-GCTAAGCTTAGCT-GCTAGCAGATAAGAG-3 (SEQ ID NO: 21) respectively. The PCR products were cloned using the TOPO TA Cloning® kit (Invitrogen, Carlsbad, Calif., USA) and the sequences aligned using Vector NTI (Invitrogen).

Minisatellite Region PCR Amplification and Sequencing

Apple genomic DNA from 19 cultivars was amplified using a pair of PCR primers located in the MYB10 promoter (forward: 5'-GGAGGGGAATGAAGAAGAGG-3' [SEQ ID NO: 22]; reverse: 5'-TCCACAGAAGCAAACACTGAC-3' [SEQ ID NO: 23]). PCR reactions were carried out in 16.5 μl volume containing 1×PCR buffer mix (Invitrogen), 1.3 mM MgCl$_2$, 100 μM of each dNTP, 0.72% formamide, 10 μM of each primer, 0.5 U of Platinum Taq DNA polymerase (Invitrogen) and 2 ng of genomic DNA. PCR amplifications were performed in a Hybaid PCR Express Thermal Cycler (Thermo Electron Corporation, Waltham, Mass., USA) with conditions as follows: 94° C. for 2 min 45 sec followed by 40 cycles at 94° C. for 55 sec, 55° C. for 55 sec and 72° C. for 1 min 39 sec, and a final elongation at 72° C. for 10 min. The PCR products obtained were cloned using the TOPO TA Cloning® kit (Invitrogen). Four clones were sequenced for each PCR product. The sequences were aligned using Vector NTI (Invitrogen).

Plasmid Construction

Luciferase reporter constructs were derivatives of pGreen 0800-LUC (Hellens et al. 2005, Plant Methods 1, 13) in which the promoter sequence for the native MdMYB10 promoter or the deletion fragments were inserted. Native promoter sequences were PCR amplified using the primers 5'-ACCCTGAACACGTGGGAACCG-3' (SEQ ID NO: 24) and 5'-GCTAAGCTTAGCTGCTAGCAGATAAGAG-3' (SEQ ID NO: 25) and cloned into the multi-cloning region of pGreen 0800-LUC. R$_1$ and R$_6$ promoter fragments were cloned in as native promoter sequences whilst changes to the repeat frequency for the R$_2$, R$_3$ and R$_4$ promoter fragments were synthesised (Geneart AG, Regensburg, Germany) and cloned into R$_1$ using the restriction enzymes SpeI and DraI. An inverse PCR approach was used for the R$_1$+ construct with the inclusion of unique restriction sites (BamHI and SacI) for the cloning of non-specific DNA (from pGEM T Easy, Promega, Madison, Wis., USA) using the primers 5'-GGATCCTTCTGCACGACAACATTGACAA-3' (SEQ ID NO: 26) and 5'-GAGCTCATGTTAGCTTTTCTATATATCGA-3' (SEQ ID NO: 27). The pSAK construct for 35S:MdMYB10 and 35S:MdbHLH3 was as previously described (Espley et al, 2007, The Plant Journal 49, 414-427) whilst the promoter sequences were substituted for the R$_1$ and R$_6$:MdMYB10 versions. All constructs were verified by DNA sequencing.

Transactivation Analysis Using Transformed Tobacco Leaves

The promoter sequences for MdMYB10 were inserted into the cloning site of pGreen 0800-LUC (Hellens et al, 2005, Plant Methods 1, 13). In the same construct, a luciferase gene from *Renilla* (REN), under the control of a 35S promoter, provided an estimate of the extent of transient expression. Activity is expressed as a ratio of LUC to REN activity. The promoter-LUC fusions were used in transient transformation by mixing 100 μl of *Agrobacterium* strain GV3101 (MP90) transformed with the reporter cassette with or without another *Agrobacterium* culture(s) (900 μl) transformed with a cassette containing MYB10 fused to the 35S, R1 or R6 promoters and MdbHLH3 fused to the 35S promoter. *Nicotiana tabacum* 'Samsun' plants were grown until at least 6 leaves were available for infiltration with *Agrobacterium*. A 10 μl loop of confluent bacterium were re-suspended in 10 ml of infiltration media (10 mM MgCl2, 0.5 μM acetosyringone), to an OD$^{600}$ of 0.2, and incubated at room temperature without shaking for 2 h before infiltration. Approximately 150 μl of this *Agrobacterium* mixture was infiltrated at six points into a young leaf of *N. tabacum*. Transient expression was analysed three days after inoculation. Six technical replicates of 3 mm Ø leaf discs were excised from each plant using a leaf hole-punch and buffered in Phosphate Buffer Saline (PBS). Plate-based assays were conducted using a Berthold Orion Microplate Luminometer (Berthold Detection Systems, Oak Ridge, Tenn., USA) according to the manufacturer's specifications for the dual luciferase assay, using the Dual Glow assay reagents (Promega) for firefly luciferase and *renilla* luciferase. Luminescence was calculated using Simplicity version 4.02 software (Berthold Detection Systems).

Induction of Anthocyanin Pigmentation in Tobacco

*N. tabacum* were grown as previously mentioned and maintained in the glasshouse for the duration of the experiment. *Agrobacterium* cultures were incubated as for the dual luciferase assay and separate strains containing the MdMYB10 gene fused to either the 35S, R$_1$ or R$_6$ promoter sequences and the MdbHLH3 gene fused to the 35S promoter were mixed (500 μl each) and infiltrated into the abaxial leaf surface. Six separate infiltrations were performed into *N. tabacum* leaves (two plants per treatment) and changes in colour were observed over an eight day period. To control for leaf-to-leaf variability, at least 2 leaves were infiltrated, and each leaf included positive (*Agrobacterium* cultures containing 33S:MdMYB10+35S:MdbHLH3) and negative (*Agrobacterium* with empty vector) controls.

Transformation of Apple

The binary vector pSAK277 containing the MdMYB10 cDNA driven by the $R_6$ or $R_1$ promoters was transferred into *Agrobacterium tumefaciens* strain GV3101 by the freeze-thaw method. Transgenic *Malus domestica* 'Royal Gala' plants were generated by *Agrobacterium*-mediated transformation of leaf pieces, using a method previously reported (Yao et al. 1995, Plant Cell Reports, 14, 407-412).

Example 8

Isolation of the PcMYB10 Promoter from Pear and Identification of a Sequence Motif Analogous to the Repeat Motif Found in Apple MdMYB10 Promoters Isolation of the MYB10 Promoter from Pear Genomic DNA was isolated from the leaves of a pear cultivar (*Pyrus communis* 'William's Bon Chretien') using a Qiagen DNeasy Plant Mini Kit, according to the manufacturers instructions (Qiagen, Valencia, Calif.). Promoter sequences were isolated by PCR using the primers RE158 (5'-ACCCTGAACACGTGGGAACCG-3', SEQ ID NO: 28) and RE159 (5'-CTCTTATCTGCTAGCAGCTAAGCT-TAGC-3', SEQ ID NO: 29).

By comparing the sequences of the MYB10 promoter from apple (Example 1) and pear, the applicants identified presence of a 23 bp motif, in the pear promoter, very similar to that found in apple MYB10 proteins.

An alignment of the MYB10 promoter from the white-fleshed apple and from pear, highlighting the 23 bp motif with underligning, is shown in FIG. 12.

Both the apple and pear promoters showed some positional conservation with the R1 repeat being at position –220 (from the ATG site) in apple and position –227 in pear. Similarly, the position of the microsatellite appeared to be conserved with the microsatelite in apple starting at position –253 and in pear at –259.

The applicants identified three versions of the 23 bp element, from white-fleshed apple, red-fleshed apple and pear, as summarized in Table 2 below.

TABLE 2

Comparison of 23 bp motifs from apple and pear, highlighting variable positions

| SEQ ID NO | Sequence | Species found in |
|---|---|---|
| 1 | gttagac<u>t</u>ggtagcta<u>tt</u>aacaa | white-fleshed apple, red-fleshed apple |
| 11 | gttagac<u>t</u>ggtagcta<u>at</u>aacaa | white-fleshed apple |
| 12 | gttagac<u>c</u>ggtagcta<u>at</u>aacaa | pear |

Percent identity between the sequences is shown in Table 3 below.

TABLE 3

Percent identity between 23 bp motifs from apple and pear

| | SEQ ID NO: 1 | SEQ ID NO: 11 | SEQ ID NO: 12 |
|---|---|---|---|
| SEQ ID NO: 1 | 100% | 96% | 91% |
| SEQ ID NO: 11 | | 100% | 96% |
| SEQ ID NO: 12 | | | 100% |

The high degree of conservation between these three sequences, and their conserved position within the promoters, from three different sources, strongly suggest that each of the three sequences perform the same function.

Example 9

Production of a Chimeric Promoter with Altered Activity by Insertion of Copies of a Repeated Motif from the MdMYB10 Promoter from Red-Fleshed Apple into the PcMYB10 Promoter from Pear Introduction MdMYB10 controls the accumulation of anthocyanin in apple. Transient experiments described in the Examples above have shown that the MYB10 protein is able to auto-regulate its own promoter leading to a high level of expression of a Luciferase reporter gene driven by the long version of MdMYB10 promoter (which includes the 6 repeats of a putative transcription factor binding site), when co-infiltrated with bHLH33 transcription factor. The applicants have now introduced the 6 repeats into the green pear MYB10 promoter controlling luciferase reporter gene and assessed the reporter activity in presence of PcMYB10 and MdMYB10 TFs.

Materials and Methods

Figure 10:
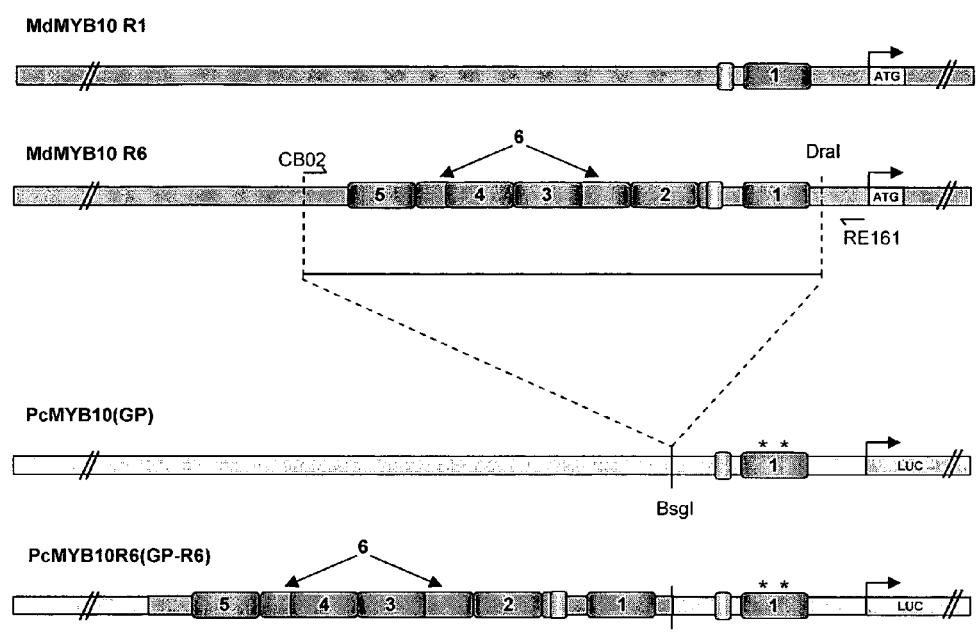
FIG. 10 shows a schematic representation of the cloning of the minsatellite repeat unit (copies 1-6) from the apple MdMYB10 $R_6$ promoter (MdMYB10 long) into the MYB10 promoter from pear (PcMYB10(GP)) to produce the chimeric promoter PcMYB10$R_6$(GP-R6). The MdMYB10 promoter from white-fleshed apple (MdMYB10 short) is included in the figure for reference. The position of the restriction sites (DraI and BsgI) and PCR priming sites (CB02 and RE161) is also shown.
Figure 11:
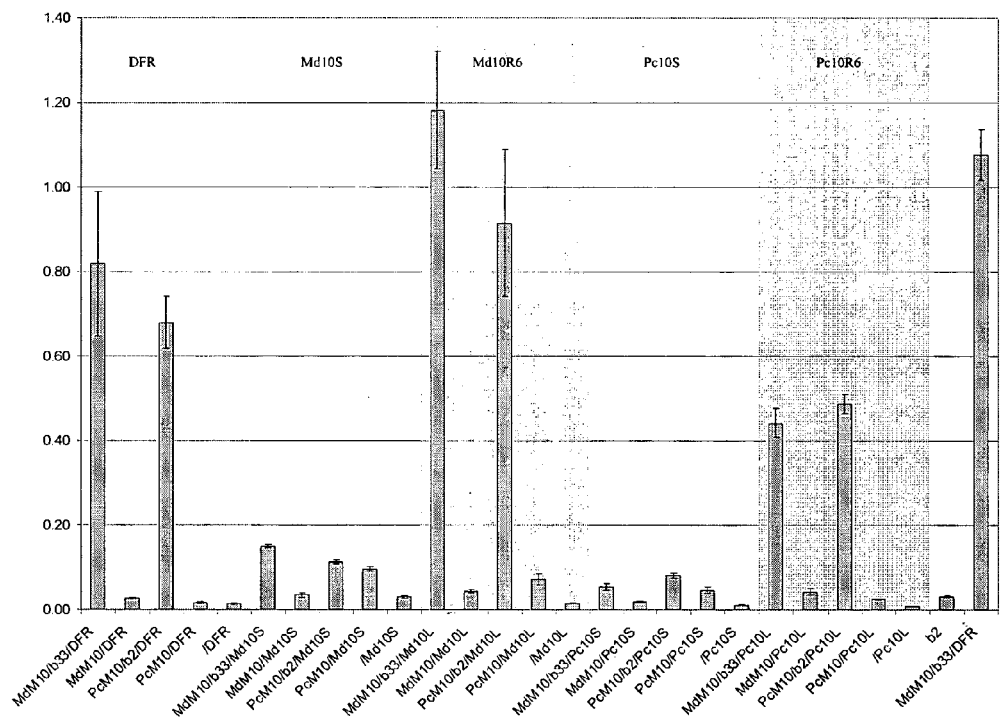
FIG. 11 shows the effect of MdMYB10 genomic and 35S: PcMYB10 constructs on luciferase reporter gene driven by PcMYB10 promoter containing or not the MdMYB10-promoter R6 repeats. Activity is expressed as a ratio of the Luciferase (LUC) to the CaMV35s-Renilla (REN) activities. Error bars represent the standard error (SE) for 4 replicates. All the promoter sequences were fused to the luciferase reporter and are abbreviated as follows: DFR, Arabidopsis DFR promoter; Md10s, MdMYB10 R1 promoter; Md10R6, MdMYB10 R6 promoter; Pc10S, PcMYB10R1 promoter and Pc10R6, PcMYB10R6 promoter. The transcription factor constructs are all driven by the CaMV35S promoter and are as follows: MdM10, MdMYB10; PcM10, PcMYB10; b33, MdbHLH33 and b2, Arabidopsis thaliana bHLH2.

The green pear MYB10 promoter (SEQ ID NO: 13) was cloned in the pGreen0800LUC vector. The R6 region (SEQ ID NO: 14) of the MdMYB10 promoter was amplified using primers CB02F/RE161, digested by Dra1 and cloned in the PcMYB10 promoter at the blunted Bsg1 site (see FIG. 10) to produce the recombinant chimeric promoter of SEQ ID NO: 15.

All the constructs (including MdMYB10 genomic, 35S: PcMYB10, AtbHLH2 and bHLH33 and the different LUC reporter constructs: DFR-LUC, MdMYB10short-LUC, MdMYB10long-LUC, PcMYB10short-LUC, PcMYB10R6-LUC) were transformed into GV3101 bp electroporation and used to infiltrate *Nicotiana benthaniama* leaves as described previously (Hellens at al. 2005, Plant Methods 1, 13). After 5 days, leaf discs were collected and Firefly luciferase (LUC) and *renillia* luciferase (REN) activities were measured on a luminometer using the Dual Glow™ reagents (PROMEGA).

Results

Apple and pear MYB10 constructs, in presence of bHLH33 and bHLH2 respectively, strongly activate the DFR, MdMYB10R6 and PcMYB10R6 promoters, and only slightly activate MdMYB10R1 and PcMYB10R1 promoters. The introduction of the apple R6 repeats in the pear promoter leads to a 6-fold increase in the luciferase activity in presence of the 35S:PcMYB10 construct and an 8-fold increase in presence of the MdMYB10 genomic construct.

Example 10

The MdMYB10 Promoter Containing 6 Copies of the 23 bp Repeat Unit is Activated by Several R2R3 Transcription Factor Sequences Introduction The effect of three MYB10 sequences (from pear [Pc-MYB10], strawberry [FaMYB10] and *Arabidopsis* [PAP1]) on two versions of the MdMYB10 promoter, R1 and R6, which contain 1 and 6 repeats of the 23 base pair repeat unit respectively, was measured using the transient transformation assay, described in previous examples, in tobacco.

Materials and Methods

R1 and R6 versions of MdMYB10 native promoter are as described previously (Espley et al., 2009, Plant Cell 21, 168-183). The R1 and R6 MdMYB10 promoters fused to the luciferase reporter are as described in Example 2.

MdMYB10 and bHLH3 coding sequences have been cloned in the pSAK binary vector as described previously (Espley et al., 2007, The Plant Journal 49, 414-427). The genomic coding sequence of PcMYB10 has been isolated from WBC pear genomic DNA and cloned in the pGreenII 0029 62-SK vector under the control of the 35S promoter. AtbHLH2 (EGL3, At1g63650) coding sequence has been isolated from *Arabidopsis* cDNA and cloned in the pHEX binary vector under the control of the 35S promoter. FaMYB10 coding sequence (SEQ ID NO: 33) has been isolated from *Fragaria ananassa* (garden strawberry) cDNA and cloned in the pGreenII 0029 62-SK binary vector under the control of the 35S promoter (Gleave, 1992, Plant Mol Biol 20, 1203-1207). MdMYB8 coding sequence has been isolated from *Malus domestica* 'Royal Gala' mature fruit cDNA and cloned in the pART277 binary vector (Gleave, 1992, (Gleave, 1992, Plant Mol Biol 20, 1203-1207). The coding sequences for AtPAP1 (Accession No. CAB09230), AtbHLH2 (Accession No. Q9CAD0) and MdbHLH3 (Accession No. CN934367) were also cloned upstream of the CaMV35 promoter as described for MdMYB10 here and in Example 2.

The promoter sequences for MYB10 were inserted into the cloning site of pGreen 0800-LUC (Hellens et al., 2005, Plant Methods 1, 13) to control the expression of the LUC reporter gene. In the same construct, a luciferase gene from REN, under the control of a 35S promoter, provided an estimate of the extent of transient expression. Activity is expressed as a ratio of LUC to REN activity. The promoter-LUC fusions were used in transient transformation of *Nicotiana benthamiana*. 0.1 mL of *Agrobacterium tumefaciens* strain GV3101 (MP90) transformed with the promoter-LUC cassette, was mixed with 0.45 mL of two other *Agrobacterium* cultures transformed with the 35S:MYB and 35S:bHLH constructs respectively. Infiltration of *N. benthamiana* leaf and chemiluminescence measurement are as described previously (Espley et al., 2007, The Plant Journal 49, 414-427).

Results

The results are shown in FIG. 13. The results from the assay indicate that the presence of the R6 motif in the apple MYB10 promoter leads to a large increase (7 to 12-fold) in luciferase activity in presence of the different MYB10 sequences when co-infiltrated with bHLH co-factor. No significant increase in luciferase activity was measured in presence of the MdMYB8 transcription factor (FIG. 13). These results show that the presence of the R6 motif confers the ability for the MdMYB10 promoter to be regulated by MdMYB10 and other R2R3MYBs (PcMYB10, FaMYB10 and PAP1).

Example 11

Chimeric Promoters Produced by Combining Copies of the 23 bp Repeat Unit and Naturally Occurring MYB10 Promoters Introduction To demonstrate production of functional chimeric promoters in the invention, the R6 domain from the apple MYB10 promoter was introduced in the pear MYB10 (see SEQ ID NO: 13) and *Arabidopsis* PAP1 (see SEQ ID NO: 36) promoters, 275 bp and 489 bp upstream of the ATG respectively (FIG. 15), and these constructs were assayed by the transient luminescent assay in tobacco.

Materials and Methods

The MdMYB10 R1 and R6 promoters are as described in Example 10. 4.6 Kb of PcMYB10 promoter (SEQ ID NO: 13) sequence was amplified from 'William Bon Chretien'(WBC) pear genomic DNA, 1.9 Kb of AtPAP1 (AtMYB75, AT1G56650) promoter sequence (SEQ ID NO: 36) was amplified from *Arabidospis* genomic DNA and cloned in the pGreen 0800-LUC vector (Hellens et al., 2005, Plant Methods 1, 13). The R6 domain was amplified from the 'Red Field' R6:MdMYB10 native promoter described previously (Espley et al., 2009, Plant Cell 21, 168-183), using primers CB02 5'-TGCAGAAATGTTAGACTGGTAGCTATTAAC-3' (SEQ ID NO: 30) and RE161 5'-CCAGTGACGTGCAT-GTCTGATATCC-3' (SEQ ID NO: 31). PCR fragment containing the R6 motif (as shown in FIG. 17) was digested with Dra1, gel purified and blunt-cloned in the PcMYB10 and AtPAP1 promoters at the BsgI and HindIII sites respectively to produce pPcMYB10R6-LUC and pAtPAP1R6-LUC constructs.

The sequence of the PcMYB10/R6 chimeric promoter is shown in SEQ ID NO: 15. The sequence of the AtPAP1/R6 chimeric promoter is shown in SEQ ID NO: 37.

MdMYB10 and bHLH3 coding sequences have been cloned in the pSAK binary vector as described previously (Espley et al., 2007, The Plant Journal 49, 414-427). The genomic coding sequence of PcMYB10 has been isolated from WBC pear genomic DNA and cloned in the pGreenII 0029 62-SK vector under the control of the 35S promoter. AtbHLH2 (EGL3, At1g63650) coding sequence has been isolated from *Arabidopsis* cDNA and cloned in the pHEX binary vector under the control of the 35S promoter.

Expression of the reporter genes under each promoter construct in the presence of the transcription factor constructs was tested in the transient assay as described in previous examples.

Results

The results are shown in FIG. 15. The results indicate that the presence of the R6 motif in the pear and the *Arabidopsis* promoters leads to an increase in luciferase activity when apple MYB10 and bHLH3 are co-infiltrated (FIG. 3). Similar results were obtained when these promoters are co-infiltrated with their corresponding MYB10 orthologs (i.e. pear promoter infiltrated with PcMYB10/bHLH2 and *Arabidospis* promoter infiltrated with AtPAP1/bHLH2). These results show that functional chimeric promoters can be produced by combining copies of the 23 bp repeat unit with naturally occurring R2R3 transcription factor (MYB10) promoters. The results also demonstrate autoregulation of the chimeric promoters by the product encoded by the gene with which the natural promoters are currently associated (i.e. the MYB10 transcription factor).

Example 12

Production of a Functional Chimeric Promoter by Combining Multiple Copies of the 23 bp Repeat Unit with an Unrelated Naturally Occurring Promoter, and Demonstration of Regulation of the Chimeric Promoter by R2R3MYB Transcription Factors Introduction The apple R6 motif was introduced into the promoter region of the VitC2 gene of *A. eriantha* 221 bp upstream of the 5'UTR (694 bp upstream of the ATG) (FIG. 14) and the construct was assayed as described in previous examples, in tobacco. VitC2 is a GDP-L-galactose guanyltransferase found to be a rate limiting step in ascorbic acid biosynthesis (Bulley et al., 2009, J Exp Bot 60, 765-778).

Materials and Methods 2.1 Kb of VitC2 promoter sequence (SEQ ID NO: 38) was amplified from *Actinidia eriantha* genomic DNA (Laing et al., 2007, Proc Natl Acad Sci USA 104, 9534-9539), and cloned in the pGreen 0800-LUC vector (Hellens et al., 2005, Plant Methods 1, 13). The R6 domain (SEQ ID NO: 14) was amplified from the 'Red Field' R6:MdMYB10 native promoter described previously (Espley et al., 2009, Plant Cell 21, 168-183), using primers CB02 5'-TGCAGAAATGTTA-GACTGGTAGCTATTAAC-3' (SEQ ID NO: 30) and RE161 5'-CCAGTGACGTGCATGTCTGATATCC-3' (SEQ ID NO: 31). PCR fragment containing the R6 motif (as shown in FIG. 17) was digested with Dra1, gel purified and blunt-cloned into the VitC2 promoters at the HpaI site to produce the pVitC2R6-LUC construct. Two tandem insertions of the R6 motifs were cloned in the VitC2 promoter to produce pVitC2R12-LUC. The sequence of the chimeric Vit C/R6 promoter is shown in SEQ ID NO: 39. The sequence of the chimeric VitC2/R12 promoter is shown in SEQ ID NO: 40.

MdMYB10 and bHLH3 coding sequences have been cloned in the pSAK binary vector as described previously (Espley et al., 2007, The Plant Journal 49, 414-427).

Expression of the reporter genes under each promoter construct in the presence of the transcription factor constructs was tested in the transient assay as described in previous examples.

Results

The results are shown in FIG. 16. The results indicate that the presence of the R6 motif in the VitC2 promoter leads to a significant increase in luciferase activity (up to 10-fold) when MdMYB10 and bHLH3 are co-infiltrated (FIG. 16). Interestingly, a higher number of repeats (R12) further increases the level of activation by MdMYB10 alone, although this effect is not seen when MdMYB10 and bHLH3 are co-infiltrated.

The above Examples illustrate practice of the invention. It will be appreciated by those skilled in the art that numerous variations and modifications may be made without departing from the spirit and scope of the invention.

SUMMARY OF SEQUENCES

| SEQ ID NO: | Sequence type | Information | Species |
|---|---|---|---|
| 1 | polynucleotide | 23 bp sequence motif, version 1 | *Malus domestica* and *Malus domestica niedwetzkyana* |
| 2 | polynucleotide | minisatellite repeat unit, from MdMYB10 promoter from red-fleshed cultivar *Malus × domestica niedwetzkyana*, including repeat motifs 2, 3A, 3B, 4, 5 and 6 | *Malus domestica niedwetzkyana* |
| 3 | polynucleotide | microsatellite | *Malus domestica niedwetzkyana* |
| 4 | polynucleotide | region of MdMYB10 promoter from red-fleshed cultivar *Malus × domestica niedwetzkyana* including minisatellite repeat unit, microsatellite and repeat unit 1 | *Malus domestica niedwetzkyana* |
| 5 | polynucleotide | whole MdMYB10 promoter from red-fleshed cultivar *Malus × domestica niedwetzkyana* | *Malus domestica niedwetzkyana* |
| 6 | polypeptide | MdMYB10 | *Malus domestica* |
| 7 | polynucleotide | MdMYB10 coding region | *Malus domestica* |
| 8 | polynucleotide | whole MdMYB10 promoter from white-fleshed cultivar *Malus domestica* Royal Gala | *Malus domestica* |
| 9 | polynucleotide | forward primer | artificial |
| 10 | polynucleotide | reverse primer | artifical |
| 11 | polynucleotide | 23 bp sequence motif, version 2 | *Malus domestica* |
| 12 | polynucleotide | 23 bp sequence motif, version 3 | *Pyrus communis* |
| 13 | polynucleotide | whole pear PcMYB10 promoter | *Pyrus communis* |
| 14 | polynucleotide | apple minisatellite sequence that was inserted into pear (PcMYB10), *Arabidopsis* (PAP1) and kiwifruit (VitC2) promoters | *Malus domestica niedwetzkyana* |
| 15 | polynucleotide | Chimeric apple/pear promoter | artificial |
| 16 | polypeptide | Pear PcMYB10 | *Pyrus communis* |
| 17 | polynucleotide | Pear PcMYB10 coding sequence | *Pyrus communis* |
| 18 | polynucleotide | Primer | artificial |
| 19 | polynucleotide | Primer | artificial |
| 20 | polynucleotide | Primer | artificial |
| 21 | polynucleotide | Primer | artificial |
| 22 | polynucleotide | Primer | artificial |
| 23 | polynucleotide | Primer | artificial |
| 24 | polynucleotide | Primer | artificial |
| 25 | polynucleotide | Primer | artificial |
| 26 | polynucleotide | Primer | artificial |
| 27 | polynucleotide | Primer | artificial |
| 28 | polynucleotide | Primer | artificial |
| 29 | polynucleotide | Primer | artificial |
| 30 | polynucleotide | Primer | artificial |
| 31 | polynucleotide | Primer | artificial |
| 32 | polypeptide | Strawberry FaMYB10 | *Fragaria ananassa* |
| 33 | polynucleotide | Strawberry FaMYB10 coding sequence | *Fragaria ananassa* |

-continued

| SEQ ID NO: | Sequence type | Information | Species |
|---|---|---|---|
| 34 | polypeptide | *Arabidopsis* PAP1 | *Arabidopsis thaliana* |
| 35 | polynucleotide | *Arabidopsis* PAP1 coding sequence | *Arabidopsis thaliana* |
| 36 | polynucleotide | *Arabidopsis* PAP1 promoter | *Arabidopsis thaliana* |
| 37 | polynucleotide | Chimeric PAP1 R6 promoter | artificial |
| 38 | polynucleotide | Kiwifruit VitC2 promoter | *Actinidia eriantha* |
| 39 | polynucleotide | Chimeric VitC2 R6 promoter | artificial |
| 40 | polynucleotide | Chimeric VitC2 R6 promoter | artificial |
| 41 | polynucleotide | consensus motif | artificial |
| 42 | polynucleotide | consensus motif | artificial |

The invention claimed is:

1. A method for producing a chimeric promoter polynucleotide capable of controlling transcription of an operably linked polynucleotide in a plant cell or plant, wherein the method comprising combining:
   a) at least one sequence motif consisting of a sequence with at least 90% identity to SEQ ID NO: 1, 11, or 12, and
   b) a promoter polynucleotide sequence,
   wherein the chimeric promoter polynucleotide is modulated by a MYB transcription factor and wherein the squence of the chimeric promoter polynucleotide is not a naturally occurring sequence.

2. The method of claim 1 in which the at least one sequence motif in a) consists of a sequence with at least 90% identity to the sequence of SEQ ID NO: 1.

3. The method of claim 1 in which the at least one sequence motif in a) consists of the sequence of SEQ ID NO:41.

4. The method of claim 1 in which the at least one sequence motif in a) consists of the sequence of SEQ ID NO:42.

5. The method of claim 1 in which at least two sequence motifs in a) are combined with the polynucleotide sequence in b), and in which at least one of the sequence motifs is interrupted by at least one of the other sequence motifs.

6. The method of claim 1 in which the polynucleotide in b) is a promoter polynucleotide sequence that naturally occurs in a plant.

7. The method of claim 1 in which the polynucleotide in b) is a promoter polynucleotide and comprises a sequence with at least 90% identity to one of the sequences of SEQ ID NO:13, 36 and 38.

8. The method of claim 1 in which the chimeric promoter polynucleotide is produced by combining:
   a) a sequence with at least 90% identity to the sequence of SEQ ID NO: 14, and
   b) a sequence with at least 90% identity to one of the sequences of SEQ ID NO: 13, 36 and 38.

9. A chimeric promoter polynucleotide produced by the method of claim 1.

10. A chimeric promoter polynucleotide capable of controlling transcription of an operably linked polynucleotide in a plant cell or plant, wherein the chimeric promoter polynucleotide comprises:
    a) at least one sequence motif consisting of a sequence with at least 90% identity to SEQ ID NO: 1, 11, or 12, and
    b) a promoter polynucleotide sequence,
    wherein the chimeric promoter polynucleotide is modulated by a MYB transcription factor and wherein the sequence of the chimeric promoter polynucleotide is not a naturally occurring sequence.

11. The chimeric promoter polynucleotide of claim 10 in which the at least one sequence motif in a) consists of a sequence with at least 90% identity to the sequence of SEQ ID NO: 1.

12. The chimeric promoter polynucleotide of claim 10 in which the at least one sequence motif in a) consists of the sequence of SEQ ID NO:41.

13. The chimeric promoter polynucleotide of claim 10 in which the at least one sequence motif in a) consists of the sequence of SEQ ID NO:42.

14. The chimeric promoter polynucleotide of claim 10 in which the chimeric promoter polynucleotide comprises at least two of the sequence motifs in a) and in which the at least one of the sequence motifs is interrupted by at least one of the other sequence motifs.

15. The chimeric promoter polynucleotide of claim 10 in which the at least one sequence motif in a) is part of a promoter polynucleotide sequence that naturally occurs in a plant.

16. The chimeric promoter polynucleotide of claim 10 in which the promoter polynucleotide in b) is a promoter polynucleotide sequence that naturally occurs in a plant.

17. The chimeric promoter polynucleotide of claim 10 in which the promoter polynucleotide comprises a sequence with at least 90% identity to one of the sequences of SEQ ID NO:13, 36 and 38.

18. The chimeric promoter polynucleotide of claim 10 comprising:
   a) a sequence with at least 90% identity to the sequence of SEQ ID NO:14, and
   b) a sequence with at least 90% identity to one of the sequences of SEQ ID NO:13, 36 and 38.

19. The chimeric promoter polynucleotide of claim 10 comprising a sequence with at least 90% identity to SEQ ID NO:15.

20. The chimeric promoter polynucleotide of claim 10, wherein the chimeric promoter polynucleotide is positively modulated, or activated, or up-regulated by the MYB transcription factor.

21. The chimeric promoter polynucleotide of claim 10, wherein the chimeric promoter polynucleotide is capable of controlling transcription of an operably linked polynucleotide constitutively in substantially all tissues of a plant.

22. The chimeric promoter polynucleotide of claim 10, wherein the chimeric promoter polynucleotide is capable of controlling transcription of an operably linked polynucleotide in any plant, plant cell, or plant tissue in which the MYB transcription factor is expressed.

23. The chimeric promoter polynucleotide of claim 10 comprising a sequence with at least 90% identity to any one of SEQ ID NO: 15, 37, 39 and 40.

24. A genetic construct comprising a chimeric promoter polynucleotide of claim 10.

25. A host cell transformed with the chimeric promoter polynucleotide of claim 10.

26. A plant cell or plant transformed with the chimeric promoter polynucleotide of claim 10.

27. A plant cell or plant transformed with a genetic construct of claim 24.

28. The plant cell or plant of claim 26, that is also transformed with a polynucleotide or genetic construct for expressing a MYB transcription factor that modulates expression of the chimeric promoter polynucleotide.

29. The plant cell or plant of claim 26, which naturally expresses a MYB transcription factor that modulates expression of the chimeric promoter polynucleotide.

30. A method for producing a plant cell or plant with modified expression of at least one polynucleotide, the method comprising transformation of the plant cell or plant with the chimeric promoter polynucleotide of claim 10.

31. The method of claim 30, in which the plant cell or plant is also transformed with a polynucleotide or genetic construct capable of expressing a MYB transcription factor that modulates expression of the chimeric promoter polynucleotide.

32. The method of claim 30, in which the plant cell or plant naturally expresses a MYB transcription factor that modulates expression of the chimeric promoter polynucleotide.

33. A plant cell or plant produced by the method of claim 30.

34. A seed, propagule, progeny, part, fruit or harvested material of the plant of claim 26, wherein said seed, propagule, progeny, part, fruit or harvested material comprises said chimeric promoter polynucleotide.

35. A seed, propagule, progeny, part, fruit or harvested material of a plant comprising the chimeric promoter polynucleotide of claim 11, wherein said seed, propagule, progeny, part, fruit, or harvested material comprises said chimeric promoter polynucleotide.

* * * * *

UNITED STATES PATENT AND TRADEMARK OFFICE
CERTIFICATE OF CORRECTION

PATENT NO.       : 8,686,125 B2  
APPLICATION NO. : 12/992543  
DATED            : April 1, 2014  
INVENTOR(S)      : Espley et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 477 days.

Signed and Sealed this

Twenty-ninth Day of September, 2015

Michelle K. Lee  
*Director of the United States Patent and Trademark Office*

SEQUENCE LISTING

```
<160> NUMBER OF SEQ ID NOS: 44

<210> SEQ ID NO 1
<211> LENGTH: 23
<212> TYPE: DNA
<213> ORGANISM: Malus domestica

<400> SEQUENCE: 1
gttagactgg tagctattaa caa                                               23

<210> SEQ ID NO 2
<211> LENGTH: 118
<212> TYPE: DNA
<213> ORGANISM: Malus domestica niedwetzkykyana

<400> SEQUENCE: 2
gttagactgg tagctattaa caagttagac tggttagact ggtagctatt aacaagttag       60
actggtagct attaacaact ggtagctatt aacaagttag actggtagct attaacaa        118

<210> SEQ ID NO 3
<211> LENGTH: 13
<212> TYPE: DNA
<213> ORGANISM: Malus domestica niedwetzkyana

<400> SEQUENCE: 3
gtgtgtgtgt gtg                                                          13

<210> SEQ ID NO 4
<211> LENGTH: 172
<212> TYPE: DNA
<213> ORGANISM: Malus domestica niedwetzkyana

<400> SEQUENCE: 4
gttagactgg tagctattaa caagttagac tggttagact ggtagctatt aacaagttag       60
actggtagct attaacaact ggtagctatt aacaagttag actggtagct attaacaagt      120
tagactgtgt gtgtgtgtgt atttcacaag ttagactggt agctattaac aa              172

<210> SEQ ID NO 5
<211> LENGTH: 1795
<212> TYPE: DNA
<213> ORGANISM: Malus domestica niedwetzkyana

<400> SEQUENCE: 5
taccctgaac acgtgggaac cggcccgttt gtaacagact gagataggtc cggttctatt       60
tcttaaaaac ccaacacccg ctacgttcca tttataaacg ggtcggtctg gtccctccaa      120
```

-continued

```
ctttgagccc ggctcgactt gtgcccactc ctaaactaaa ccatataaaa accaagattt    180
cccttcatc tttcacacat atcacgttac tttccaacaa caattcaaca atcacaacaa    240
ataatcaacc atcaagatca tatatcacgt cactaataaa gacaaccttc ataagggttg    300
ccgtagttct ctacttgaaa tccaattgtc tagcattgta accctaagtt acagacacaa    360
acataaactt gagcaacttc tatgcataag aatctagggt tttggactaa ctcaacagaa    420
cctaacaaga aataatattc tggaccgctt aacggaatcc aacgaagaca aggtttcgga    480
ccactcaacg gaacaaataa gggaaaggga tataaaccat caacgaaat  ccatctttag    540
aatacgcata gtcccccaat acggattaac caagtgagaa catacgccat ctgatagcgt    600
ggtcccgcaa gacagttaac caagtaggac caccgatggt ataatgtgac caagtaagca    660
gtgaccctaa atgtagatta accacgtgga gttaaattaa caaggctgaa ccacctatga    720
aaataatgta agcctgaaat cttaggagag aattcttgct ctaggggaca aatgattttc    780
gtatgcctaa gtgttttttt agtgacagta aactaagatt tgagtacaga gacattaact    840
gagattgact cttgtgaaag cttagtgagt tgaagcacgt agccaattat attgagcaat    900
gtgttaggtg tagcgtctaa acttccgtag gagttttgta cagcaatata gtgggggtgc    960
cgcaaaatgc agacagtagc aataaattac gggctaggat tttctcctct ttttttttcg   1020
ttccattcca tccattcctc tcacattctt tattttgtct ttctctttct ataaaaatt   1080
aatataagat gttaatgtaa cttgaccgtg actattcaaa taggagggga atgaagaaga   1140
gggaaaaaaa gagaggagag aatcctactc cgtaaattac aagcaaacac tttttttttt   1200
tttggacaag cagaagcaaa caaacacttg aaaaagcagc gaaagcatga taaaggtatc   1260
ttatggtggt caaagatgtg tgttgtaact agttacacga ttctgcattc acattcatag   1320
aatgtgcttt tgaatattat attacagcta gagaattta tgccctggga ttgatttccc   1380
ttgtcaatgt tgtcgtgcag aaatgttaga ctggtagcta ttaacaagtt agactggtta   1440
gactggtagc tattaacaag ttagactggt agctattaac aactggtagc tattaacaag   1500
ttagactggt agctattaac aagttagact gtgtgtgtgt gtgtatttca caagttagac   1560
tggtagctat taacaactgt tggaatgttt taaacttgtc agtgtttgct tctgtggata   1620
tcagacatgc acgtcactgg ccttgtaaga ttaattaggc cgatggtatc catagcgtta   1680
acgtcatggc aaacacactc taattatata taatggtagc taggtgtctt tctggagtct   1740
atgaagtggg tagcaggcaa aagataagct aagcttagct gctagcagat aagag        1795
```

<210> SEQ ID NO 6
<211> LENGTH: 243
<212> TYPE: PRT
<213> ORGANISM: Malus domestica

<400> SEQUENCE: 6

```
Met Glu Gly Tyr Asn Glu Asn Leu Ser Val Arg Lys Gly Ala Trp Thr
1               5                   10                  15

Arg Glu Glu Asp Asn Leu Leu Arg Gln Cys Val Glu Ile His Gly Glu
            20                  25                  30

Gly Lys Trp Asn Gln Val Ser Tyr Lys Ala Gly Leu Asn Arg Cys Arg
        35                  40                  45

Lys Ser Cys Arg Gln Arg Trp Leu Asn Tyr Leu Lys Pro Asn Ile Lys
    50                  55                  60

Arg Gly Asp Phe Lys Glu Asp Glu Val Asp Leu Ile Ile Arg Leu His
65                  70                  75                  80

Arg Leu Leu Gly Asn Arg Trp Ser Leu Ile Ala Arg Arg Leu Pro Gly
```

```
                85                  90                  95
Arg Thr Ala Asn Ala Val Lys Asn Tyr Trp Asn Thr Arg Leu Arg Ile
            100                 105                 110

Asp Ser Arg Met Lys Thr Val Lys Asn Lys Ser Gln Glu Met Arg Glu
        115                 120                 125

Thr Asn Val Ile Arg Pro Gln Pro Gln Lys Phe Asn Arg Ser Ser Trp
    130                 135                 140

Tyr Leu Ser Ser Lys Glu Pro Ile Leu Asp His Ile Gln Ser Ala Glu
145                 150                 155                 160

Asp Leu Ser Thr Pro Pro Gln Thr Ser Ser Thr Lys Asn Gly Asn
                165                 170                 175

Asp Trp Trp Glu Thr Leu Leu Glu Gly Glu Asp Thr Phe Glu Arg Ala
            180                 185                 190

Ala Tyr Pro Ser Ile Glu Leu Glu Glu Leu Phe Thr Ser Phe Trp
        195                 200                 205

Phe Asp Asp Arg Leu Ser Pro Arg Ser Cys Ala Asn Phe Pro Glu Gly
    210                 215                 220

His Ser Arg Ser Glu Phe Ser Phe Ser Thr Asp Leu Trp Asn His Ser
225                 230                 235                 240

Lys Glu Glu

<210> SEQ ID NO 7
<211> LENGTH: 729
<212> TYPE: DNA
<213> ORGANISM: Malus domestica

<400> SEQUENCE: 7
atggagggat ataacgaaaa cctgagtgtg agaaaaggtg cctggactcg agaggaagac    60
aatcttctca ggcagtgcgt tgagattcat ggagagggaa agtggaacca agtttcatac   120
aaagcaggct taaacaggtg caggaaaagt tgcagactta gatggttgaa ttatttgaag   180
ccaaatatca agagaggaga cttaaagag atgaagtag atcttataat tagacttcac    240
aggcttttgg gaaacaggtg gtcattgatt gctagaagac ttccaggaag aacagcaaat   300
gctgtgaaaa attattggaa cactcgattg cggatcgatt ctcgcatgaa acggtgaaa    360 aataaatctc aagaaatgag agagaccaat gtgataagac ctcagcccca aaaattcaac   420
agaagttcat attacttaag cagtaaagaa ccaattctag accatattca atcagcagaa   480
gatttaagta cgccaccaca aacgtcgtcg tcaacaaaga atggaaatga ttggtgggag   540
accttgttag aaggtgagga tacttttgaa agagctgcat atcccagcat tgagttagag   600
gaagaactct tcacaagttt ttggtttgat gatcgactgt cgccaagatc atgcgccaat   660
tttcctgaag acatagtag aagtgaattc tcctttagca cggacctttg gaatcattca    720
aaagaagaa                                                           729

<210> SEQ ID NO 8
<211> LENGTH: 1696
<212> TYPE: DNA
<213> ORGANISM: Malus domestica

<400> SEQUENCE: 8
accctgaaca cgtgggaacc ggcccgtttg taaccgactg agataggtcc ggttctattt    60
cttaaaaacc caacaccccgc tatgttctat ttataaacgg gtccggtctg gtccctccaa   120
ctttgagccc ggctcgactt gtgcccactc taaactaaa ccatataaaa accaagattt     180
cccttttctt ctttcacaca tatcacgtta ctttccaaca acaattcaac aatcacaaca   240
```

```
aataatcaac catcaagatc atatatcacg tcactaataa agacaacctt cacaagggtt      300
gtcgtagttc tctactggaa atccaattgt ctagcattgt aaccctaagt tacagacaca      360
aacataaact tgagcaactt ctatgcataa gaatctgggg ttttggacta actcaacaga      420
acctaacaag aaataatatt ctggaccgct taacggaatc caacgaagac aaggtttcgg      480
accactcaac ggaacaaata agggaaaggg atataaacca ttcaacgaaa tccatcttta      540
gaatacgcat agtctcccaa tacgattaa ccaagtgaga acatacgcca tctgatagcg       600
tggtcccgca agacagataa ccaagtagga ccaccgatgg tataatgtga ccaagtaagc      660
agtgacccta aatgtagatt aaccacatgg agttaaatta acaaggctga accacctatg      720
aaaataatgt aagcctgaaa tcttaggaga gaattcttgc tctagggac aaatgatttt       780 cgtatgccta agtgtttttt tagtgacagt aaactaagat ttgagtacag agacattaac      840
tgagattgac tcttgtgaaa gcttagtgag ttgaagcacg taggccaatt atattgagca      900
atgtgttagg tgtagcgtct aaacttccgt aggagttttg tacagcaata tagtgggggt      960
gccgcaaaat gcagacagta gcaataaatt acgggctagg attttctcct cttttttttt     1020
cgttccattc catccattcc tctcacattt tttattttgt ctttctcttt ctataaaaaa     1080
ttaatataag atgttaatgt aacttgaccg tgactattca aataggaggg gaatgaagaa     1140
gagggaaaaa aaggagagaa tcctactcca taaattacaa gcaaacactt ttttttttt     1200 tttgacaagc agaagcaaac aaacacttga aaagcagcg aaagcatgat aaaggtatct      1260
tatggtggtc aaagatgtgt gttgtaacta gttacacgat tctgcattca cattcataga     1320
atgtgctttt gaatattata ttacagctag agaatttat gccctgggat tgatttccct      1380
tgtcaatgtt gtcgtgcaga aatgttagct tttctatata tcgagtgtgt gtgtgtgtgt     1440
gtatttcaca agttagactg gtagctaata acaactgttg gaatgtttta aacttgtcag     1500
tgtttgcttc tgtggatatc agacatgcac gtcactggcc ttgtaagatt aattaggccg     1560
atggtatcca tagcgttaat gtcatggcaa acacactcta attatatata atggtagcta     1620
ggtgtctttc tggagtgtat gaagtgggta gcaggcaaaa gaatagctaa gcttagctgc     1680
tagcagataa gagatg                                                     1696

<210> SEQ ID NO 9
<211> LENGTH: 20
<212> TYPE: DNA
<213> ORGANISM: Artificial Sequence
<220> FEATURE:
<223> OTHER INFORMATION: Synthetic construct: primer

<400> SEQUENCE: 9
ggagggggat gaagaagagg                                                    20

<210> SEQ ID NO 10
<211> LENGTH: 21
<212> TYPE: DNA
<213> ORGANISM: Artificial Sequence
<220> FEATURE:
<223> OTHER INFORMATION: Synthetic construct: primer

<400> SEQUENCE: 10
tccacagaag caaacactga c                                                  21

<210> SEQ ID NO 11
<211> LENGTH: 23
<212> TYPE: DNA
<213> ORGANISM: Malus domestica
```

<400> SEQUENCE: 11
gttagactgg tagctaataa caa                                              23

<210> SEQ ID NO 12
<211> LENGTH: 23
<212> TYPE: DNA
<213> ORGANISM: Pyrus communis

<400> SEQUENCE: 12
gttagaccgg tagctaataa caa                                              23

<210> SEQ ID NO 13
<211> LENGTH: 2001
<212> TYPE: DNA
<213> ORGANISM: Pyrus communis

<400> SEQUENCE: 13

```
ggtgttgagg gggagtgttg aagatcaaca ccagcccaat tggtgtttgt gttgaagtgt        60
aatcttgcct tggcccaaga tggatcgaac ccatggacaa agaaatatcc atacacatgc       120
tagaaaattc tagcaaagtt caagttggtg aacagtttta aagaatggt gaggagaagg        180
catccacacc atctgtatca attaagaaga ctaagtgaga gtgagaagta ggagtagtct       240
tgtgaggagt gtgagtggtc taaagttttgt ctctagaaag agtgagtgtc atagcttcaa      300
atagtgtctt tgagagtttg tgtgctataa tattttgtga gttaatacaa gtaattgttt       360
acttgtgttg tctctccaac acttgtgtta aagttgtgta ctctaagttt tccccaacat       420
atatcacttc actaataaag acaaccttcg taagggttgc cgtagttctc tacttgaaat       480
ccaattatct agcattgtaa ccctaagtta cagacacaaa cataaacttg agcaacttct       540
atgcataaga atctagggtt tcagactaac tcaatggaac ctaacaagaa ataatatccg       600
gaccgctaac gatgcatcca atcgaagaca aggtttcgga cactcaacgg aacaaataag       660
ggaaaaggat ataaaccact caacgaagtt catctctaga atacgtatag tccccaatac       720
ggattaacca gtgagaaaca tacaccatct aatagcatgg tcctgcaaga tagataacta       780
ggtaggacca ccgatggtat aatgtgacca agtaagtagt gaccctaaat gtagattaac       840
caagtggagt taaatttaga atgcatatgc accctacccc cccaagacag actaaccagg       900
cagaaccata tgcattcccc caatagtgtg gttccttaat gcagattgac aaggcggaac       960
cacctatgaa aataatgtaa ctaggtaggg cccgacgaat atctattgcc tgaaatctta      1020
ggagagaatt cttgctctag gggacaaatg atttttcgtat gcctaagtat ttttttattta    1080
gtgcacagtaa actaagattt gagtacagag acattaactg agattgactc ttgtgaaagc     1140
ttagtgagtt gaagcactta ggccaattat attgagcaat gtgttaggtg tagcgtctaa      1200
acttccgtag gagttttttta caacaagata gtggggtgc cgcaaaatgc agacagtagc      1260
aataaattac gggctaggat tatctcccct cgttttttg ttccattcca tcccttcctc       1320
tcacattctc tattttgtct ttcttttct aaaaaaatt aatataagat gttgatatag        1380
cttaaccggg accgttcaaa taagagggga aggaagaaga ggaaaaaaaa aagagaggaa      1440
ggaagaagag gaaaaaaaaa aaaagagaga gggaagagat tttactttat aaattacaag     1500
cagacacttt ttgttttttt tttttttga caaggagaag caaacaaaca cttgaaaaag       1560
cagcgaaagc aggctaaagg tatcttatgg tggtcaaaga tgtgtgttgt aactagttac     1620
acgattctgc cttcacattc atagaatgtg cttttgaata ttatattaca gctagagaat    1680
ttgatgtctt aggaatgttg tcgtgcagaa atgtcagctt ttctatatat agcgtgtgtg    1740
```

```
tatttcacaa gttagaccgg tagctaataa caactgttga aatgtttcaa acgtgtcact      1800
gtttgcttct gtggatatca gacatgcacg tcactggcct tggaagatta attagtccga      1860
tggtatccat agcgttaacg tcatggcaaa cacactctaa atatatatat atatataatg      1920
gtagctaggt gtctttctgg agtatgaagt gggtagcagg caaaagataa gctaagttta      1980
gctgctagca gatacgagat g                                                2001

<210> SEQ ID NO 14
<211> LENGTH: 195
<212> TYPE: DNA
<213> ORGANISM: Malus domestica niedwetzkyana

<400> SEQUENCE: 14
ctgcagaaat gttagactgg tagctattaa caagttagac tggttagact ggtagctatt        60
aacaagttag actggtagct attaacaact ggtagctatt aacaagttag actggtagct       120
attaacaagt tagactgtgt gtgtgtgtat ttcacaagtt agactggtag ctattaacaa       180
ctgttggaat gtttt                                                        195

<210> SEQ ID NO 15
<211> LENGTH: 2199
<212> TYPE: DNA
<213> ORGANISM: Artificial Sequence
<220> FEATURE:
<223> OTHER INFORMATION: Synthetic construct:  chimeric promoter

<400> SEQUENCE: 15
gagttggtgt tgagggggag tgttgaagat caacaccagc ccaattggtg tttgtgttga        60
agtgtaatct tgccttggcc caagatggat cgaacccatg gacaaagaaa tatccataca       120
catgctagaa aattctagca aagttcaagt tggtggaaca gtttagaaga atggtgagga       180
gaaggcatcc acaccatctg tatcaattaa gaagactaag tgagagtgag aagtaggagt       240
agtcttgtga ggagtgtgag tggtctaaag tttgtctcta gaaagagtga gtgtcatagc       300
ttcaaatagt gtctttgaga gttttgtgtgc tataatattt tgtgagttaa tacaagtaat       360
tgtttacttg tgttgtctct ccaacacttg tgttaaagtt gtgtactcta agttttcccc       420
aacatatatc acttcactaa taaagacaac cttcgtaagg gttgccgtag ttctctactt       480
gaaatccaat tatctagcat tgtaacccta agttacagac acaaacataa acttgagcaa       540
cttctatgca taagaatcta gggtttcaga ctaactcaat ggaacctaac aagaaataat       600
atccggaccg ctaacgatgc atccaatcga agacaaggtt tcggacactc aacggaacaa       660
ataagggaaa aggatataaa ccactcaacg aagttcatct ctagaatacg tatagtcccc       720
aatacggatt aaccaagtga aacatacac catctaatag catggtcctg caagatagat         780
aactaggtag gaccaccgat ggtataatgt gaccaagtaa gtagtgaccc taaatgtaga       840
ttaaccaagt ggagttaaat ttagaatgca tatgcaccct accccccaa gacagactaa         900 ccaggcagaa ccatatgcat tcccccaata gtgtggttcc ttaatgcaga ttgacaaggc       960
ggaaccacct atgaaaataa tgtaactagg tagggcccga cgaatatcta ttgcctgaaa      1020
tcttaggaga gaattcttgc tctagggac aaatgatttt cgtatgccta agtattttt         1080 atttagtgac agtaaactaa gatttgagta cagagacatt aactgagatt gactcttgtg      1140
aaagcttagt gagttgaagc acttaggcca attatattga gcaatgtgtt aggtgtagcg      1200
tctaaacttc cgtaggagtt ttttacaaca agatagtggg ggtgccgcaa aatgcagaca      1260
gtagcaataa attacgggct aggattatct cccctcgttt ttttgttcca ttccatccct      1320
```

```
tcctctcaca ttctctatt  tgtctttctt tttctaaaaa aaattaatat aagatgttga    1380
tatagcttaa ccgggaccgt tcaaataaga ggggaaggaa gaagaggaaa aaaaaaagag    1440
aggaaggaag aagaggaaaa aaaaaaaaaa agagagggaa gagattttac tttataaatt    1500
acaagcagac acttttgtt  ttttttttt  tttgacaagg agaagcaaac aaacacttga    1560
aaaagcagcg aaagcaggct aaaggtatct tatggtggtc aaagatgtgt gttgtaacta    1620
gttacacgat tctgccttca cattcataga atgtgctttt gaatattata ttacagctag    1680
agaatttgat gtcttaggaa tgttgtcgtg cagaaatgtc agcttttctg cagaaatgtt    1740
agactggtag ctattaacaa gttagactgg ttagactggt agctattaac aagttagact    1800
ggtagctatt aacaactggt agctattaac aagttagact ggtagctatt aacaagttag    1860
actgtgtgtg tgtgtatttc acaagttaga ctggtagcta ttaacaactg ttggaatgtt    1920
ttatatatag cgtgtgtgta tttcacaagt tagaccggta gctaataaca actgttgaaa    1980
tgtttcaaac gtgtcactgt ttgcttctgt ggatatcaga catgcacgtc actggccttg    2040
gaagattaat tagtccgatg gtatccatag cgttaacgtc atggcaaaca cactctaaat    2100
atatatatat atataatggt agctaggtgt ctttctggag tatgaagtgg gtagcaggca    2160
aaagataagc taagtttagc tgctagcaga tacgagatg                          2199
```

<210> SEQ ID NO 16
<211> LENGTH: 244
<212> TYPE: PRT
<213> ORGANISM: Pyrus communis

<400> SEQUENCE: 16

```
Met Glu Gly Tyr Asn Val Asn Leu Ser Val Arg Lys Gly Ala Trp Thr
1               5                   10                  15

Arg Glu Glu Asp Asn Leu Leu Arg Gln Cys Ile Glu Ile His Gly Glu
            20                  25                  30

Gly Lys Trp Asn Gln Val Ser Tyr Lys Ala Gly Leu Asn Arg Cys Arg
        35                  40                  45

Lys Ser Cys Arg Gln Arg Trp Leu Asn Tyr Leu Lys Pro Asn Ile Lys
    50                  55                  60

Arg Gly Asp Phe Lys Glu Asp Glu Val Asp Leu Ile Leu Arg Leu His
65                  70                  75                  80

Arg Leu Leu Gly Asn Arg Trp Ser Leu Ile Ala Arg Arg Leu Pro Gly
                85                  90                  95

Arg Thr Ala Asn Asp Val Lys Asn Tyr Trp Tyr Thr Arg Leu Arg Ile
            100                 105                 110

Asp Ser Arg Met Lys Thr Val Lys Asn Lys Ser Gln Glu Thr Arg Lys
        115                 120                 125

Thr Asn Val Ile Arg Pro Gln Pro Gln Lys Phe Ile Lys Ser Ser Tyr
    130                 135                 140

Tyr Leu Ser Ser Lys Glu Pro Ile Leu Glu His Ile Gln Ser Ala Glu
145                 150                 155                 160

Asp Leu Ser Thr Pro Pro Gln Thr Ser Ser Thr Lys Asn Gly Asn
                165                 170                 175

Asp Trp Trp Glu Thr Leu Phe Glu Gly Glu Asp Thr Phe Glu Arg Ala
            180                 185                 190

Ala Cys Pro Ser Ile Glu Leu Glu Glu Leu Phe Thr Ser Phe Trp
        195                 200                 205

Phe Asp Asp Arg Leu Ser Ala Arg Ser Cys Ala Asn Phe Pro Glu Glu
    210                 215                 220
```

```
Gly Gln Ser Arg Ser Glu Phe Ser Phe Ser Met Asp Leu Trp Asn His
225                 230                 235                 240

Ser Lys Glu Glu

<210> SEQ ID NO 17
<211> LENGTH: 732
<212> TYPE: DNA
<213> ORGANISM: Pyrus communis

<400> SEQUENCE: 17
atggagggat ataacgttaa cttgagtgtg agaaaaggtg cctggactcg agaggaagac      60
aatcttctca ggcagtgcat tgagattcat ggagagggaa agtggaacca agtttcatac     120
aaagcaggct taaacaggtg taggaagagc tgcagacaaa gatggttaaa ctatctgaag     180
ccaaatatca agagaggaga cttaaagag gatgaagtag atcttatact tagacttcac      240
aggcttttgg gaaacaggtg gtcattgatt gctagaagac ttccaggaag aacagcgaat     300
gatgtgaaaa attattggta cactcgattg cggatcgatt ctcgcatgaa aacggtgaaa     360
aataaatctc aagaaacgag aaagaccaat gtgataagac ctcagcccca aaaatttatc     420
aaaagttcat attacttaag cagtaaagaa ccaattctag aacatattca atcagcagaa     480
gatttaagta cgccaccaca aacgtcgtcg tcaacaaaga acggaaatga ttggtgggag     540
accttgttcg aaggcgagga acttttgaa agggctgcat gtcccagcat tgagttagag      600
gaagaactct tcacaagttt ttggtttgat gatcgactgt cggcaagatc atgtgccaat     660
tttcctgaag aaggacaaag tagaagtgaa ttctccttta gcatggacct ttggaatcat     720
tcaaaagaag aa                                                          732

<210> SEQ ID NO 18
<211> LENGTH: 26
<212> TYPE: DNA
<213> ORGANISM: Artificial Sequence
<220> FEATURE:
<223> OTHER INFORMATION: Synthetic construct: primer

<400> SEQUENCE: 18
cactttccct ctccatgaat ctcaac                                            26

<210> SEQ ID NO 19
<211> LENGTH: 27
<212> TYPE: DNA
<213> ORGANISM: Artificial Sequence
<220> FEATURE:
<223> OTHER INFORMATION: Synthetic construct: primer

<400> SEQUENCE: 19
caggttttcg ttatatccct ccatctc                                           27

<210> SEQ ID NO 20
<211> LENGTH: 21
<212> TYPE: DNA
<213> ORGANISM: Artificial Sequence
<220> FEATURE:
<223> OTHER INFORMATION: Synthetic construct: primer

<400> SEQUENCE: 20
accctgaaca cgtgggaacc g                                                 21

<210> SEQ ID NO 21
<211> LENGTH: 28
<212> TYPE: DNA
```

```
<213> ORGANISM: Artificial Sequence
<220> FEATURE:
<223> OTHER INFORMATION: Synthetic construct: primer

<400> SEQUENCE: 21
gctaagctta gctgctagca gataagag                                              28

<210> SEQ ID NO 22
<211> LENGTH: 20
<212> TYPE: DNA
<213> ORGANISM: Artificial Sequence
<220> FEATURE:
<223> OTHER INFORMATION: Synthtetic construct: primer

<400> SEQUENCE: 22 ggagggaat gaagaagagg                                                        20

<210> SEQ ID NO 23
<211> LENGTH: 21
<212> TYPE: DNA
<213> ORGANISM: Artificial Sequence
<220> FEATURE:
<223> OTHER INFORMATION: Synthetic construct: primer

<400> SEQUENCE: 23
tccacagaag caaacactga c                                                     21

<210> SEQ ID NO 24
<211> LENGTH: 21
<212> TYPE: DNA
<213> ORGANISM: Artificial Sequence
<220> FEATURE:
<223> OTHER INFORMATION: Synthetic construct: primer

<400> SEQUENCE: 24
accctgaaca cgtgggaacc g                                                     21

<210> SEQ ID NO 25
<211> LENGTH: 28
<212> TYPE: DNA
<213> ORGANISM: Artificial Sequence
<220> FEATURE:
<223> OTHER INFORMATION: Synthetic construct: primer

<400> SEQUENCE: 25
gctaagctta gctgctagca gataagag                                              28

<210> SEQ ID NO 26
<211> LENGTH: 28
<212> TYPE: DNA
<213> ORGANISM: Artificial Sequence
<220> FEATURE:
<223> OTHER INFORMATION: Synthetic construct: primer

<400> SEQUENCE: 26
ggatccttct gcacgacaac attgacaa                                              28

<210> SEQ ID NO 27
<211> LENGTH: 29
<212> TYPE: DNA
<213> ORGANISM: Artificial Sequence
<220> FEATURE:
<223> OTHER INFORMATION: Synthetic construct: primer

<400> SEQUENCE: 27
gagctcatgt tagcttttct atatatcga                                             29
```

<210> SEQ ID NO 28
<211> LENGTH: 21
<212> TYPE: DNA
<213> ORGANISM: Artificial Sequence
<220> FEATURE:
<223> OTHER INFORMATION: Synthetic construct: primer

<400> SEQUENCE: 28
accctgaaca cgtgggaacc g                                          21

<210> SEQ ID NO 29
<211> LENGTH: 28
<212> TYPE: DNA
<213> ORGANISM: Artificial Sequence
<220> FEATURE:
<223> OTHER INFORMATION: Synthetic construct: primer

<400> SEQUENCE: 29
ctcttatctg ctagcagcta agcttagc                                   28

<210> SEQ ID NO 30
<211> LENGTH: 28
<212> TYPE: DNA
<213> ORGANISM: Artificial Sequence
<220> FEATURE:
<223> OTHER INFORMATION: Synthetic construct: primer

<400> SEQUENCE: 30
cagaaatgtt agactggtag ctattaac                                   28

<210> SEQ ID NO 31
<211> LENGTH: 25
<212> TYPE: DNA
<213> ORGANISM: Artificial Sequence
<220> FEATURE:
<223> OTHER INFORMATION: Synthetic construct: primer

<400> SEQUENCE: 31
ccagtgacgt gcatgtctga tatcc                                      25

<210> SEQ ID NO 32
<211> LENGTH: 233
<212> TYPE: PRT
<213> ORGANISM: Fragaria ananassa

<400> SEQUENCE: 32

Met Glu Gly Phe Gly Val Arg Lys Gly Ala Trp Thr Lys Glu Glu Asp
1               5                   10                  15

Glu Leu Leu Lys Gln Phe Ile Glu Ile His Gly Glu Gly Lys Trp His
            20                  25                  30

His Val Pro Leu Lys Ser Gly Leu Asn Arg Cys Arg Lys Ser Cys Arg
        35                  40                  45

Leu Arg Trp Leu Asn Tyr Leu Lys Pro Asn Ile Lys Arg Gly Glu Phe
    50                  55                  60

Ala Glu Asp Glu Val Asp Leu Ile Ile Arg Leu His Lys Leu Leu Gly
65                  70                  75                  80

Asn Arg Trp Ser Leu Ile Ala Gly Arg Leu Pro Gly Arg Thr Ala Asn
                85                  90                  95

Asp Val Lys Asn Tyr Trp Asn Thr Tyr Gln Arg Lys Lys Asp Gln Lys
            100                 105                 110

Thr Ala Ser Tyr Ala Lys Lys Leu Lys Val Lys Pro Arg Glu Asn Thr
        115                 120                 125

```
Ile Ala Tyr Thr Ile Val Arg Pro Arg Pro Arg Thr Phe Ile Lys Arg
        130                 135                 140

Phe Asn Phe Thr Glu Arg Tyr Ala Asn Ile Glu His Asn His Ser Glu
145                 150                 155                 160

Val Ser Tyr Thr Ser Ser Leu Pro Thr Glu Pro Pro Gln Thr Leu Gln
                165                 170                 175

Leu Glu Asn Val Thr Asp Trp Trp Lys Asp Phe Ser Glu Asp Ser Thr
            180                 185                 190

Glu Ser Ile Asp Arg Thr Met Cys Ser Gly Leu Gly Leu Glu Asp His
        195                 200                 205

Asp Phe Phe Thr Asn Phe Trp Val Glu Asp Met Leu Leu Ser Ala Ser
    210                 215                 220

Asn Asp Leu Val Asn Ile Ser Tyr Val
225                 230

<210> SEQ ID NO 33
<211> LENGTH: 702
<212> TYPE: DNA
<213> ORGANISM: Fragaria ananassa

<400> SEQUENCE: 33
atggagggtt tcggtgtgag aaaaggtgca tggactaaag aggaagatga gcttctgaaa      60
cagttcatcg aaatccatgg agaaggcaaa tggcatcatg ttcctctcaa atcaggctta     120
aacagatgca ggaagagctg tagactgagg tggctgaatt atttgaagcc gaatatcaag     180
agaggagagt ttgcagagga tgaagttgat ttgatcatca ggcttcataa gcttctagga     240
aacaggtggt cttttaattgc cggaagattg ccaggaagaa ctgccaatga tgtgaagaac     300
tattggaata cttatcaaag gaaaaaggat caaaagacgg cttcatacgc aaagaaactg     360
aaagttaaac cccgagaaaa tacaatagct acacaattg taagacctcg accacgaacc      420
ttcatcaaaa ggttcaattt tacagagaga tacgcaaata tagagcataa tcattcagaa     480
gtgagttata ctagttcttt accaacagaa ccaccacaga ctctacaatt agaaaatgta     540
actgattggt ggaaagattt ctcagaagat agtacagaga gcattgatag aacaatgtgt     600
tctggtcttg gtttagagga tcatgacttc ttcacaaact ttggggttga agatatgcta     660
ctatcggcaa gcaatgatct agtcaacatc tcctacgtat ga                         702

<210> SEQ ID NO 34
<211> LENGTH: 248
<212> TYPE: PRT
<213> ORGANISM: Arabidopsis thaliana

<400> SEQUENCE: 34

Met Glu Gly Ser Ser Lys Gly Leu Arg Lys Gly Ala Trp Thr Thr Glu
1               5                   10                  15

Glu Asp Ser Leu Leu Arg Gln Cys Ile Asn Lys Tyr Gly Glu Gly Lys
            20                  25                  30

Trp His Gln Val Pro Val Arg Ala Gly Leu Asn Arg Cys Arg Lys Ser
        35                  40                  45

Cys Arg Leu Arg Trp Leu Asn Tyr Leu Lys Pro Ser Ile Lys Arg Gly
    50                  55                  60

Lys Leu Ser Ser Asp Glu Val Asp Leu Leu Arg Leu His Arg Leu
65                  70                  75              80

Leu Gly Asn Arg Trp Ser Leu Ile Ala Gly Arg Leu Pro Gly Arg Thr
                85                  90                  95

Ala Asn Asp Val Lys Asn Tyr Trp Asn Thr His Leu Ser Lys Lys His
```

```
                        100                 105                 110
Glu Pro Cys Cys Lys Ile Lys Met Lys Lys Arg Asp Ile Thr Pro Ile
            115                 120                 125

Pro Thr Thr Pro Ala Leu Lys Asn Asn Val Tyr Lys Pro Arg Pro Arg
        130                 135                 140

Ser Phe Thr Val Asn Asn Asp Cys Asn His Leu Asn Ala Pro Pro Lys
145                 150                 155                 160

Val Asp Val Asn Pro Pro Cys Leu Gly Leu Asn Ile Asn Asn Val Cys
                165                 170                 175

Asp Asn Ser Ile Ile Tyr Asn Lys Asp Lys Lys Asp Gln Leu Val
            180                 185                 190

Asn Asn Leu Ile Asp Gly Asp Asn Met Trp Leu Glu Lys Phe Leu Glu
        195                 200                 205

Glu Ser Gln Glu Val Asp Ile Leu Val Pro Glu Ala Thr Thr Thr Glu
    210                 215                 220

Lys Gly Asp Thr Leu Ala Phe Asp Val Asp Gln Leu Trp Ser Leu Phe
225                 230                 235                 240

Asp Gly Glu Thr Val Lys Phe Asp
                245

<210> SEQ ID NO 35
<211> LENGTH: 747
<212> TYPE: DNA
<213> ORGANISM: Arabidopsis thaliana

<400> SEQUENCE: 35
atggagggtt cgtccaaagg gctgcgaaaa ggtgcttgga ctactgaaga agatagtctc     60
ttgagacagt gcattaataa gtatggagaa ggcaaatggc accaagttcc tgtaagagct    120
gggctaaacc ggtgcaggaa agttgtaga ttaagatggt tgaactattt gaagccaagt     180
atcaagagag gaaaacttag ctctgatgaa gtcgatcttc ttcttcgcct tcataggctt    240
ctagggaata ggtggtcttt aattgctgga agattacctg gtcggaccgc aaatgacgtc    300
aagaattact ggaacactca tctgagtaag aaacatgaac cgtgttgtaa gataaagatg    360 aaaagagag acattacgcc cattcctaca caccggcac taaaaacaa tgtttataag       420 cctcgacctc gatccttcac agttaacaac gactgcaacc atctcaatgc cccaccaaaa    480
gttgacgtta atcctccatg ccttggactt aacatcaata tgtttgtga caatagtatc     540 atatacaaca agataagaa gaaagaccaa ctagtgaata atttgattga tggagataat    600
atgtggttag agaaattcct agaggaaagc caagaggtag atattttggt tcctgaagcg    660
acgacaacag aaaagggga caccttggct tttgacgttg atcaactttg gagtcttttc    720
gatggagaga ctgtgaaatt tgattag                                        747

<210> SEQ ID NO 36
<211> LENGTH: 1023
<212> TYPE: DNA
<213> ORGANISM: Arabidopsis thaliana

<400> SEQUENCE: 36
atgcttttct tagaaaatga ataaaaccg gcgttttata tataagtgtt tcttttctc      60 ttctgtccag aagtaaatca ttaagaacca atatggcttt tcttaaacta atctccgtga    120
taatcaaatc tttgatcatt ctccacacaa tcccatcaac aacatcgatc tcactagatg    180
caccaacaat gattctaatc ggcactacta actatagaga tagttgtccc aaaaaaaaa     240 aaaaaaacta actagagaga taaatcatat tcaatacatg tactatttct actatactta    300
```

```
agaaaatttg tataccacta tcttaactct taacactgaa catactatac actatcttaa       360
ctcccaactc ttgtaaaaga atatctaatt ttaagaaaag acttcaaatg cttgttaaat       420
ttctagtgaa gatgcacatt ctaaaaactg gtaaaatggt aagaaaaaaa tatataaaaa       480
aatagcctta ttaaaattta tatctcctat ttctctatcc aaactacacg gatgaagctt       540
attgttattc atccacccct ttttctcaatt ctgtcctatt tcttgtgcat gaaacttctc     600
catcttgtaa tcggataaat catacccaaa tttttcttt ctgaaaacat atatacccga        660
acattaatta ctatcgtcct ttctcctaat tttgttaaga acatgtttg tttgttttta        720 gtactgaaaa aggatggaga tacttgctag atcctatgaa cctttctct ctaggacaaa        780 tcagtaacca aacaataact tagcaaatta agcacgacag ctaatacata aaatgtggat       840
atcaaacatg cacgtcactt ccttttttcc gtcacgtgtt tttataaatt ttctcacata      900
ctcacactct ctataagacc tccaatcatt tgtgaaacca tactatatat accctcttcc      960
ttgaccaatt tacttatacc ttttacaatt tgtttatata ttttacgtat ctatctttgt     1020
tcc                                                                    1023

<210> SEQ ID NO 37
<211> LENGTH: 1227
<212> TYPE: DNA
<213> ORGANISM: Artificial Sequence
<220> FEATURE:
<223> OTHER INFORMATION: Synthetic construct: Chimeric promoter

<400> SEQUENCE: 37
atgcttttct tagaaaatga taataaaccg gcgttttata aataagtgtt tctttttctc        60
ttctgtccag aagtaaatca ttaagaacca atgtggcttt tcttaaacta atctccgtga       120
taatcaaatc tttgatcatt ctccacacaa tcccatccac aacatcgatc tcactagatg       180
caccaacaat gattctaatc ggcactacta actatagaga tagttgtccc aaaaaaaaaa       240
aaaaaaacta actagagaga taaatcatat tcaatacatg tactatttct actatactta       300
agaaaatttg tataccacta tcttaactct taacactgaa catactatac actatcttaa       360
ctcccaactc ttgtaaaaga atatctaatt ttaagaaaag acttcaaatg cttgttaaat       420
ttctagtgaa gatgcacatt ctaaaaactg gtaaaatggt aagaaaaaaa tatataaaaa       480
aatagcctta ttaaaattta tatctcctat ttctctatcc aaactacacg gatgaagctt       540
gtgcagaaat gttagactgg tagctattaa caagttagac tggttagact ggtagctatt      600
aacaagttag actggtagct attaacaact ggtagctatt aacaagttag actggtagct      660
attaacaagt tagactgtgt gtgtgtgtgt atttcacaag ttagactggt agctattaac      720
aactgttgga atgttttagc ttattgttat tcatccaccc ttttttctcaa ttctgtccta    780 tttcttgtgc atgaaacttc tccatcttgt aatcggataa atcataccca atttttttct      840
ttctgaaaac atatataccc gaacattaat tactatcgtc ctttctccta ttttgttaa      900 gaaacatgtt tgttggtttt tagtactgaa aaaggatgga gatacttgct agatcctatg      960
aaccttttct ctctaggaca aatcagtaac caaacaataa cttagcaaat taagcacgac     1020
agctaataca taaatgtgg atatcaaaca tgcacgtcac ttccttttt ccgtcacgtg       1080 tttttataaa ttttctcaca tactcacact ctctataaga cctccaatca tttgtccgaa     1140
accatactat atatacccctc ttccttgacc aatttactta tccttttac aatttgttta     1200 tatattttac gtatctatct ttgttcc                                          1227
```

```
<210> SEQ ID NO 38
<211> LENGTH: 2130
<212> TYPE: DNA
<213> ORGANISM: Actinidia eriantha
<220> FEATURE:
<221> NAME/KEY: misc_feature
<222> LOCATION: (556)..(556)
<223> OTHER INFORMATION: n is a, c, g, or t
<220> FEATURE:
<221> NAME/KEY: misc_feature
<222> LOCATION: (1261)..(1261)
<223> OTHER INFORMATION: n is a, c, g, or t
<220> FEATURE:
<221> NAME/KEY: misc_feature
<222> LOCATION: (1750)..(1750)
<223> OTHER INFORMATION: n is a, c, g, or t
<220> FEATURE:
<221> NAME/KEY: misc_feature
<222> LOCATION: (1754)..(1755)
<223> OTHER INFORMATION: n is a, c, g, or t

<400> SEQUENCE: 38
atcccaaaat atttgttcac ttagaaaatt aactgataaa ataatgcaaa ctctcctttt      60
tgttctcctc ttttgaattg acgtgacaca tttatctttt taattttaga taatttcgaa     120
ttattgaaaa aaaattaaac tgttttccaa ataataattt tttagaaata atgcaaataa     180
tagtttttta aactattttc caaatatttt ttttcaaaaa taatgcatta ttaagaataa     240
tattaaaaaa tatcttcaaa tattaaaaaa tatattttg ataaaattta ataatatata      300
aaaataaatg aatgtttttg tttgcataaa caatttctaa taaaatatttt tgcgaaaatg    360 tttttgtttg cataaacaat ttctaataaa atattttgcg aaaatgtttt tgttcgcata     420
aacaatttct gataaaattt tttgcaaaac taaacctaac acaaatgggt agcattttg      480 cttctttaaa atcttggatt ccctaaatta gacaaataaa ttgggacgga tcaacattta     540
ttttcttctt aattwntttc tctaacacta caacaaaata attaaataga taagaaaaga    600
gaaaaaggaa cttgagaacc cacccaactt ttaaacattg cagttgggtc cttccgtacg     660
ttgcagtggt cctccacaac gtccacatga accacatggg cgtggttaat acaacgcacc     720
ccactctctc tctctctctc tctctctcga taattgtctc cattcgcagt aaaattacca     780
aggccactcg tcccacagtg cacaccacgg ccgatccaca gccacactca ccaatcacct     840
ctctctctct ctctctctct agaatttatt tgttgctctt ggagcaacac gtcacttttt     900
gacacgtggt ggtcggatcc aatcatctca cgccatccaa gcactcagtt tcatgtgttt     960
gccacgtcac cacaacaatt ccaccacaaa cccaggtaaa cacaagacta acagaacctc    1020
actccgttaa tgccatcttc ctgtcgctga ctcgcatgaa ataccaccac ttttggaaac    1080
caaacgccag aaaagattac tctcaccaat attctctatg aacaagaaa ttgggttatt     1140 atttattatt tacaagaaat aaatggcacc aaccaaattt aaaaagacgt ctctgcagcg    1200
attttcacct cattttattt tttgagcttt taggtgtctc gtccgaaacc gacgccttct    1260
ntattatgca attttttcact cttctttgcc ttctcagtcc cgaaatgact attttcaggc   1320
aacatcatag ggtgattggg ttgtttagct atgtaggtac gaaatctaaa aatttgaatt    1380
tgtaaagttt atgaatattt catcgcatcg agtactggcg gaatgttcac ggggttaaca    1440
ggatttgaac tccgttattt cttctcttgag taaacggacg tggctgaata cacggacaac   1500
caattaaatg gtgtatgata tttcgtgtgg agcaccacgc gtagaaagtg aggtgttgcg    1560
tcaagagcat caaataattt ctcctctctc tctctccctc ttctctatct atatatcccc    1620
caatctggcc tctcctcacc tcaccccaa agtctacaca gaatcaaccc ttcatctccc     1680
gcataggcct cccaaaccca cctcttctcc acaatccaga cacacctcga gtggccggag    1740
```

```
tttagagagn agannngagag agagattttc tgcttcgatc gggggggtaaa acccggtgtt    1800 tgacaagttg tagacatcac ggctataatc ggagtttctc ggccgctcat acatgtccgg    1860
tctgtacgac gcaagggttg tgtagtcgag agcaacccct tcgccgcacgg cggacgtggc    1920 gccttgccgt ccgaaggcgg tagcccctcc gacctcctct tcctcgccgg cggcggtcac    1980
ttcgctttct ccgtctacta gcttattagg tttattctta cttagtgagt aattcgtcct    2040
attatagttc gtaagttcat caaagatctg ttacttgatt cgtctttcgt tgctcgagtc    2100
ttggtgtttt ttgcgttttc tgagttcgag                                     2130
```

<210> SEQ ID NO 39
<211> LENGTH: 2320
<212> TYPE: DNA
<213> ORGANISM: Artificial Sequence
<220> FEATURE:
<223> OTHER INFORMATION: Synthetic construct: Chimeric promoter
<220> FEATURE:
<221> NAME/KEY: misc_feature
<222> LOCATION: (556)..(556)
<223> OTHER INFORMATION: n is a, c, g, or t
<220> FEATURE:
<221> NAME/KEY: misc_feature
<222> LOCATION: (1261)..(1261)
<223> OTHER INFORMATION: n is a, c, g, or t
<220> FEATURE:
<221> NAME/KEY: misc_feature
<222> LOCATION: (1937)..(1937)
<223> OTHER INFORMATION: n is a, c, g, or t
<220> FEATURE:
<221> NAME/KEY: misc_feature
<222> LOCATION: (1941)..(1942)
<223> OTHER INFORMATION: n is a, c, g, or t
<220> FEATURE:
<221> NAME/KEY: misc_feature
<222> LOCATION: (1941)..(1942)
<223> OTHER INFORMATION: n is a, c, g, or t

<400> SEQUENCE: 39

```
atcccaaaat atttgttcac ttagaaaatt aactgataaa ataatgcaaa ctctcctttt      60
tgttctcctc ttttgaattg acgtgacaca tttatctttt taattttaga taatttcgaa    120
ttattgaaaa aaaattaaac tgttttccaa ataataattt tttagaaata atgcaaataa    180
tagtttttta aactattttc caaatatttt ttttcaaaaa taatgcatta ttaagaataa    240
tattaaaaaa tatcttcaaa tattaaaaaa tatattttg ataaaattta ataatatata     300
aaaataaatg aatgttttg tttgcataaa caatttctaa taaaatattt tgcgaaaatg     360
tttttgtttg cataaacaat ttctaataaa atattttgcg aaaatgtttt tgttcgcata    420
aacaatttct gataaaattt tttgcaaaac taaacctaac acaatggggt agcatttttg    480
cttctttaaa atcttggatt ccctaaatta gacaaataaa ttgggacgga tcaacattta    540
ttttcttctt aattwntttc tctaacacta caacaaaata attaaataga taagaaaaga    600
gaaaaaggaa cttgagaacc cacccaactt ttaaacattg cagttgggtc cttccgtacg    660
ttgcagtggt cctccacaac gtccacatga accacatggg cgtggttaat acaacgcacc    720
ccactctctc tctctctctc tctctctcga taattgtctc cattcgcagt aaaattacca    780
aggccactcg tcccacagtg cacaccacgg ccgatccaca gccacactca ccaatcacct    840
ctctctctct ctctctctct agaatttatt tgttgctctt ggagcaacac gtcactttt     900 gacacgtggt ggtcggatcc aatcatctca cgccatccaa gcactcagtt tcatgtgttt    960
gccacgtcac cacaacaatt ccaccacaaa cccaggtaaa cacaagacta acagaacctc   1020
actccgttaa tgccatcttc ctgtcgctga ctcgcatgaa ataccaccac ttttggaaac   1080
```

```
caaacgccag aaaagattac tctcaccaat attctctatg aacaaagaaa ttgggttatt    1140
atttattatt tacaagaaat aaatggcacc aaccaaattt aaaaagacgt ctctgcagcg    1200
attttcacct cattttattt tttgagcttt taggtgtctc gtccgaaacc gacgccttct    1260
ntattatgca attttccact cttctttgcc ttctcagtcc cgaaatgact attttcaggc    1320
aacatcatag ggtgattggg ttgtttagct atgtaggtac gaaatctaaa aatttgaatt    1380
tgtaaagttt atgaatattt catcgcatcg agtactggcg gaatgttcac ggggtaatgt    1440
tagactggta gctattaaca agttagactg gttagactgg tagatattaa caagttagac    1500
tggtagctat taacaactgg tagctattaa caagttagac tggtagctat taacaagtta    1560
gactgtgtgt gtgtgtattt cacaagttag actggtagct attaacaact gttggaatgt    1620
tttaacagga tttgaactcc gttatttctt tcttgagtaa acggacgtgg ctgaatacac    1680
ggacaaccaa ttaaatggtg tatgatattt cgtgtggagc accacgcgta gaaagtgagg    1740
tgttgcgtca agagcatcaa ataatttctc ctctctctct ctccctcttc tctatctata    1800
tatcccccaa tctggcctct cctcacctca cccccaaagt ctacacagaa tcaacccttc    1860
atctcccgca taggcctccc aaacccacct cttctccaca atccagacac acctcgagtg    1920
gccggagttt agagagnaga nngagagaga gattttctgc ttcgatcggg gggtaaaacc    1980
cggtgtttga caagttgtag acatcacggc tataatcgga gtttctcggc cgctcataca    2040
tgtccggtct gtacgacgca agggttgtgt agtcgagagc aacccttcgc cgcacggcgg    2100
acgtggcgcc ttgccgtccg aaggcggtag cccctccgac ctcctcttcc tcgccggcgg    2160
cggtcacttc gctttctccg tctactagct tattaggttt attcttactt agtgagtaat    2220
tcgtcctatt atagttcgta agttcatcaa agatctgtta cttgattcgt ctttcgttgc    2280
tcgagtcttg gtgttttttg cgttttctga gttcgagatg                         2320

<210> SEQ ID NO 40
<211> LENGTH: 2510
<212> TYPE: DNA
<213> ORGANISM: Artificial Sequence
<220> FEATURE:
<223> OTHER INFORMATION: Synthetic construct: Chimeric promoter
<220> FEATURE:
<221> NAME/KEY: misc_feature
<222> LOCATION: (556)..(556)
<223> OTHER INFORMATION: n is a, c, g, or t
<220> FEATURE:
<221> NAME/KEY: misc_feature
<222> LOCATION: (1261)..(1261)
<223> OTHER INFORMATION: n is a, c, g, or t
<220> FEATURE:
<221> NAME/KEY: misc_feature
<222> LOCATION: (2130)..(2130)
<223> OTHER INFORMATION: n is a, c, g, or t
<220> FEATURE:
<221> NAME/KEY: misc_feature
<222> LOCATION: (2134)..(2135)
<223> OTHER INFORMATION: n is a, c, g, or t

<400> SEQUENCE: 40
atcccaaaat atttgttcac ttagaaaatt aactgataaa ataatgcaaa ctctcctttt      60
tgttctcctc ttttgaattg acgtgacaca tttatctttt taattttaga taatttcgaa     120
ttattgaaaa aaaattaaac tgttttccaa ataataattt ttagaaaata atgcaaataa     180 tagttttttta aactattttc caaatatttt ttttcaaaaa taatgcatta ttaagaataa     240
tattaaaaaa tatcttcaaa tattaaaaaa tatattttg ataaaattta ataatatata      300
aaaataaatg aatgttttg tttgcataaa caatttctaa taaaatattt tgcgaaaatg      360
```

```
tttttgtttg cataaacaat ttctaataaa atattttgcg aaaatgtttt tgttcgcata      420
aacaatttct gataaaattt tttgcaaaac taaacctaac acaaatgggt agcattttg       480 cttctttaaa atcttggatt ccctaaatta gacaaataaa ttgggacgga tcaacattta      540
ttttcttctt aattwntttc tctaacacta caacaaaata attaaataga taagaaaaga     600
gaaaaaggaa cttgagaacc cacccaactt ttaaacattg cagttgggtc cttccgtacg      660
ttgcagtggt cctccacaac gtccacatga accacatggg cgtggttaat acaacgcacc      720
ccactctctc tctctctctc tctctctcga taattgtctc cattcgcagt aaaattacca      780
aggccactcg tcccacagtg cacaccacgg ccgatccaca gccacactca ccaatcacct      840
ctctctctct ctctctctct agaatttatt tgttgctctt ggagcaacac gtcacttttt      900
gacacgtggt ggtcggatcc aatcatctca cgccatccaa gcactcagtt tcatgtgttt      960
gccacgtcac cacaacaatt ccaccacaaa cccaggtaaa cacaagacta acagaacctc     1020
actccgttaa tgccatcttc ctgtcgctga ctcgcatgaa ataccaccac ttttggaaac     1080
caaacgccag aaaagattac tctcaccaat attctctatg aacaaagaaa ttgggttatt     1140
atttattatt tacaagaaat aaatggcacc aaccaaattt aaaagacgt ctctgcagcg      1200 attttcacct catttttattt tttgagcttt taggtgtctc gtccgaaacc gacgccttct    1260
ntattatgca attttcact cttctttgcc ttctcagtcc cgaaatgact attttcaggc      1320
aacatcatag ggtgattggg ttgtttagct atgtaggtac gaaatctaaa aatttgaatt     1380
tgtaaagttt atgaatattt catcgcatcg agtactggcg gaatgttcac ggggttaatg     1440
ttagactggt agctattaac aagttagact ggttagactg gtagatatta acaagttaga    1500
ctggtagcta ttaacaactg gtagctatta acaagttaga ctggtagcta ttaacaagtt    1560
agactgtgtg tgtgtgtatt tcacaagtta gactggtagc tattaacaac tgttggaatg    1620
ttttgcagaa atgttagact ggtagctatt aacaagttag actggttaga ctggtagcta    1680
ttaacaagtt agactggtag ctattaacaa ctggtagcta ttaacaagtt agactggtag    1740
ctattaacaa gttagactgt gtgtgtgtgt atttcacaag ttagactggt agctattaac    1800
aactgttgga atgttttaca ggatttgaac tccgttattt ctttcttgag taaacggacg    1860
tggctgaata cacggacaac caattaaatg gtgtatgata tttcgtgtgg agcaccacgc    1920
gtagaaagtg aggtgttgcg tcaagagcat caaataattt ctcctctctc tctctccctc    1980
ttctctatct atatatcccc caatctggcc tctcctcacc tcaccccaa agtctacaca      2040 gaatcaaccc ttcatctccc gcataggcct cccaaaccca cctcttctcc acaatccaga    2100
cacacctcga gtggccggag tttagagagn agannngagag agagattttc tgcttcgatc    2160 gggggtaaa accggtgtt tgacaagttg tagacatcac ggctataatc ggagtttctc       2220
ggccgctcat acatgtccgg tctgtacgac gcaggggttg tgtagtcgag agcaacccctt    2280 cgccgcacgg cggacgtggc gccttgccgt ccgaaggcgg tagcccctcc gacctcctct     2340
tcctcgccgg cggcggtcac ttcgctttct ccgtctacta gcttattagg tttattctta    2400
cttagtgagt aattcgtcct attatagttc gtaagttcat caaagatctg ttacttgatt    2460
cgtctttcgt tgctcgagtc ttggtgtttt ttgcgttttc tgagttcgag                2510
```

<210> SEQ ID NO 41
<211> LENGTH: 23
<212> TYPE: DNA
<213> ORGANISM: Artificial Sequence
<220> FEATURE:
<223> OTHER INFORMATION: Synthetic construct: consensus motif

```
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 41
gttagacngg tagctantaa caa                                            23

<210> SEQ ID NO 42
<211> LENGTH: 23
<212> TYPE: DNA
<213> ORGANISM: Artificial Sequence
<220> FEATURE:
<223> OTHER INFORMATION: Synthetic construct:   consensus motif
<220> FEATURE:
<221> NAME/KEY: misc_feature
<222> LOCATION: (8)..(8)
<223> OTHER INFORMATION: n = c or t
<220> FEATURE:
<221> NAME/KEY: misc_feature
<222> LOCATION: (17)..(17)
<223> OTHER INFORMATION: w = a or t

<400> SEQUENCE: 42
gttagacngg tagctawtaa caa                                            23

<210> SEQ ID NO 43
<211> LENGTH: 1704
<212> TYPE: DNA
<213> ORGANISM: Malus domestica

<400> SEQUENCE: 43
atgagctcac cctgaacacg tgggaaccgg cccgtttgta accgactgag ataggtccgg      60
ttctatttct taaaaaccca acacccgcta tgttctattt ataaacgggt ccggtctggt     120
ccctccaact ttgagcccgg ctcgacttgt gcccactcct aaactaaacc atataaaaac     180
caagatttcc cttttcttct ttcacacata tcacgttact ttccaacaac aattcaacaa     240
tcacaacaaa taatcaacca tcaagatcat atatcacgtc actaataaag acaaccttca     300
caagggttgt cgtagttctc tactggaaat ccaattgtct agcattgtaa ccctaagtta     360
cagacacaaa cataaacttg agcaacttct atgcataaga atctggggtt ttggactaac     420
tcaacagaac ctaacaagaa ataatattct ggaccgctta acggaatcca acgaagacaa     480
ggtttcggac cactcaacgg aacaaataag ggaaagggat ataaccatt caacgaaatc      540 catctttaga atacgcatag tctcccaata cggattaacc aagtgagaac atacgccatc     600
tgatagcgtg gtcccgcaag acagataacc aagtaggacc accgatggta taatgtgacc     660
aagtaagcag tgaccctaaa tgtagattaa ccacatggag ttaaattaac aaggctgaac     720
cacctatgaa ataatgtaa gcctgaaatc ttaggagaga attcttgctc tagggacaa      780 atgattttcg tatgcctaag tgttttttta gtgacagtaa actaagattt gagtacagag     840
acattaactg agattgactc ttgtgaaagc ttagtgagtt gaagcacgta ggccaattat     900
attgagcaat gtgttaggtg tagcgtctaa acttccgtag gagttttgta cagcaatata     960 gtggggtgc cgcaaaatgc agacagtagc aataaattac gggctaggat tttctcctct    1020
ttttttttcg ttccattcca tccattcctc tcacatttt tattttgtct ttctcttct    1080 ataaaaaatt aatataagat gttaatgtaa cttgaccgtg actattcaaa taggagggga    1140
atgaagaaga gggaaaaaaa ggagagaatc ctactccata aattacaagc aaacactttt    1200
```

```
tttttttttt tgacaagcag aagcaaacaa acacttgaaa aagcagcgaa agcatgataa    1260
aggtatctta tggtggtcaa agatgtgtgt tgtaactagt tacacgattc tgcattcaca    1320
ttcatagaat gtgcttttga atattatatt acagctagag aattttatgc cctgggattg    1380 atttccttg tcaatgttgt cgtgcagaaa tgttagcttt tctatatatc gagtgtgtgt     1440
gtgtgtgtgt atttcacaag ttagactggt agctaataac aactgttgga atgttttaaa    1500
cttgtcagtg tttgcttctg tggatatcag acatgcacgt cactggcctt gtaagattaa    1560
ttaggccgat ggtatccata gcgttaatgt catggcaaac acactctaat tatatataat    1620
ggtagctagg tgtctttctg gagtgtatga agtgggtagc aggcaaaaga atagctaagc    1680
ttagctgcta gcagataaga gatg                                           1704

<210> SEQ ID NO 44
<211> LENGTH: 245
<212> TYPE: DNA
<213> ORGANISM: Artificial Sequence
<220> FEATURE:
<223> OTHER INFORMATION: Synthetic construct:  amplified sequence.

<400> SEQUENCE: 44
tgcagaaatg ttagactggt agctattaac aagttagact ggttagactg gtagctatta     60
acaagttaga ctggtagcta ttaacaactg gtagctatta acaagttaga ctggtagcta    120
ttaacaagtt agactgtgtg tgtgtgtgta tttcacaagt tagactggta gctattaaca    180
actgttggaa tgttttaaac ttgtcagtgt ttgcttctgt ggatatcaga catgcacgtc    240
actgg                                                                245
```